United States Patent
Yoshida et al.

(10) Patent No.: US 9,871,209 B2
(45) Date of Patent: Jan. 16, 2018

(54) TRANSPARENT ELECTRODE, ELECTRONIC DEVICE, AND ORGANIC ELECTROLUMINESCENT DEVICE

(71) Applicant: Konica Minolta, Inc., Tokyo (JP)

(72) Inventors: Kazuhiro Yoshida, Tachikawa (JP);
Takeshi Hakii, Sagamihara (JP);
Hiroshi Ishidai, Hachioji (JP);
Toshiyuki Kinoshita, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 370 days.

(21) Appl. No.: 14/647,262

(22) PCT Filed: Nov. 25, 2013

(86) PCT No.: PCT/JP2013/081653
§ 371 (c)(1),
(2) Date: May 26, 2015

(87) PCT Pub. No.: WO2014/084170
PCT Pub. Date: Jun. 5, 2014

(65) Prior Publication Data
US 2015/0311452 A1    Oct. 29, 2015

(30) Foreign Application Priority Data

Nov. 28, 2012 (JP) ................. 2012-260041

(51) Int. Cl.
| | |
|---|---|
| *H01L 51/00* | (2006.01) |
| *C07D 405/14* | (2006.01) |
| *C07D 409/14* | (2006.01) |
| *C07D 471/04* | (2006.01) |
| *C07D 471/14* | (2006.01) |
| *C07D 519/00* | (2006.01) |
| *C07D 405/10* | (2006.01) |
| *C07D 417/14* | (2006.01) |

(Continued)

(52) U.S. Cl.
CPC ........ *H01L 51/0072* (2013.01); *C07D 405/10* (2013.01); *C07D 405/14* (2013.01);
(Continued)

(58) Field of Classification Search
None
See application file for complete search history.

(56) References Cited

U.S. PATENT DOCUMENTS 8,487,527 B2 * 7/2013 Aziz .................... H01L 51/5012
257/40
2004/0245917 A1 * 12/2004 Lu ...................... H01L 51/5203
313/503

(Continued)

FOREIGN PATENT DOCUMENTS

| CN | 102850334 | * | 2/2013 | .......... C07D 413/14 |
| JP | 2002015623 A | | 1/2002 | |

(Continued)

OTHER PUBLICATIONS

Machine translation of CN-102850334, 13 pages, translation dated Oct. 2017 (Year: 2017).*

(Continued)

*Primary Examiner* — Robert S Loewe
(74) *Attorney, Agent, or Firm* — Lucas & Mercanti, LLP

(57) ABSTRACT

Provided is a transparent electrode including a nitrogen-containing layer and an electrode layer provided adjacent thereto. The nitrogen-containing layer includes a compound that contains a nitrogen atom or atoms and has an effective lone pair content n/M of $2.0 \times 10^{-3}$ or more, wherein n represents the number of unshared electron pairs that neither contribute to aromaticity nor are coordinated to metal among the unshared electron pairs of the nitrogen atom or atoms, and M represents the molecular weight of the compound. The electrode layer includes silver as a main component and at least one additive element selected from aluminum, gold, indium, copper, palladium, and platinum.

20 Claims, 6 Drawing Sheets

(51) Int. Cl.
    *C07D 493/04*     (2006.01)
    *C07D 495/04*     (2006.01)
    *C07D 495/14*     (2006.01)
    *H01L 51/52*     (2006.01)

(52) U.S. Cl.
    CPC ......... *C07D 409/14* (2013.01); *C07D 417/14* (2013.01); *C07D 471/04* (2013.01); *C07D 471/14* (2013.01); *C07D 493/04* (2013.01); *C07D 495/04* (2013.01); *C07D 495/14* (2013.01); *C07D 519/00* (2013.01); *H01L 51/006* (2013.01); *H01L 51/5206* (2013.01); *H01L 51/5215* (2013.01); *H01L 51/0067* (2013.01); *H01L 51/0073* (2013.01); *H01L 51/0085* (2013.01); *H01L 51/5234* (2013.01)

(56) References Cited

U.S. PATENT DOCUMENTS

| | | |
|---|---|---|
| 2009/0284138 A1 | 11/2009 | Yasukawa et al. |
| 2011/0057920 A1 | 3/2011 | Matsura et al. |

FOREIGN PATENT DOCUMENTS

| | | |
|---|---|---|
| JP | 2005026221 A | 1/2005 |
| JP | 2006164961 A | 6/2006 |
| JP | 2008171637 A | 7/2008 |
| JP | 2009151963 A | 7/2009 |
| JP | 2009301858 A | 12/2009 |
| JP | 2010251675 A | 11/2010 |
| JP | 2011054419 A | 3/2011 |
| JP | 2011077028 A | 4/2011 |
| JP | 2013128122 A | 6/2013 |
| WO | 2009054253 A1 | 4/2009 |
| WO | 2011004807 A1 | 1/2011 |

OTHER PUBLICATIONS

International Search Report dated Jan. 28, 2014 for PCT/JP2013/081653 and English translation.

Office Action dated Apr. 21, 2016; Application No. 2013800610260; English translation of Office Action: Total of 16 pages.

Official Notice of Reasons for Rejection dated May 30, 2017 from the corresponding Japanese Patent Application No. JP 2014-550179 and English translation; Total of 12 pages.

\* cited by examiner

TBAC          Ir(ppy)₃

TRANSPARENT ELECTRODE, ELECTRONIC DEVICE, AND ORGANIC ELECTROLUMINESCENT DEVICE

CROSS REFERENCE TO RELATED APPLICATION

This Application is a 371 of PCT/JP2013/081653 filed on Nov. 25, 2013 which, in turn, claimed the priority of Japanese Patent Application No. JP2012-260041 filed on Nov. 28, 2012, both applications are incorporated herein by reference.

TECHNICAL FIELD

The present invention relates to a transparent electrode, an electronic device, and an organic electroluminescent device. More specifically, the present invention relates to a transparent electrode having both conductivity and optical transparency and to an electronic device and an organic electroluminescent device each having such a transparent electrode.

BACKGROUND ART

Organic electroluminescent devices, which operate by electroluminescence (hereinafter abbreviated as EL) from organic materials, (what are called organic EL devices), are completely solid devices of a thin film type capable of emitting light at a low voltage ranging from several V to several 10 V and have many good characteristics such as high luminance, high emission efficiency, small thickness, and lightweight. In recent years, therefore, they have attracted attention as backlights for a variety of displays, display boards for signboards, emergency lights, and the like, and surface emitting devices for illumination light sources, etc.

Such organic electroluminescent devices have a structure including two electrodes and a light-emitting layer including an organic material disposed between the electrodes, in which light produced by the light-emitting layer is extracted through the electrode. Therefore, at least one of the two electrodes is formed as a transparent electrode.

Transparent electrodes generally used include oxide semiconductor materials such as ITO (indium tin oxide, $SnO_2$—$In_2O_3$). A stack of ITO and silver layers is also studied to provide lower resistance (e.g., refer to Patent Literatures 1 and 2 listed below). Unfortunately, ITO, which contains a rare metal, indium, is a high-cost material and needs to be annealed at about 300° C. for resistance reduction after it is deposited as a film. Therefore, there are proposed a thin film of a high-conductivity metal material such as silver and a film of a mixture of silver and aluminum, which can ensure conductivity with a thickness smaller than that of a film of silver alone (e.g., refer to Patent Literature 3 listed below). There is also proposed a multilayer structure including an underlying layer of a metal other than silver and a silver thin-film layer provided on the underlying layer so that optical transparency can be ensured (e.g., refer to Patent Literature 4 listed below).

CITATION LIST

Patent Literatures

Patent Literature 1: JP 2002-15623 A
Patent Literature 2: JP 2006-164961 A
Patent Literature 3: JP 2009-151963 A
Patent Literature 4: JP 2008-171637 A

SUMMARY OF INVENTION

Technical Problem

However, even when high-conductivity materials such as silver and aluminum are used, it is difficult to form transparent electrodes having both sufficient conductivity and sufficient optical transparency.

It is therefore an object of the present invention to provide a transparent electrode having both sufficient conductivity and sufficient optical transparency and to provide an electronic device and an organic electroluminescent device each produced with such a transparent electrode and thus having improved performance.

Solution to Problem

In order to achieve the object, a transparent electrode according to the present invention has the following configurations. The transparent electrode includes a nitrogen-containing layer comprising a compound that contains a nitrogen atom or atoms having an unshared electron pair or pairs and has an effective lone pair content n/M of $2.0\times10^{-3}$ or more, wherein n represents the number of unshared electron pairs that neither contribute to aromaticity nor are coordinated to metal among the unshared electron pair or pairs of the nitrogen atom or atoms, and M represents the molecular weight of the compound. The transparent electrode further includes an electrode layer provided adjacent to the nitrogen-containing layer and comprising silver (Ag) as a main component and at least one additive element selected from aluminum (Al), gold (Au), indium (In), copper (Cu), palladium (Pd), and platinum (Pt).

The electronic device of the present invention is characterized by having the transparent electrode configured as stated above. The electronic device is, for example, an organic electroluminescent device.

The transparent electrode, configured as stated above, includes the nitrogen-containing layer including a nitrogen atom-containing compound; and the electrode layer that includes silver as a main component and is provided adjacent to the nitrogen-containing layer. In the electrode layer including silver as a main component, therefore, silver at the adjacent interface is reduced in diffusion length and inhibited from aggregating by the interaction with nitrogen atoms in the nitrogen-containing layer. Concerning the electrode layer, therefore, a thin silver film can be formed in a monolayer growth mode (Frank van der Merwe (FM) mode) although in general, silver can easily form isolated islands due to nucleation growth (Volumer Weber (VW) mode). Thus, the electrode layer can be obtained with a uniform thickness even when it has a small thickness.

In addition, the effective lone pair content [n/M] is used as an index to the stability of the ability of silver in the electrode layer to bond the nitrogen-containing layer, and a compound with an effective lone pair content of $2.0\times10^{-3}$ or more ($2.0\times10^{-3} \leq [n/M]$) is used to form the nitrogen-containing layer. This makes it possible to form, adjacent to the electrode layer, a nitrogen-containing layer capable of reliably producing the effect of "inhibiting the aggregation of silver" as stated above. As described in detail in Examples below, this effect has also been demonstrated from the fact that a very thin electrode layer with a thickness of 6 nm capable of being measured for sheet resistance is formed on such a nitrogen-containing layer.

In addition, the electrode layer including silver (Ag) as a main component particularly contains at least one of aluminum (Al), gold (Au), indium (In), copper (Cu), palladium (Pd), and platinum (Pt), which are elements capable of forming a solid solution with silver. This allows the electrode layer to include a solid solution of silver (Ag) and any of these additive elements, so that the migration of silver (Ag) is suppressed in the electrode layer.

Thus it is ensured that the electrode layer in the transparent electrode can be thin so that it will reliably have optical transparency, and can also have uniform thickness so that it will have reliable conductivity. In addition, the suppression of the migration makes it possible to maintain such optical transparency and conductivity. Therefore, the transparent electrode including silver can have both higher conductivity and higher optical transparency and also have higher reliability.

Advantageous Effects of Invention

As described above, the present invention makes it possible to improve both the conductivity and the optical transparency of transparent electrodes and to improve the reliability of transparent electrodes. The use of the transparent electrode makes it possible to obtain electronic devices and organic electroluminescent devices with improved performance.

DESCRIPTION OF EMBODIMENTS

Hereinafter, embodiments of the present invention will be described in the order shown below with reference to the drawings.
1. Transparent electrode
2. Applications of transparent electrode
3. First example of organic electroluminescent device (top emission type)
4. Second example of organic electroluminescent device (bottom emission type)
5. Third example of organic electroluminescent device (double-sided emission type)
6. Fourth example of organic electroluminescent device (inverted structure)
7. Applications of organic electroluminescent device
8. Illumination device I
9. Illumination device II <<1. Transparent Electrode>>

Figure 1:
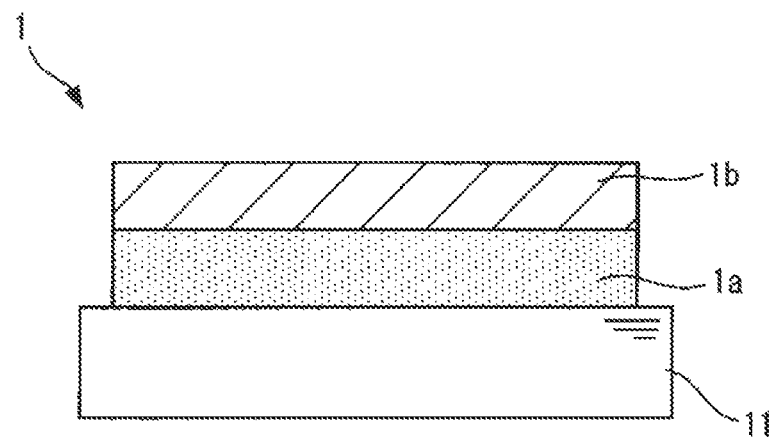
FIG. 1 is a schematic cross-sectional view illustrating the structure of a transparent electrode according to the present invention.

FIG. 1 is a schematic cross-sectional view illustrating the structure of a transparent electrode according to an embodiment of the present invention. As shown in the drawing, the transparent electrode 1 is a two-layer structure including a nitrogen-containing layer 1a and an electrode layer 1b disposed adjacent to the nitrogen-containing layer 1a. For example, the nitrogen-containing layer 1a and the electrode layer 1b are provided in this order on the top of a substrate 11. In this structure, the electrode layer 1b, which forms an electrode part of the transparent electrode 1, is a layer including silver (Ag) as a main component. The nitrogen-containing layer 1a includes a nitrogen atom (N)-containing compound and is characterized by including a compound having an "effective lone pair" content in the specified range, wherein the "effective lone pair" is defined as the lone pair of a nitrogen atom capable of forming a stable bond with silver, which is a main material used to form the electrode layer 1b. The electrode layer 1b is characterized by including silver (Ag) as a main component and containing at least one of aluminum (Al), gold (Au), indium (In), copper (Cu), palladium (Pd), and platinum (Pt) as an additive element.

Hereinafter, the substrate 11 on which the transparent electrode 1 with such a multilayer structure is provided, and the nitrogen-containing layer 1a and the electrode layer 1b as components of the transparent electrode 1 will be described in detail one by one with respect to their features. As used herein, the term "transparent" for the transparent electrode 1 of the present invention means that the light transmittance at a wavelength of 550 nm is at least 50%.

<Substrate 11>

The substrate 11 on which the transparent electrode 1 of the present invention is formed may be, for example, but not limited to, glass, plastic, or the like. The substrate 11 may be transparent or opaque. The substrate 11 is preferably transparent when the transparent electrode 1 of the present invention is used to form an electronic device in which light is extracted from the substrate 11 side. Glass, quartz, or a transparent resin film is preferably used to form the transparent substrate 11. In particular, the substrate 11 is preferably a resin film, which can impart flexibility to the transparent electrode 1 and an electronic device, such as an organic electroluminescent device, formed therewith.

The glass may be, for example, silica glass, soda lime silica glass, lead glass, borosilicate glass, alkali-free glass, or the like. In view of adhesion to the nitrogen-containing layer 1a, durability, and smoothness, if necessary, the surface of these glass materials may be subjected to a physical process such as polishing, or a coating of an inorganic or organic material or a hybrid coating of a combination thereof may be formed on the surface of these glass materials.

The resin film may be made of, for example, polyester such as polyethylene terephthalate (PET) or polyethylene naphthalate (PEN), polyethylene, polypropylene, cellophane, cellulose esters such as cellulose diacetate, cellulose triacetate (TAC), cellulose acetate butyrate, cellulose acetate propionate (CAP), cellulose acetate phthalate, and cellulose nitrate, or derivatives thereof, polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyether imide, polyether ketone imide, polyamide, fluororesin, nylon, polymethyl methacrylate, acrylic or polyarylate, or cycloolefin resin such as ARTON (trade name, manufactured by JSR Corporation) or APEL (trade name, manufactured by Mitsui Chemicals, Inc.).

A coating of an inorganic or organic material or a hybrid coating of a combination thereof may be formed on the surface of the resin film. Such a coating or hybrid coating is preferably a barrier film (also called barrier coating or the like) having a water-vapor permeability of 0.01 g/(m$^2$·24 hr) or less as measured by the method according to JIS-K-7129-1992 (25±0.5° C., relative humidity 90±2% RH). Such a coating or hybrid coating is more preferably a high barrier film having an oxygen permeability of $10^{-3}$ ml/(m$^2$·24 hr·atm) or less as measured by the method according to JIS-K-7126-1987 and a water-vapor permeability of $10^{-5}$ g/(m$^2$·24 hr) or less.

Such a barrier film may be made of any material having the function of inhibiting the infiltration of water, oxygen, and other substances capable of inducing the degradation of the device. For example, silicon oxide, silicon dioxide, silicon nitride, or the like may be used to form such a barrier film. The barrier film more preferably has a multilayer structure of such an inorganic layer and a layer of an organic material (organic layer) so that the brittleness of the barrier film can be reduced. The inorganic and organic layers may be stacked in any order. Preferably, both are alternately stacked a plurality of times.

The barrier film may be formed using any method such vacuum deposition, sputtering, reactive sputtering, molecular beam epitaxy, ionized-cluster beam technique, ion plating, plasma polymerization, atmospheric pressure plasma polymerization, plasma CVD, laser CVD, thermal CVD, or coating. The atmospheric pressure plasma polymerization described in JP 2004-68143 A is particularly preferred.

On the other hand, when opaque, the substrate 11 may be a substrate of a metal such as aluminum or stainless steel, an opaque resin substrate, a ceramic substrate, or the like. These substrates may be in the form of a flexible film.

<Nitrogen-Containing Layer 1a>

The nitrogen-containing layer 1a, which is provided adjacent to the electrode layer 1b, includes a nitrogen atom (N)-containing compound. This compound is characterized by having an "effective lone pair" content in the specified range, wherein the "effective lone pair" is defined as the lone pair of a nitrogen atom capable of forming a stable bond with silver, which is a main material used to form the electrode layer 1b, among the nitrogen atoms in the compound.

As used herein, the term "effective lone pair" refers to an unshared electron pair that neither contributes to aromaticity nor is coordinated to metal among the unshared electron pairs of the nitrogen atom(s) in the compound. As used herein, the term "aromaticity" refers to an unsaturated cyclic structure having π electron-containing atoms arranged in the form of a ring, what is called aromaticity according to the "Huckel rule," which requires the condition that the number of electrons in the π electron system on the ring is 4n+2, wherein n is 0 or a natural number.

Regardless of whether or not the nitrogen atom having the lone pair is a heteroatom in the aromatic ring, the "effective lone pair" is selected depending on whether or not the lone pair of the nitrogen atom contributes to the aromaticity. For example, even if a certain nitrogen atom is a heteroatom in an aromatic ring, the nitrogen atom can have a lone pair that is not directly involved as an essential component in the aromaticity, in other words, the nitrogen atom can have a lone pair that is not involved as an essential component in imparting aromaticity to the delocalized π electron system on the conjugated unsaturated ring structure (aromatic ring), and such a lone pair can be counted as an "effective lone pair." On the other hand, even if a certain nitrogen atom is not a heteroatom in an aromatic ring, a lone pair of the nitrogen atom can contribute to the aromaticity, and such a lone pair of the nitrogen atom will not be counted as an "effective lone pair." In each compound, the number n of the "effective lone pairs" equals the number of nitrogen atoms with the "effective lone pair."

Next, the "effective lone pair" will be described in detail with reference to specific examples.

Nitrogen is a Group 15 element having five peripheral electrons. Among them, three unpaired electrons are used to form covalent bonds with other atoms, and the other two electrons form a lone pair. In general, therefore, a nitrogen atom forms three bonds.

Examples of nitrogen atom-containing groups include an amino group (—NR$^1$R$^2$), an amide group (—C(=O)NR$^1$R$^2$), a nitro group (—NO$_2$), a cyano group (—CN), a diazo group (—N$_2$), an azido group (—N$_3$), a urea bond (—NR$^1$C=ONR$^2$—), an isothiocyanate group (—N=C=S), a thioamido group (—C(=S)NR$^1$R$^2$), etc. R$^1$ and R$^2$ are each a hydrogen atom (H) or a substituent. The lone pair of the nitrogen atom in these groups neither contributes to aromaticity nor is coordinated to metal and thus corresponds to the "effective lone pair." Among them, the lone pair of the nitrogen atom in a nitro group (—NO$_2$) is considered to exist as an "effective lone pair" neither contributing to aromaticity nor being coordinated to metal because it can produce a good effect as shown in Examples below although it is used to form the resonance structure with oxygen atoms.

Figure 2:
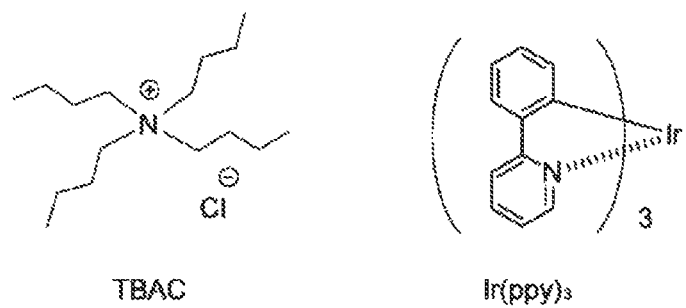
FIG. 2 is a diagram showing the structure of TBAC and Ir(ppy)$_3$ for illustrating nitrogen atom bonding.

A nitrogen atom can also form a forth bond by using the lone pair. An example of this case will be described with reference to FIG. 2. FIG. 2 shows the structural formulae of tetrabutylammonium chloride (TBAC) and tris(2-phenylpyridine) iridium (III) [Ir(ppy)$_3$].

Among them, TBAC is a quaternary ammonium salt having four butyl groups, one of which forms an ionic bond with the nitrogen atom, and a chloride ion as the counter ion. In this case, one of the electrons of the lone pair of the nitrogen atom is donated to the ionic bond with the butyl groups. Therefore, the nitrogen atom of TBAC is deemed not to have any lone pair in the first place. Thus, the lone pair of the nitrogen atom in TBAC does not correspond to the "effective lone pair" neither contributing to aromaticity nor being coordinated to metal.

Ir(ppy)$_3$ is a metal complex having a nitrogen atom coordinately bonded to an iridium atom. The lone pair of the nitrogen atom in Ir(ppy)$_3$ is coordinated to the iridium atom and used to form the coordinate bond. Therefore, the lone pair of the nitrogen atom in Ir(ppy)$_3$ also does not correspond to the "effective lone pair" neither contributing to aromaticity nor being coordinated to metal.

A nitrogen atom is a common heteroatom capable of forming an aromatic ring and contributing to the development of aromaticity. Examples of the nitrogen-containing aromatic ring include a pyridine ring, a pyrazine ring, a pyrimidine ring, a triazine ring, a pyrrole ring, an imidazole ring, a pyrazole ring, a triazole ring, a tetrazole ring, etc.

Figure 3:
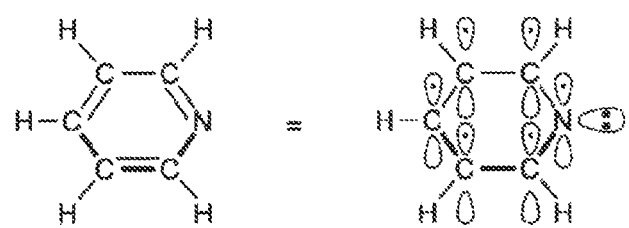
FIG. 3 is a diagram showing the structural formula and molecular orbital of a pyridine ring.

FIG. 3 is a diagram showing the structural formula and molecular orbital of a pyridine ring, one of the groups listed above. As shown in FIG. 3, the pyridine ring forms a 6-membered conjugated (resonance) unsaturated ring structure having six delocalized π electrons, which meets the 4n+2 (n=0 or a natural number) Huckel rule. The nitrogen atom in the 6-membered ring is substituted for —CH=. Therefore, only one unpaired electron is used for the 6 π electron system, and the lone pair is not involved as an essential component in the development of the aromaticity.

Thus, the lone pair of the nitrogen atom in the pyridine ring corresponds to the "effective lone pair" neither contributing to aromaticity nor being coordinated to metal.

Figure 4:
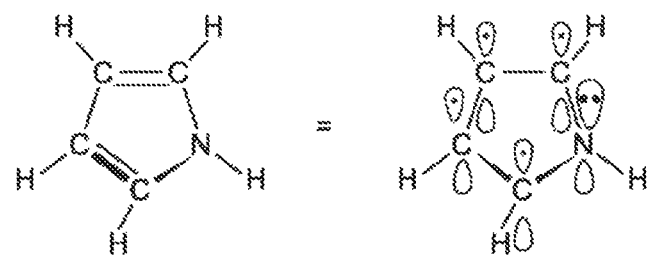
FIG. 4 is a diagram showing the structural formula and molecular orbital of a pyrrole ring.

FIG. 4 is a diagram showing the structural formula and molecular orbital of a pyrrole ring. As shown in FIG. 4, the pyrrole ring is a structure having a nitrogen atom substituted for one of 5-membered ring-forming carbon atoms and also having six π electrons, which means that it is a nitrogen-containing aromatic ring satisfying the Huckel rule. Since the nitrogen atom of the pyrrole ring is also bonded to a hydrogen atom, the lone pair is used for the 6 π electron system.

Therefore, although the nitrogen atom of the pyrrole ring has a lone pair, the lone pair is used as an essential component for the development of the aromaticity and thus does not correspond to the "effective lone pair" neither contributing to aromaticity nor being coordinated to metal.

Figure 5:
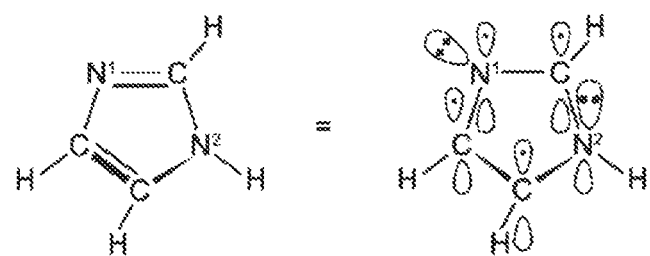
FIG. 5 is a diagram showing the structural formula and molecular orbital of an imidazole ring.

FIG. 5 is a diagram showing the structural formula and molecular orbital of an imidazole ring. As shown in FIG. 5, the imidazole ring has a structure containing two nitrogen atoms N$^1$ and N$^2$ substituted at positions 1 and 3 of a 5-membered ring and is also a nitrogen-containing aromatic ring having 6 π electrons. Among them, one nitrogen atom N$^1$ gives only one unpaired electron to the 6 π electron system, which means that the nitrogen atom is of a pyridine ring type, in which the lone pair is not used for the development of aromaticity. Therefore, the lone pair of the nitrogen atom N$^1$ corresponds to the "effective lone pair." In contrast, the other nitrogen atom N$^2$ is of a pyrrole ring type, in which the lone pair is used for the 6 π electron system. Therefore, the lone pair of the nitrogen atom N$^2$ does not correspond to the "effective lone pair."

Therefore, although the imidazole ring has two nitrogen atoms N$^1$ and N$^2$, the lone pair of only one nitrogen atom N$^1$ corresponds to the "effective lone pair."

The above-described selection of the lone pair of a nitrogen atom in a "nitrogen-containing aromatic ring" also applies in the same way to any condensed ring compound having a nitrogen-containing aromatic ring skeleton.

Figure 6:
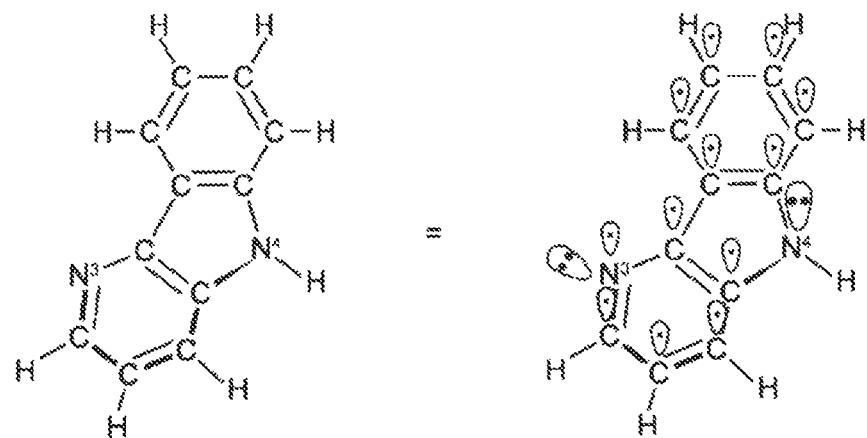
FIG. 6 is a diagram showing the structural formula and molecular orbital of a 5-carboline ring.

FIG. 6 is a diagram showing the structural formula and molecular orbital of a δ-carboline ring. As shown in FIG. 6, the δ-carboline ring is a condensed ring compound having a nitrogen-containing aromatic ring skeleton, in which a benzene ring skeleton, a pyrrole ring skeleton, and a pyridine ring skeleton are condensed in this order to form an azacarbazole compound. In this structure, the nitrogen atom N$^3$ of the pyridine ring gives only one unpaired electron to the π electron system, while the nitrogen atom N$^4$ of the pyrrole ring gives a lone pair to the π electron system. The aromatic ring has 14 π electrons in total, including 11 π electrons from the carbon atoms of the ring.

Therefore, among the two nitrogen atoms N$^3$ and N$^4$ of the δ-carboline ring, the lone pair of the nitrogen atom N$^3$ in the pyridine ring corresponds to the "effective lone pair," but the lone pair of the nitrogen atom N$^4$ in the pyrrole ring does not correspond to the "effective lone pair."

As shown above, the lone pair of a nitrogen atom in a condensed ring compound is also involved in bonding, as in a single ring such as a pyridine or pyrrole ring, which forms the condensed ring compound.

The "effective lone pair" described above is important to produce a strong interaction with silver as a main component of the electrode layer 1b. In view of stability and durability, the nitrogen atom having such an "effective lone pair" is preferably present in a nitrogen-containing aromatic ring. Therefore, the compound in the nitrogen-containing layer 1a preferably has an aromatic heterocyclic ring containing an effective lone pair-bearing nitrogen atom as a heteroatom.

Specifically, in this embodiment, for example, the effective lone pair content [n/M] is defined as the ratio of the number n of "effective lone pairs" to the molecular weight M of such a compound. The nitrogen-containing layer 1a is also characterized by including a compound that is so selected that it satisfies the relation $2.0 \times 10^{-3} \leq [n/M]$. The nitrogen-containing layer 1a is preferably such that its effective lone pair content [n/M], defined as stated above, is in the range of $3.9 \times 10^{-3}$ or more ($3.9 \times 10^{-3} \leq [n/M]$), more preferably such that its effective lone pair content [n/M] is in the range of $6.5 \times 10^{-3}$ or more ($6.5 \times 10^{-3} \leq [n/M]$).

The nitrogen-containing layer 1a only has to include a compound whose effective lone pair content [n/M] is in the specified range. The nitrogen-containing layer 1a may be composed of only such a compound, or a mixture of such a compound and an additional compound may be used to form the nitrogen-containing layer 1a. The additional compound does not need to contain any nitrogen atom and does not need to have an effective lone pair content [n/M] in the specified range.

When the nitrogen-containing layer 1a includes a plurality of compounds, the molecular weight M of the mixture of these compounds may be calculated, for example, based on the mixing ratio of the compounds, and the ratio of the total number n of "effective lone pairs" to the molecular weight M may be calculated as an average effective lone pair content [n/M]. This value is preferably in the specified range. In other words, the nitrogen-containing layer 1a itself preferably has an effective lone pair content [n/M] in the specified range.

When the nitrogen-containing layer 1a includes a plurality of compounds, the mixing ratio (content) of the compounds may vary in the thicknesswise direction of the layer. In this case, a surface part of the nitrogen-containing layer 1a on the side in contact with the electrode layer 1b should have an effective lone pair content [n/M] in the specified range.

[Compound 1]

Hereinafter, examples (Nos. 1 to 48) of the compound whose effective lone pair content [n/M] satisfies $2.0 \times 10^{-3} \leq [n/M]$ will be shown, which may each be used to form the nitrogen-containing layer 1a. In each of compounds Nos. 1 to 48, the nitrogen atom having an "effective lone pair" is marked by a circle. Table 1 below shows the molecular weight M of compound Nos. 1 to 48, the number n of "effective lone pairs" in each of the compounds, and the effective lone pair content [n/M] of each compound. In compound No. 33 shown below, copper phthalocyanine, lone pairs that are not coordinated to copper are counted as "effective lone pairs" among the lone pairs of the nitrogen atoms.

[Chemical Formula 14]

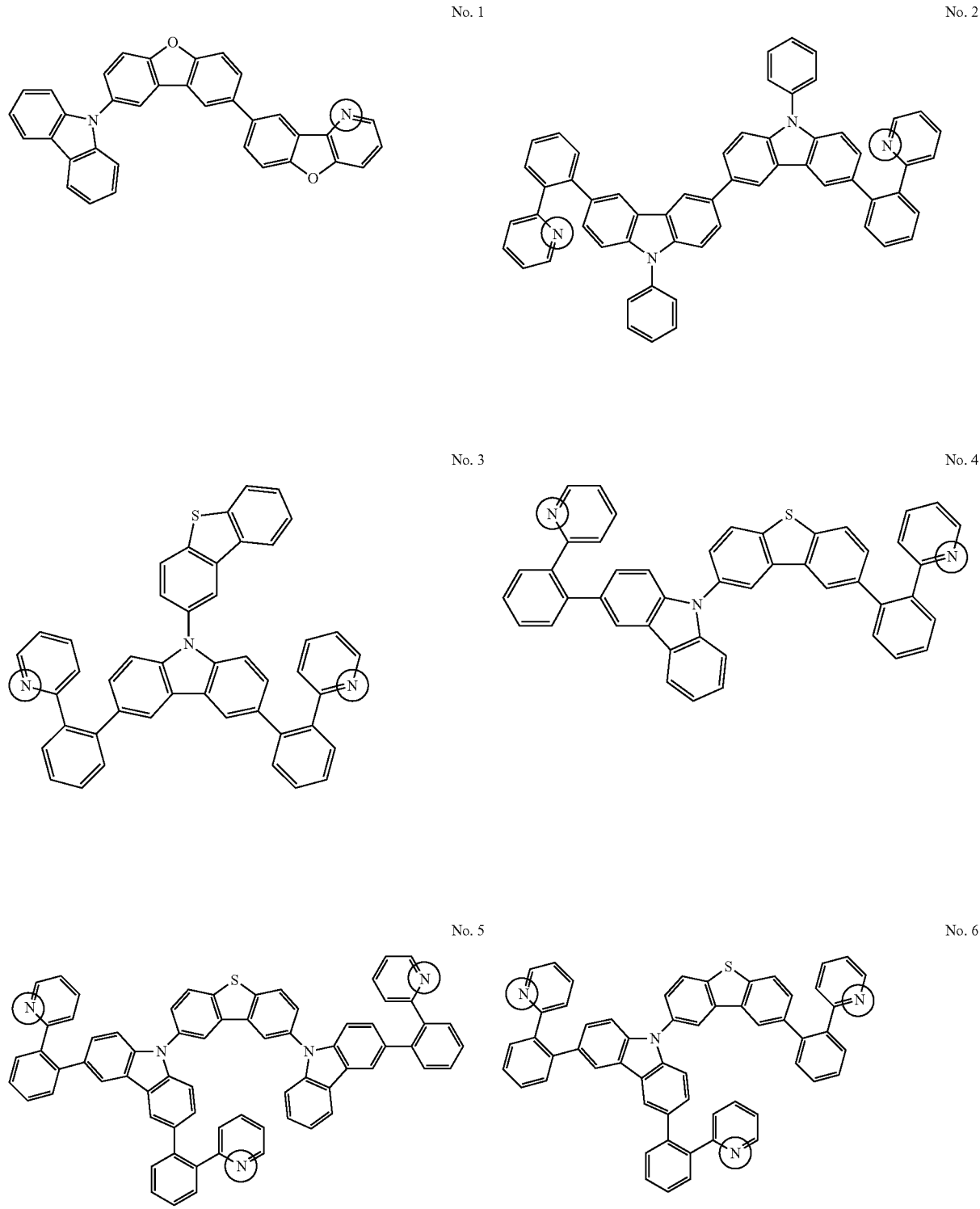

-continued
No. 7
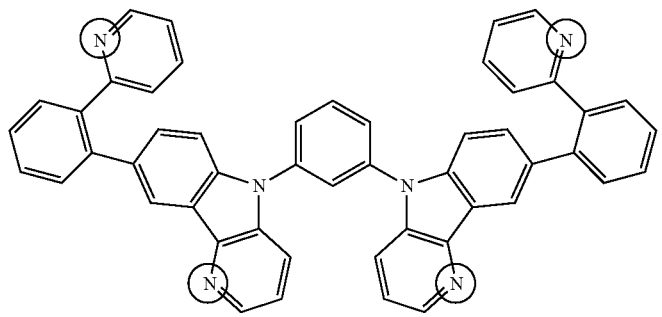
[Chemical Formula 15]
No. 8
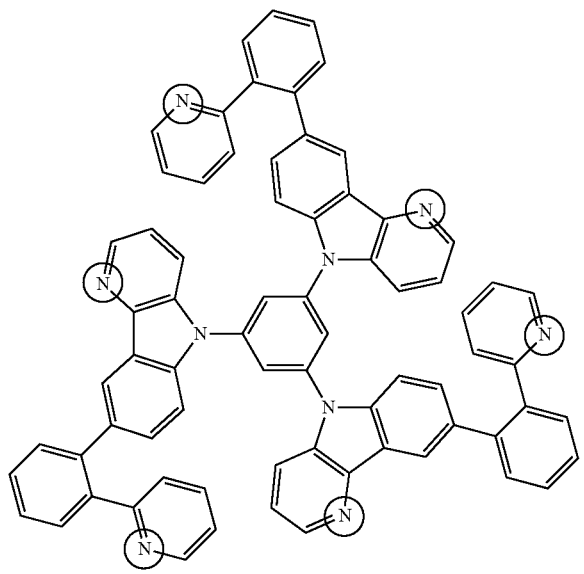
No. 9
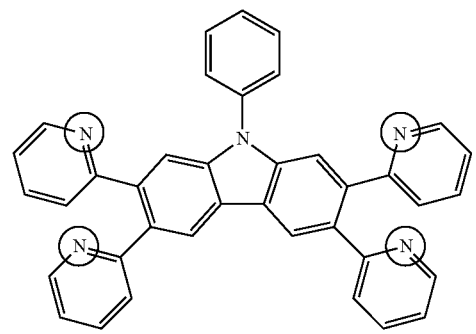
No. 10
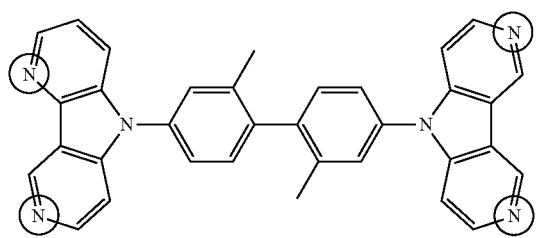
No. 11
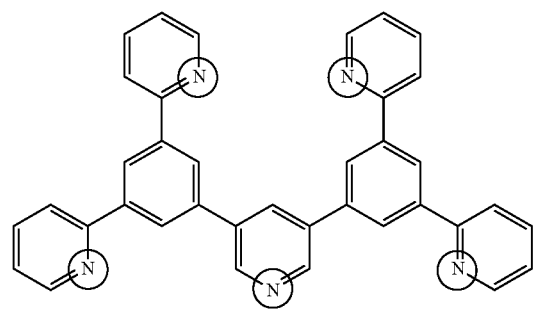
No. 12
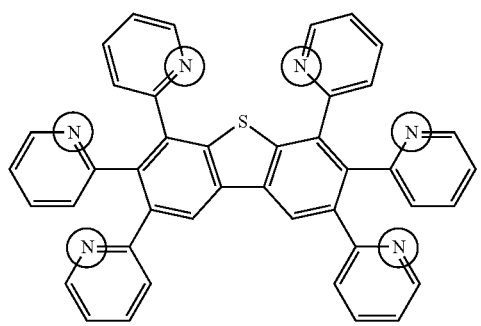
No. 13
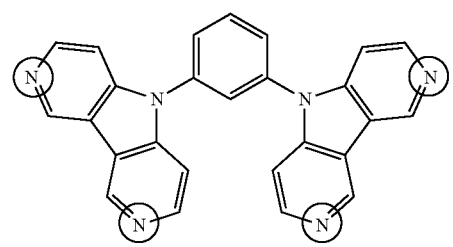

-continued
No. 14
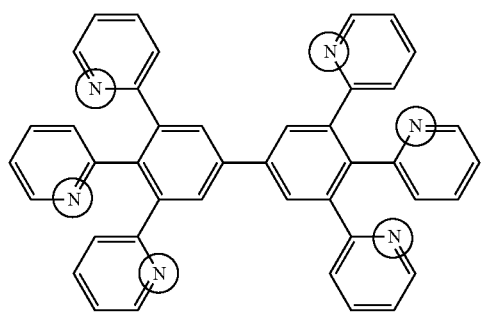
No. 15
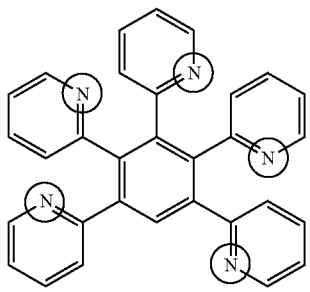
No. 16
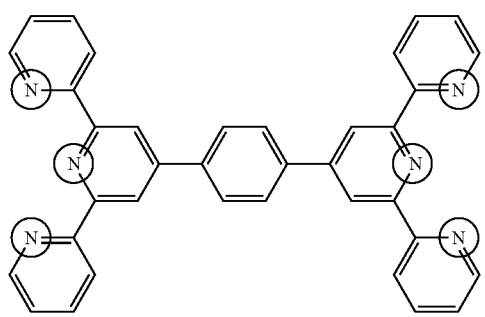
[Chemical Formula 16]
No. 17
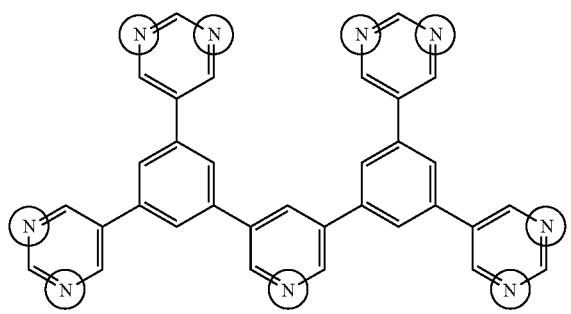
No. 18
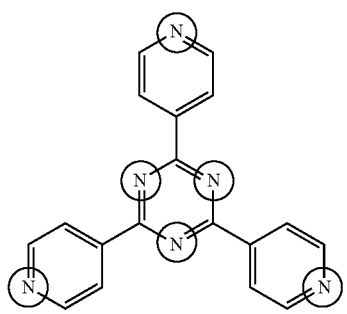
No. 19
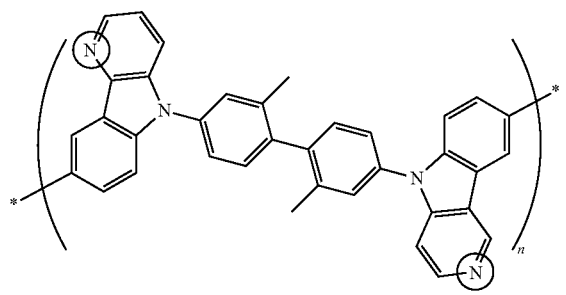
No. 20
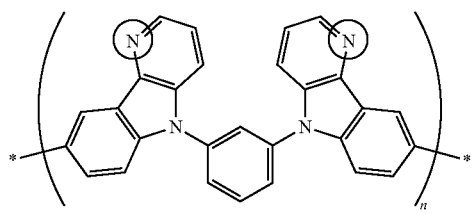

-continued
No. 21
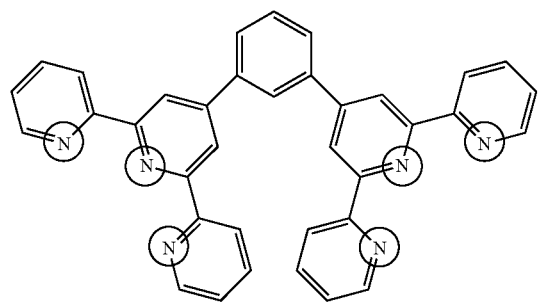
No. 22
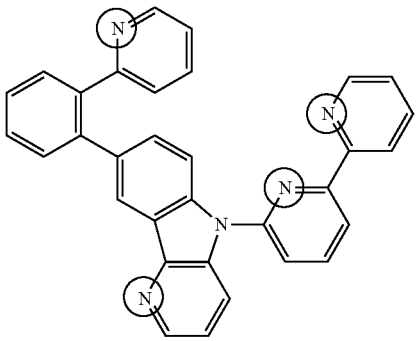
No. 23
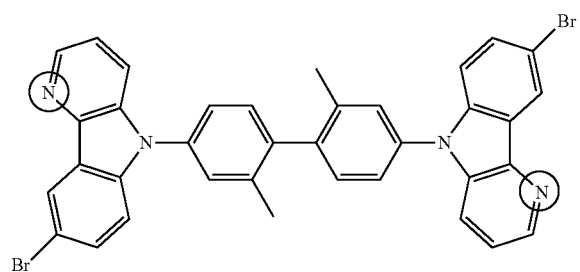
No. 24
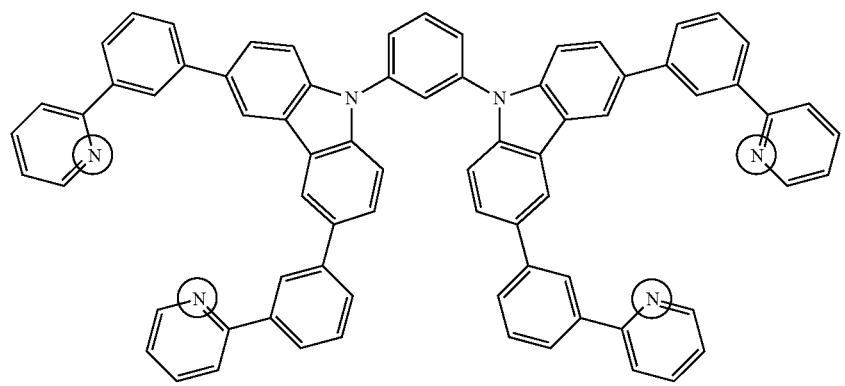
No. 25
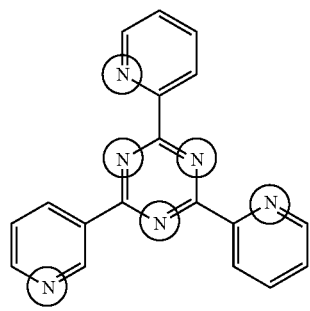
[Chemical Formula 17]
No. 26
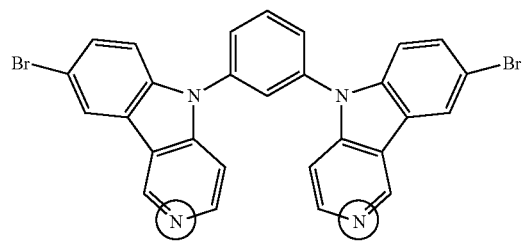
No. 27
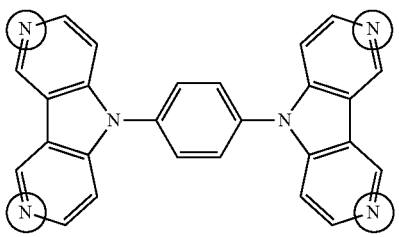

-continued
No. 28
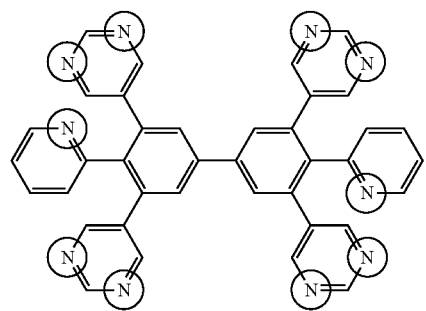
No. 29
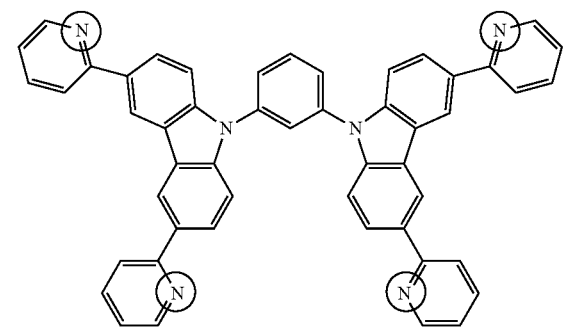
No. 30
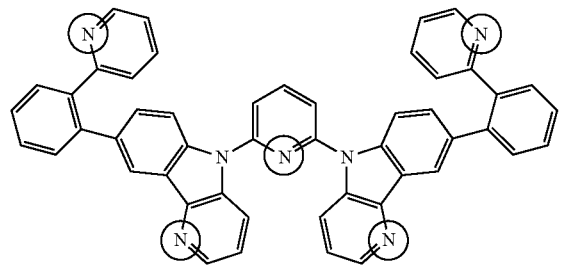
No. 31
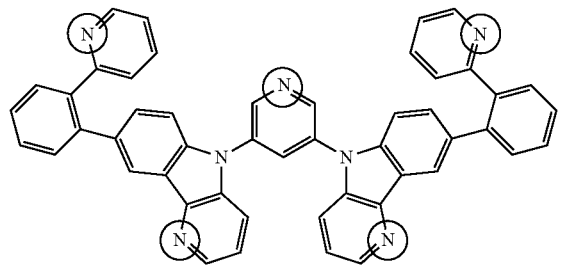
No. 32
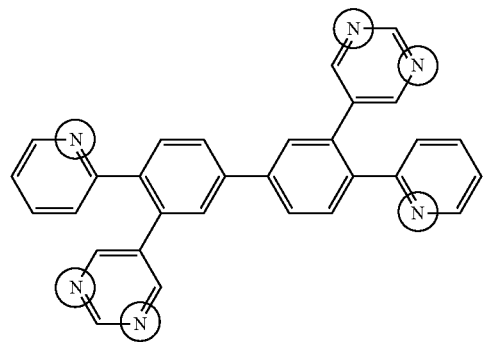
No. 33
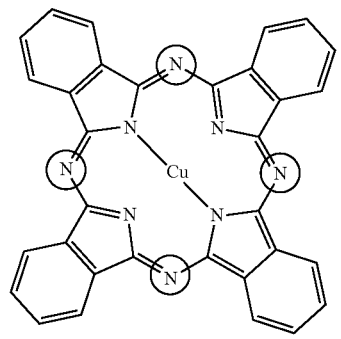
No. 34
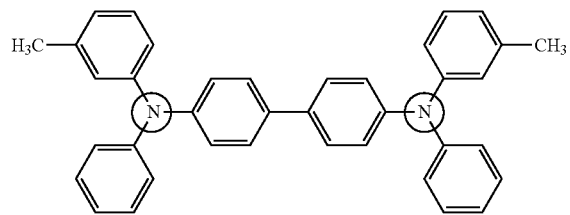
No. 35
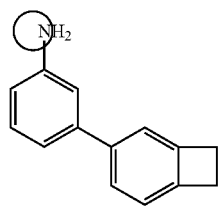

[Chemical Formula 18]
No. 36
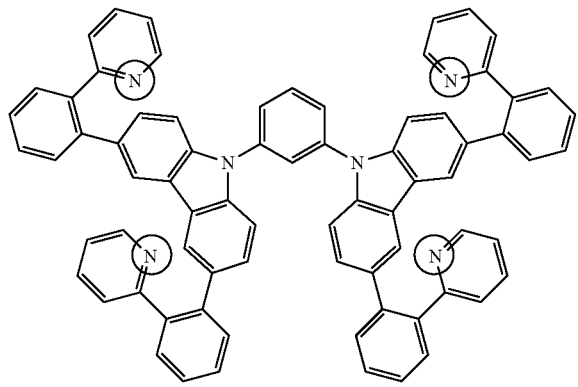
No. 37
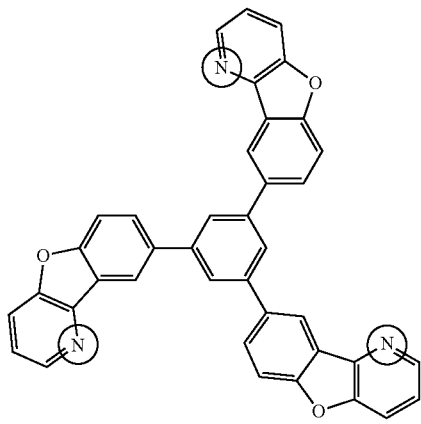
No. 38
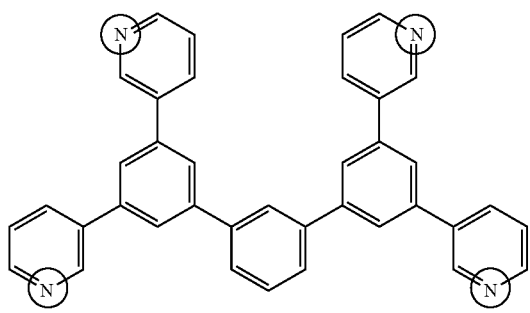
No. 39
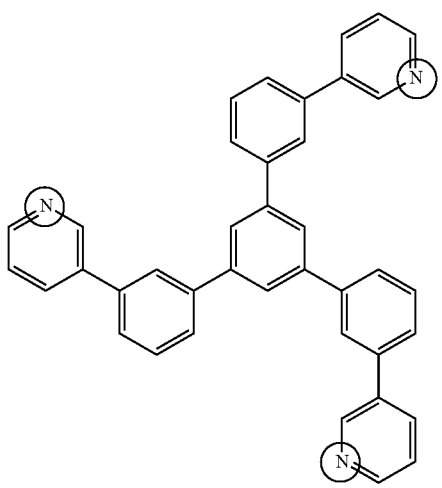
No. 40
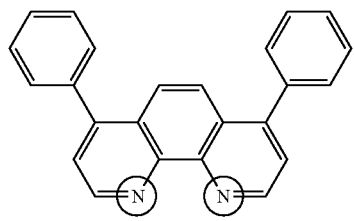
No. 41
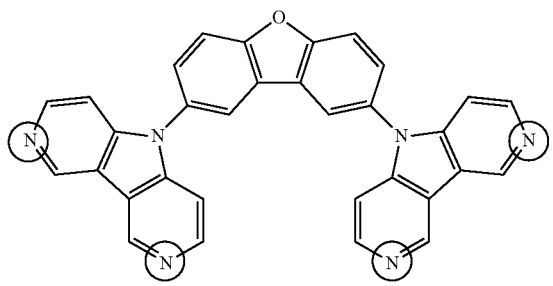

[Chemical Formula 19]
No. 42
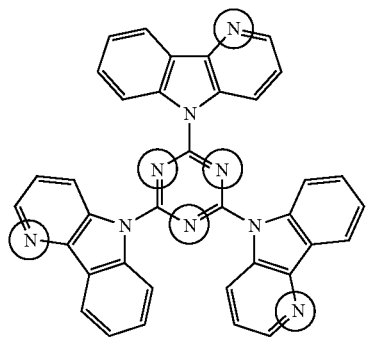
No. 43
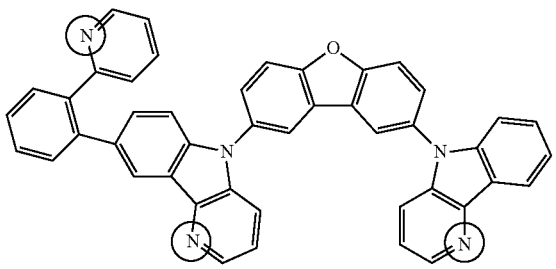
No. 44
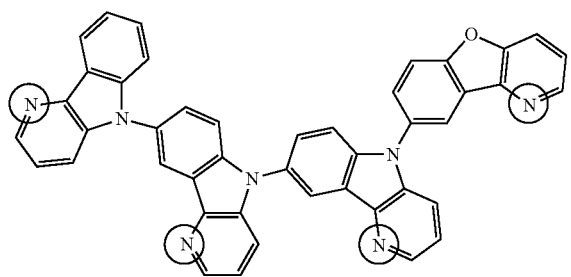
No. 45
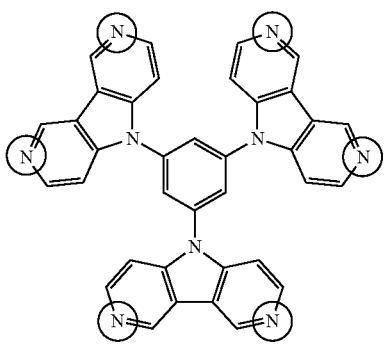
No. 46
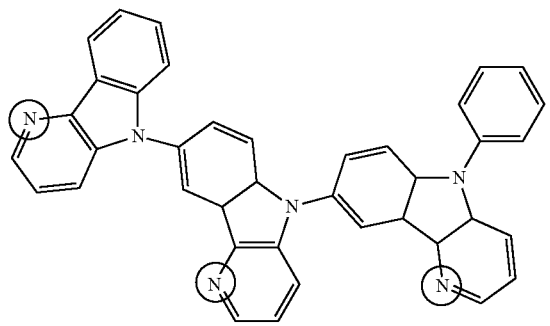
No. 47
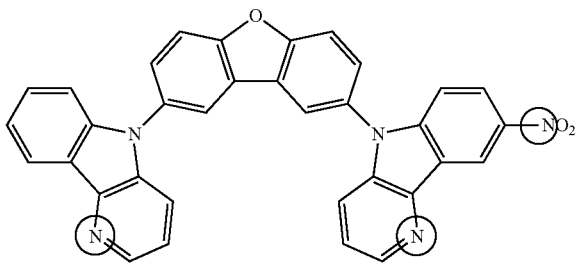
No. 48
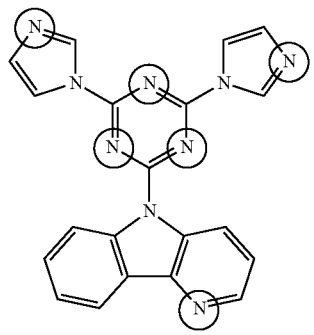

TABLE 1

| Compound | Number [n] of effective lone pairs | Molecular weight [M] | [n/M] | Corresponding formula |
|---|---|---|---|---|
| No. 1 | 1 | 500.55 | 2.0E−03 | (1b) |
| No. 2 | 2 | 790.95 | 2.5E−03 | |
| No. 3 | 2 | 655.81 | 3.0E−03 | |
| No. 4 | 2 | 655.81 | 3.0E−03 | |
| No. 5 | 3 | 974.18 | 3.1E−03 | (2) |
| No. 6 | 3 | 808.99 | 3.7E−03 | |
| No. 7 | 4 | 716.83 | 5.6E−03 | (1a-1), (2) |
| No. 8 | 6 | 1036.19 | 5.8E−03 | (1a-1), (4) |
| No. 9 | 4 | 551.64 | 7.3E−03 | |
| No. 10 | 4 | 516.60 | 7.7E−03 | (1a-2), (3) |
| No. 11 | 5 | 539.63 | 9.3E−03 | |
| No. 12 | 6 | 646.76 | 9.3E−03 | (5) |
| No. 13 | 4 | 412.45 | 9.7E−03 | (1a-2), (3) |
| No. 14 | 6 | 616.71 | 9.7E−03 | (5) |
| No. 15 | 5 | 463.53 | 1.1E−02 | (2) |
| No. 16 | 6 | 540.62 | 1.1E−02 | (6) |
| No. 17 | 9 | 543.58 | 1.7E−02 | |
| No. 18 | 6 | 312.33 | 1.9E−02 | |
| No. 19 | 2 | 512.60 | 3.9E−03 | (1a-1) |
| No. 20 | 2 | 408.45 | 4.9E−03 | (1a-1) |
| No. 21 | 6 | 540.62 | 1.1E−02 | (6) |
| No. 22 | 4 | 475.54 | 8.4E−03 | (1a-1) |
| No. 23 | 2 | 672.41 | 3.0E−03 | (1a-1) |
| No. 24 | 4 | 1021.21 | 3.9E−03 | |
| No. 25 | 6 | 312.33 | 1.9E−02 | (6) |
| No. 26 | 2 | 568.26 | 3.5E−03 | (1a) |
| No. 27 | 4 | 412.45 | 9.7E−03 | (1a-2), (3) |
| No. 28 | 10 | 620.66 | 1.6E−02 | (5) |
| No. 29 | 4 | 716.83 | 5.6E−03 | |
| No. 30 | 5 | 717.82 | 7.0E−03 | (1a-1), (2) |
| No. 31 | 5 | 717.82 | 7.0E−03 | (1a-1), (2) |
| No. 32 | 6 | 464.52 | 1.3E−02 | |
| No. 33 | 4 | 576.10 | 6.9E−03 | |
| No. 34 | 2 | 516.67 | 3.9E−03 | |
| No. 35 | 1 | 195.26 | 5.1E−03 | |
| No. 36 | 4 | 1021.21 | 3.9E−03 | (2) |
| No. 37 | 3 | 579.60 | 5.2E−03 | (1b) |
| No. 38 | 4 | 538.64 | 7.4E−03 | |
| No. 39 | 3 | 537.65 | 5.6E−03 | |
| No. 40 | 2 | 332.40 | 6.0E−03 | |
| No. 41 | 4 | 502.15 | 8.0E−03 | (1a-2), (3) |
| No. 42 | 6 | 579.19 | 1.0E−02 | (1a-1) |
| No. 43 | 3 | 653.22 | 4.6E−03 | (1a-1) |
| No. 44 | 4 | 667.21 | 6.0E−03 | (1a-1), (1b) |
| No. 45 | 6 | 579.19 | 1.0E−02 | (1a-2), (3) |
| No. 46 | 3 | 576.65 | 5.2E−03 | (1a-1) |
| No. 47 | 3 | 545.55 | 5.5E−03 | (1a-1) |
| No. 48 | 6 | 379.38 | 1.6E−02 | (1a-2), (7), (8a) |

Table 1 shows corresponding formulae, which are used when the illustrative compounds also belong to the additional compound II group represented by formulae (1) to (8a) shown below.

[Compound II]

Besides the compound having an effective lone pair content [n/M] in the specified range, the nitrogen-containing layer 1a may also include an additional compound. Such an additional compound used to form the nitrogen-containing layer 1a is preferably a nitrogen atom-containing compound regardless of whether or not it has an effective lone pair content [n/M] in the specified range. In particular, a compound containing an effective lone pair-bearing nitrogen atom is preferably used. The additional compound used to form the nitrogen-containing layer 1a may be a compound having the properties necessary for each electronic device to be formed with the transparent electrode 1 having the nitrogen-containing layer 1a. For example, when the transparent electrode 1 is used as an electrode for an organic electroluminescent device, a compound having a structure represented by any of formulae (1) to (8a) shown below is preferably used to form the nitrogen-containing layer 1a in view of the film formability or electron transport properties.

The compounds having structures represented by formulae (1) to (8a) also include compounds having an effective lone pair content [n/M] in the specified range. Such compounds may be used alone to form the nitrogen-containing layer 1a (see Table 1 above). On the other hand, the compounds having structures represented by formulae (1) to (8a) also include compounds having an effective lone pair content [n/M] out of the specified range. Any of such compounds may be mixed with a compound having an effective lone pair content [n/M] in the specified range to form the nitrogen-containing layer 1a.

[Chemical Formula 20]

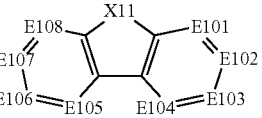

Formula (1)

In formula (1), X11 represents —N(R11)- or —O—. In formula (1), E101 to E108 each represent —C(R12)= or —N=. At least one of E101 to E108 is —N=. R11 and R12 each represent a hydrogen atom (H) or a substituent.

The substituent may be, for example, alkyl (e.g., methyl, ethyl, propyl, isopropyl, tert-butyl, pentyl, pentyl, hexyl, octyl, dodecyl, tridecyl, tetradecyl, or pentadecyl), cycloalkyl (e.g., cyclopentyl or cyclohexyl), alkenyl (e.g., vinyl or allyl), alkynyl (e.g., ethynyl or propargyl), an aromatic hydrocarbon group (also called an aromatic carbon ring group, aryl group, or the like, e.g., phenyl, p-chlorophenyl, mesityl, tolyl, xylyl, naphthyl, anthryl, azulenyl, acenaphthenyl, fluorenyl, phenanthryl, indenyl, pyrenyl, or biphenylyl), an aromatic heterocyclic group (e.g., furyl, thienyl, pyridyl, pyridazinyl, pyrimidinyl, pyrazinyl, triazinyl, imidazolyl, pyrazolyl, thiazolyl, quinazolinyl, carbazolyl, carbolinyl, diazacarbazolyl (referring to a moiety derived from the carbolinyl by replacing any one of carbon atoms in the carboline ring with a nitrogen atom), or phthalazinyl), a heterocyclic group (e.g., pyrrolidyl, imidazolidyl, morpholinyl, or oxazolidyl), alkoxy (e.g., methoxy, ethoxy, propyloxy, pentyloxy, hexyloxy, octyloxy, or dodecyloxy), cycloalkoxy (e.g., cyclopentyloxy or cyclohexyloxy), aryloxy (e.g., phenoxy or naphthyloxy), alkylthio (e.g., methylthio, ethylthio, propylthio, pentylthio, hexylthio, octylthio, or dodecylthio), cycloalkylthio (e.g., cyclopentylthio or cyclohexylthio), arylthio (e.g., phenylthio or naphthylthio), alkoxycarbonyl (e.g., methyloxycarbonyl, ethyloxycarbonyl, butyloxycarbonyl, octyloxycarbonyl, or dodecyloxycarbonyl), aryloxycarbonyl (e.g., phenyloxycarbonyl or naphthyloxycarbonyl), sulfamoyl (e.g., aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, or 2-pyridylaminosulfonyl), acyl (e.g., acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, or pyridylcarbonyl), acyloxy (e.g., acetyloxy, ethylcarbonyloxy, butylcarbonyloxy, octylcarbonyloxy, dodecylcarbonyloxy, or phenylcarbonyloxy), amido (e.g., methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, dodecylcarbonylamino, phenylcarbonylamino, or naphthylcarbonylamino), carbamoyl (e.g., aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, or 2-pyridylaminocarbonyl), ureido (e.g., methylureido, ethylureido, pentylureido, cyclohexylureido, octylureido, dodecylureido, phenylureido, naphthylureido, or 2-pyridylaminoureido), sulfinyl (e.g., methylsulfinyl, ethylsulfinyl, butylsulfinyl, cyclohexylsulfinyl, 2-ethylhexylsulfinyl, dodecylsulfinyl, phenylsulfinyl, naphthylsulfinyl, or 2-pyridylsulfinyl), alkylsulfonyl (e.g., methylsulfonyl, ethylsulfonyl, butylsulfonyl, cyclohexylsulfonyl, 2-ethylhexylsulfonyl, or dodecylsulfonyl), arylsulfonyl or heteroarylsulfonyl (e.g., phenylsulfonyl, naphthylsulfonyl, or 2-pyridylsulfonyl), amino (e.g., amino, ethylamino, dimethylamino, butylamino, cyclopentylamino, 2-ethylhexylamino, dodecylamino, anilino, naphthylamino, 2-pyridylamino, piperidyl (also called piperidinyl), or 2,2,6,6-tetramethylpiperidinyl), a halogen atom (e.g., fluorine atom, chlorine atom, or bromine atom), a fluorinated hydrocarbon group (e.g., fluoromethyl, trifluoromethyl, pentafluoroethyl, or pentafluorophenyl), cyano, nitro, hydroxy, mercapto, silyl (e.g., trimethylsilyl, triisopropylsilyl, triphenylsilyl, or phenyldiethylsilyl), a phosphate group (e.g., dihexylphosphoryl), a phosphite group (e.g., diphenylphosphinyl), phosphono, or the like.

Part of any of these substituents may be further substituted with any of these substituents. Two or more occurrences of any of these substituents may also be linked together to form a ring. Among these substituents, substituents that do not inhibit the interaction between the compound and silver (Ag) are preferably used, and in particular, substituents having the effective lone pair-bearing nitrogen atom are preferably used. The above statement about substituents also applies to the substituents shown in the description of formulae (2) to (8a) below.

The compound having a structure represented by formula (1) is preferred because a strong interaction can be produced between the nitrogen atom in the compound and silver in the electrode layer 1b.

[Chemical Formula 21]

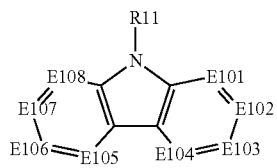

Formula (1a)

The compound having a structure represented by formula (1a) is one type of the compound having the structure of formula (1), in which —N(R11)- corresponds to X11 in formula (1). This compound is preferred because it can more strongly produce the interaction.

[Chemical Formula 22]

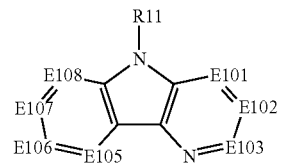

Formula (1a-1)

The compound having a structure represented by formula (1a-1) is one type of the compound having the structure of formula (1a), in which —N= corresponds to E104 in formula (1a). This compound is preferred because it can more effectively produce the interaction.

[Chemical Formula 23]

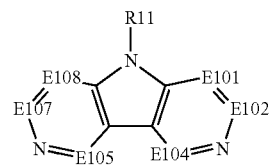

Formula (1a-2)

The compound having a structure represented by formula (1a-2) is another type of the compound having the structure of formula (1a), in which —N= corresponds to E103 and E106 in formula (1a), respectively. This compound is preferred because it has more nitrogen atoms and thus can more strongly produce the interaction.

[Chemical Formula 24]

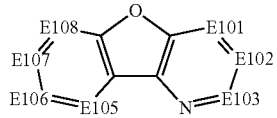

Formula (1b)

The compound having a structure represented by formula (1b) is one type of the compound having the structure of formula (1), in which —O— and —N= correspond to X11 and E104 in formula (1), respectively. This compound is preferred because it can more effectively produce the interaction.

Compounds having the structures represented by formulae (2) to (8a) below, respectively, are also preferred because they can more effectively produce the interaction.

[Chemical Formula 25]

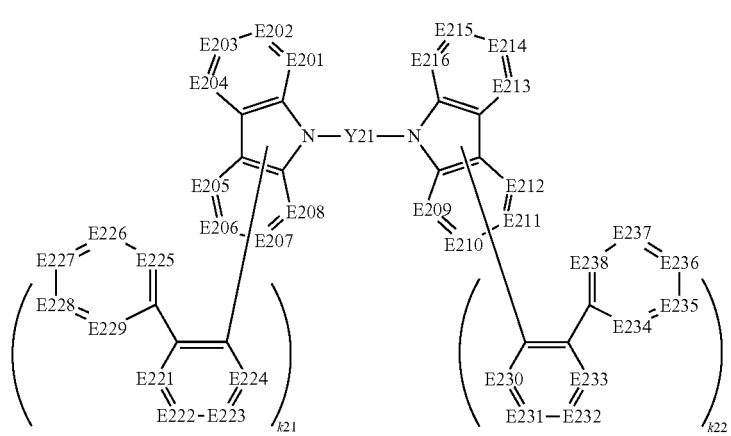

Formula (2)

Formula (2) is also one type of formula (1). In formula (2), Y21 represents an arylene group, a heteroarylene group, or a divalent linking group including a combination thereof. E201 to E216 and E221 to E238 each represent —C(R21)= or —N=. R21 represents a hydrogen atom (H) or a substituent. At least one of E221 to E229 and at least one of E230 to E238 represent —N=, and k21 and k22 each represent an integer of 0 to 4, provided that k21+k22 is an integer of 2 or more.

In formula (2), the arylene group represented by Y21 may be, for example, o-phenylene, p-phenylene, naphthalenediyl, anthracenediyl, naphthacenediyl, pyrenediyl, naphthylnaphthalenediyl, biphenyldiyl (e.g., [1,1'-biphenyl]-4,4'-diyl, 3,3'-biphenyldiyl, or 3,6-biphenyldiyl), terphenyldiyl, quaterphenyldiyl, quinquephenyldiyl, sexiphenyldiyl, septiphenyldiyl, octiphenyldiyl, noviphenyldiyl, deciphenyldiyl, or the like.

In formula (2), the heteroarylene group represented by Y21 may be, for example, a divalent group derived from at least one selected from the group consisting of a carbazole ring, a carboline ring, a diazacarbazole ring (also called a monoazacarboline ring, which is a ring structure derived from a carboline ring by replacing a carbon atom in the carboline ring with a nitrogen atom), a triazole ring, a pyrrole ring, a pyridine ring, a pyrazine ring, a quinoxaline ring, a thiophene ring, an oxadiazole ring, a dibenzofuran ring, a dibenzothiophene ring, and an indole ring.

Preferred modes of the arylene group, the heteroarylene group, or the divalent linking group including a combination thereof, represented by Y21, are preferably as follows. The heteroarylene group preferably includes a group derived from a condensed aromatic heterocyclic ring formed by condensation of three or more rings. The group derived from a condensed aromatic heterocyclic ring formed by condensation of three or more rings is preferably a group derived from a dibenzofuran ring or a dibenzothiophene ring.

In formula (2), six or more of E201 to E208 and six or more of E209 to E216 each preferably represent —C(R21)=.

In formula (2), at least one of E225 to E229 and at least one of E234 to E238 preferably represent —N=.

In formula (2), any one of E225 to E229 and any one of E234 to E238 preferably represent —N=.

In formula (2), E221 to E224 and E230 to E233 each preferably represent —C(R21)=.

In the compound represented by formula (2), E203 preferably represents —C(R21)=, R21 preferably represents a linking moiety, E211 also preferably represents —C(R21)=, and R21 preferably represents a linking moiety.

E225 and E234 also preferably represent —N=, and E221 to E224 and E230 to E233 each preferably represent —C(R21)=.

[Chemical Formula 26]

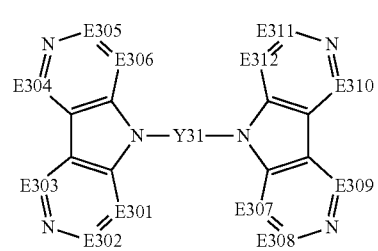

Formula (3)

Formula (3) is also one type of formula (1a-2). In formula (3), E301 to E312 each represent —C(R31)=, wherein R31 represents a hydrogen atom (H) or a substituent. Y31 represents an arylene group, a heteroarylene group, or a divalent linking group including a combination thereof.

Preferred modes of the arylene group, the heteroarylene group, or the divalent linking group including a combination thereof, represented by Y31 in formula (3), may be the same as those for Y21 in formula (2).

[Chemical Formula 27]

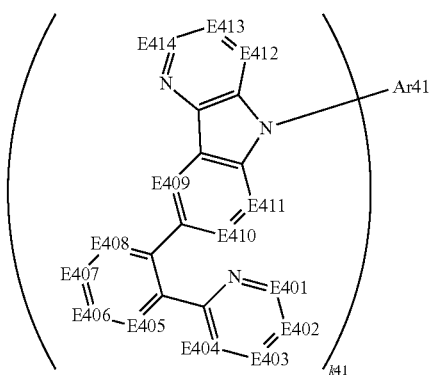

Formula (4)

Formula (4) is also one type of formula (1a-1). In formula (4), E401 to E414 each represent —C(R41)=, wherein R41 is a hydrogen atom (H) or a substituent. Ar41 represents a substituted or unsubstituted aromatic hydrocarbon ring or aromatic heterocyclic ring, and k41 represents an integer of 3 or more.

In formula (4), Ar41 may represent an aromatic hydrocarbon ring. In this case, the aromatic hydrocarbon ring may be a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthene ring, a naphthacene ring, a pentacene ring, a perylene ring, a pentaphene ring, a picene ring, a pyrene ring, a pyranthrene ring, an anthanthrene ring, or the like. These rings may further have any of the substituents listed for R11 and R12 in formula (1).

In formula (4), Ar41 may represent an aromatic heterocyclic group. In this case, the aromatic heterocyclic group may be a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a triazole ring, an indole ring, a benzimidazole ring, a benzothiazole ring, a benzoxazole ring, a quinoxaline ring, a quinazoline ring, a phthalazine ring, a carbazole ring, an azacarbazole ring, or the like. The azacarbazole ring refers to a ring derived from a carbazole ring by replacing a carbon atom(s) in the benzene ring of the carbazole ring with at least one nitrogen atom. These rings may further have any of the substituents listed for R11 and R12 in formula (1).

[Chemical Formula 28]

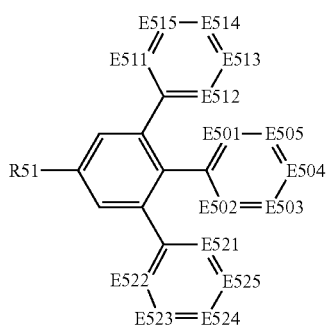

Formula (5)

In formula (5), R51 represents a substituent, E501, E502, E511 to E515, and E521 to E525 each represent —C(R52)= or —N=. E503 to E505 each represent —C(R52)=, wherein R52 represents a hydrogen atom (H) or a substituent. At least one of E501 and E502 is —N=, at least one of E511 to E515 is —N=, and at least one of E521 to E525 is —N=.

[Chemical Formula 29]

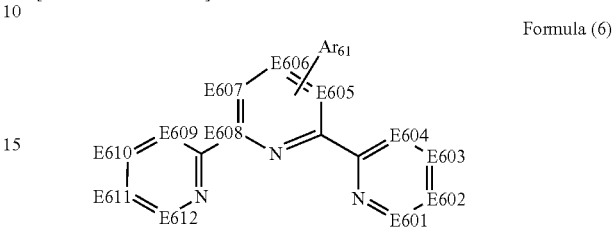

Formula (6)

In formula (6), E601 to E612 each represent —C(R61)= or —N=, wherein R61 represent a hydrogen atom (H) or a substituent. Ar61 represents a substituted or unsubstituted aromatic hydrocarbon ring or aromatic heterocyclic ring.

Examples of the substituted or unsubstituted aromatic hydrocarbon ring or aromatic heterocyclic ring represented by Ar61 in formula (6) may be the same as those for Ar41 in formula (4).

[Chemical Formula 30]

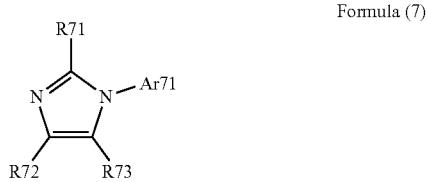

Formula (7)

In formula (7), R71 to R73 each represent a hydrogen atom (H) or a substituent, and Ar71 represents an aromatic hydrocarbon ring group or an aromatic heterocyclic ring group.

Examples of the aromatic hydrocarbon ring or aromatic heterocyclic ring represented by Ar71 in formula (7) may be the same as those for Ar41 in formula (4).

[Chemical Formula 31]

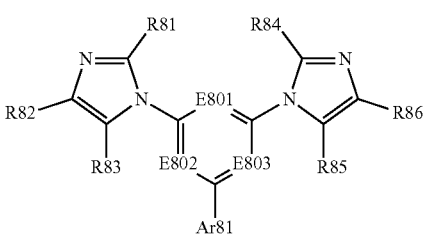

Formula (8)

Formula (8) is also one type of formula (7). In formula (8), R81 to R86 each represent a hydrogen atom (H) or a substituent. E801 to E803 each represent —C(R87)= or —N=, wherein R87 represents a hydrogen atom (H) or a substituent. Ar81 represents an aromatic hydrocarbon ring group or an aromatic heterocyclic ring group.

Examples of the aromatic hydrocarbon ring or aromatic heterocyclic ring represented by Ar81 in formula (8) may be the same as those for Ar41 in formula (4).

[Chemical Formula 32]

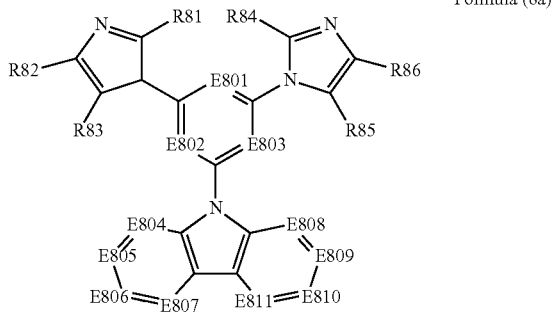

Formula (8a)

The compound having a structure represented by formula (8a) is one type of the compound having the structure of formula (8), in which a carbazole derivative corresponds to Ar81 in formula (8). In formula (8a), E804 to E811 each represent —C(R88)= or —N=, wherein R88 represents a hydrogen atom (H) or a substituent. At least one of E808 to E811 is —N=, and any of E804 to E807 and E808 to E811 may be linked together to form a new ring.

[Compound III]

Other compounds that may be used to form the nitrogen-containing layer 1a include compounds 1 to 166, which are shown below as examples, in addition to the compounds represented by formulae (1) to (8a). Such compounds contain a nitrogen atom or atoms capable of interacting with silver used to form the electrode layer 1b. Such compounds are also materials having electron transport properties or electron injection properties. Therefore, the transparent electrode 1 having the nitrogen-containing layer 1a formed with any of such compounds is suitable for an organic electroluminescent device, and the nitrogen-containing layer 1a can be used as an electron transport layer or an electron injection layer in such an organic electroluminescent device. It should be noted that compounds 1 to 166 include compounds having an effective lone pair content [n/M] in the specified range and such compounds may be used alone to form the nitrogen-containing layer 1a. Compounds 1 to 166 also include compounds corresponding to formulae (1) to (8a) shown above.

[Chemical Formula 33]

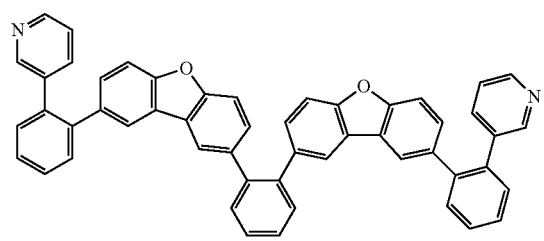

1

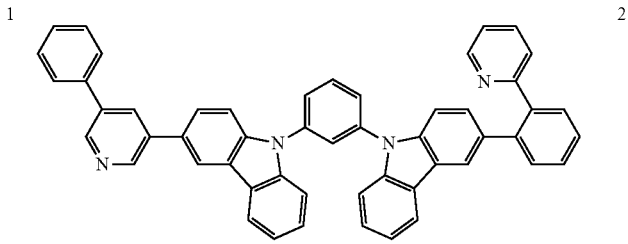

2

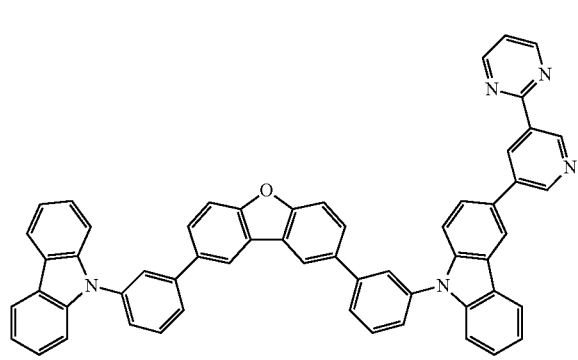

3

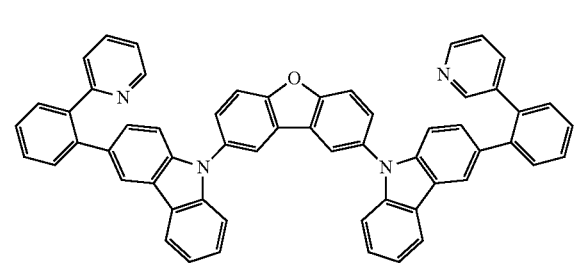

4

5
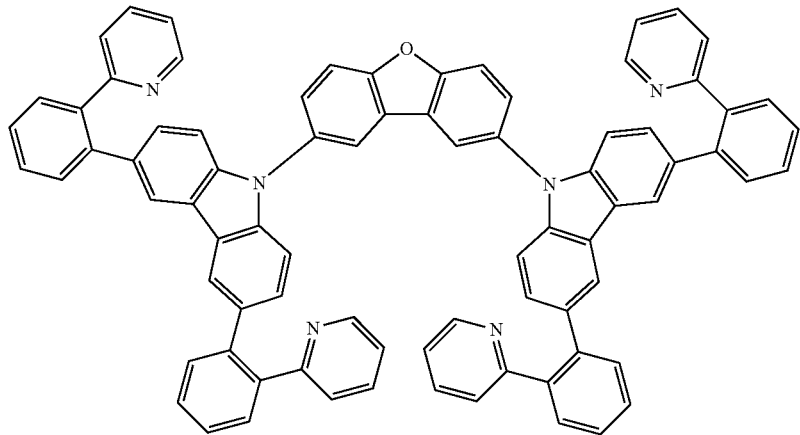
[Chemical Formula 34]
6
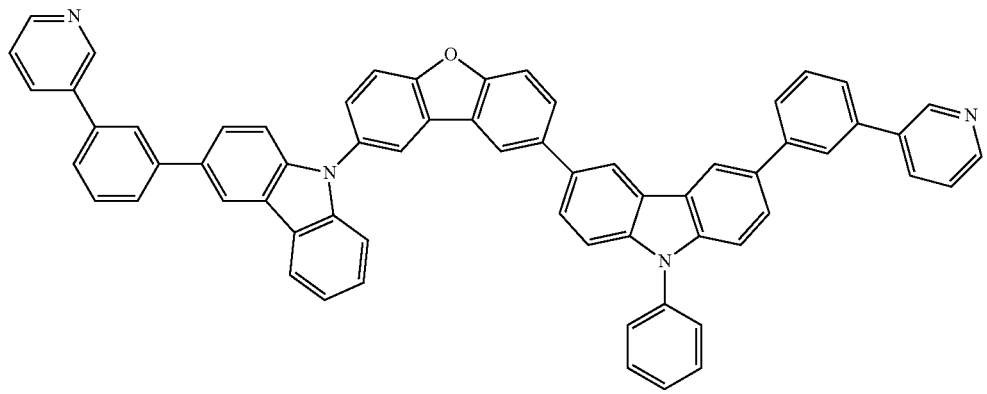
7
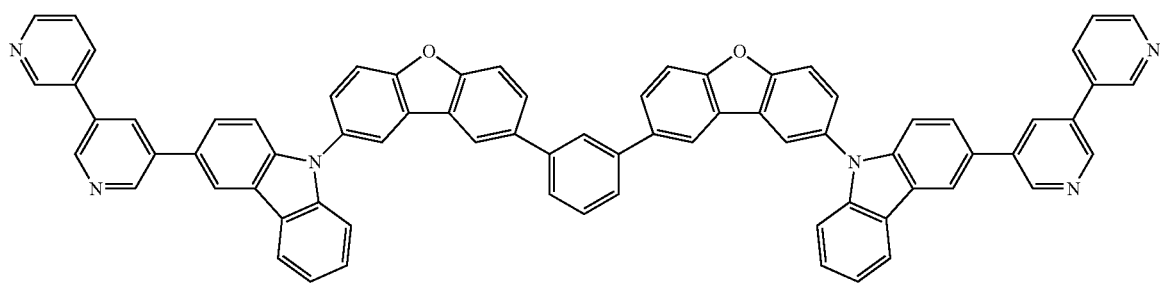
8
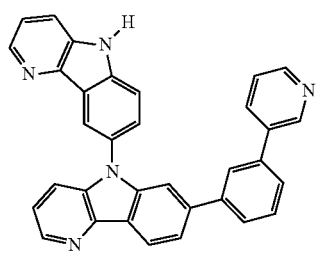
9
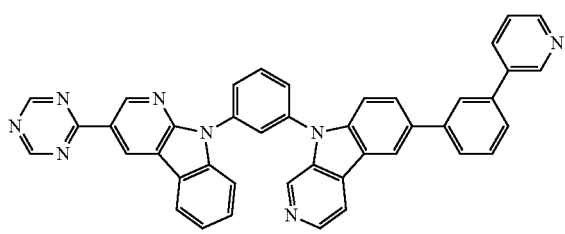

[Chemical Formula 35]
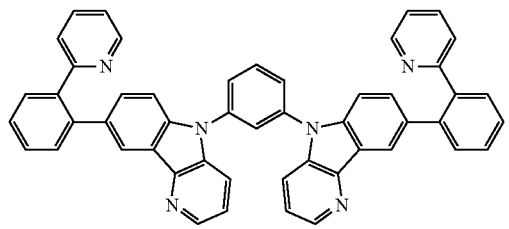
10
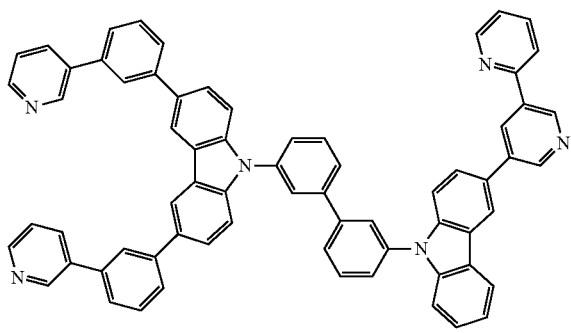
11
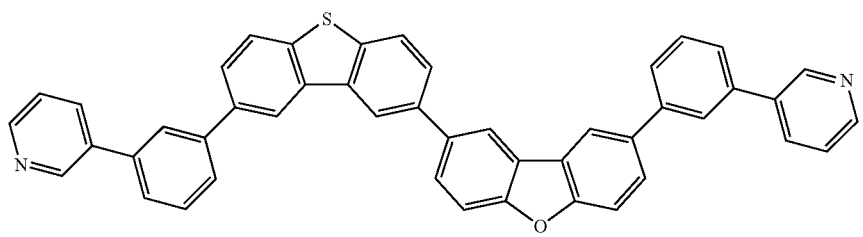
12
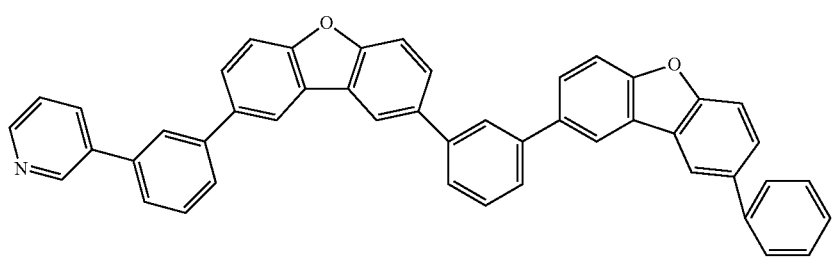
13
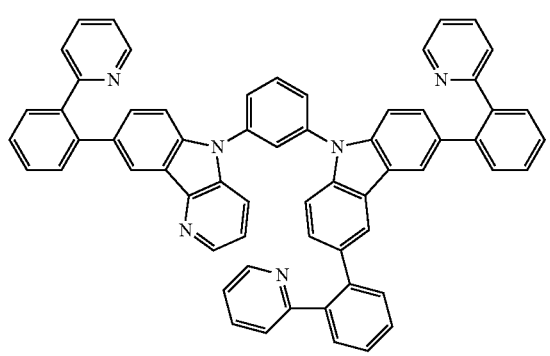
14
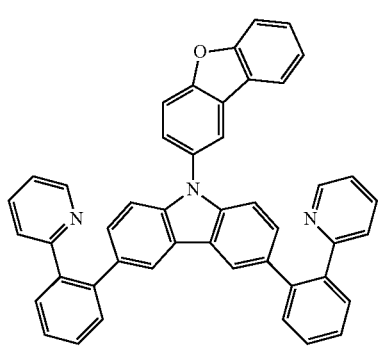
15

[Chemical Formula 36]
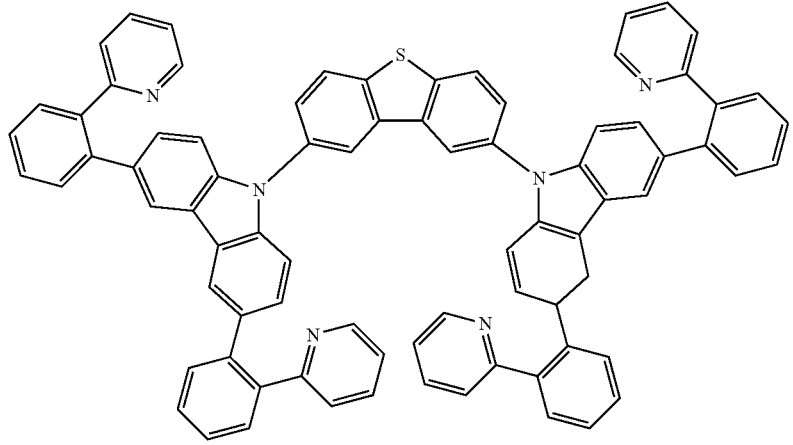
16
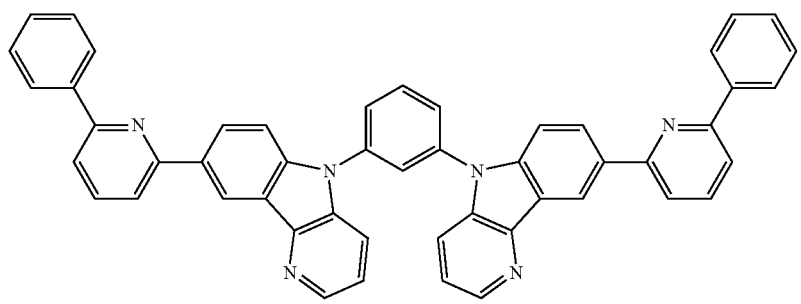
17
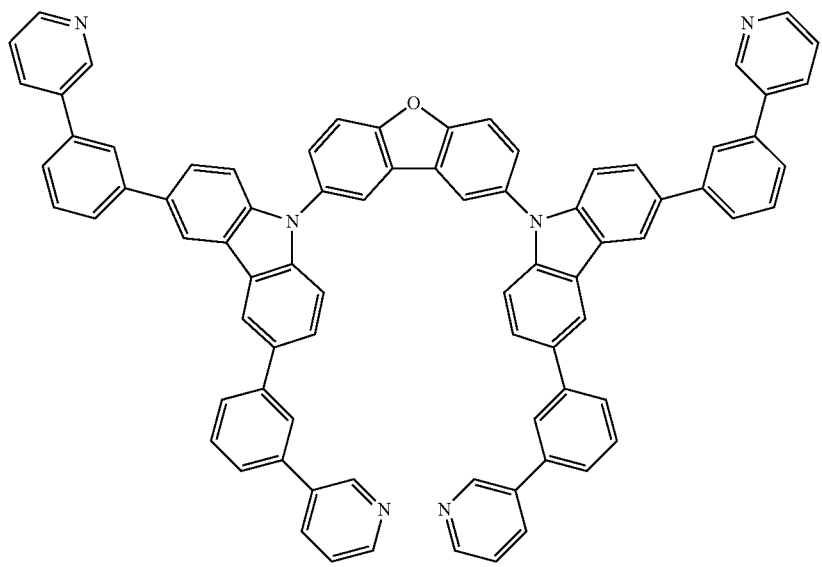
18
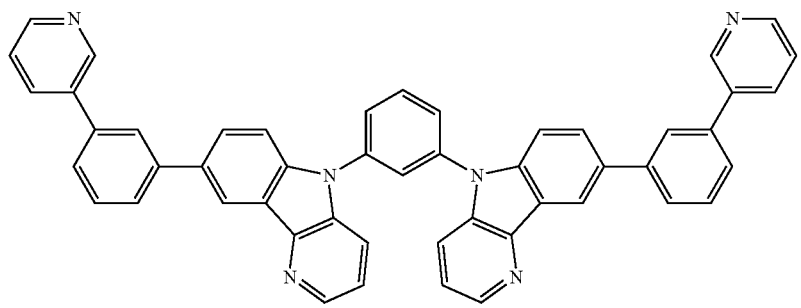
19

-continued
[Chemical Formula 37]
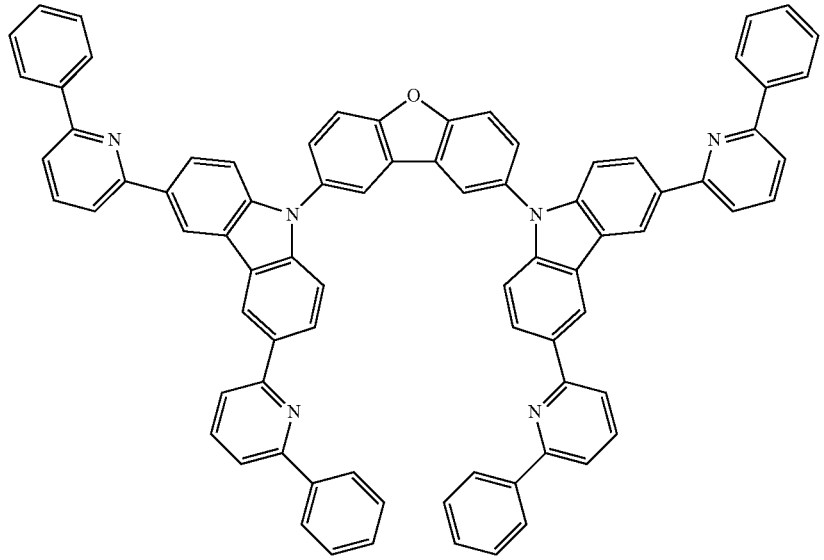
20
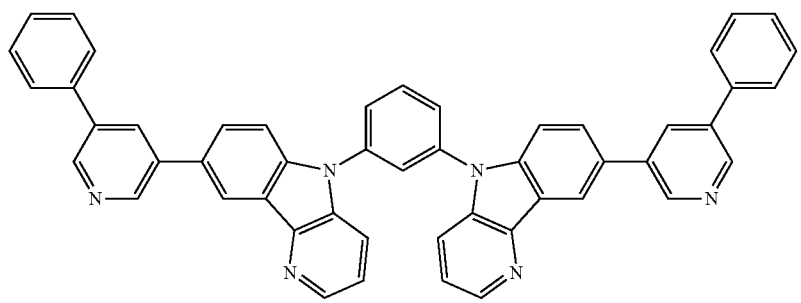
21
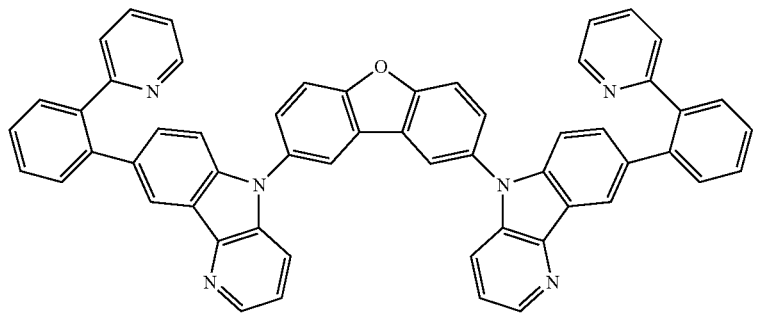
22
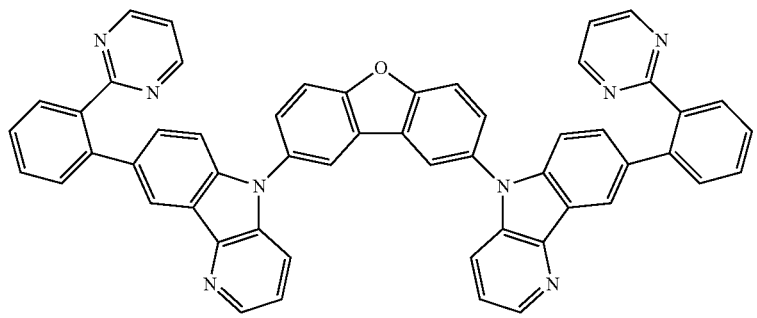
23

[Chemical Formula 38]
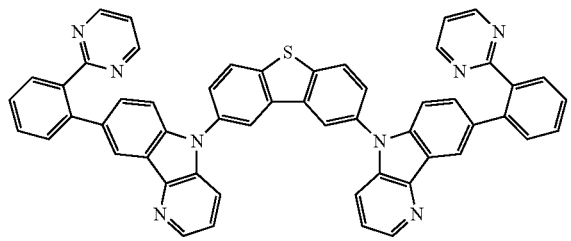
24
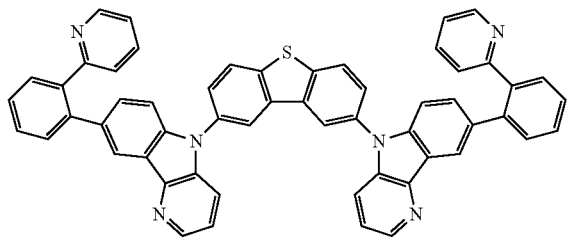
25
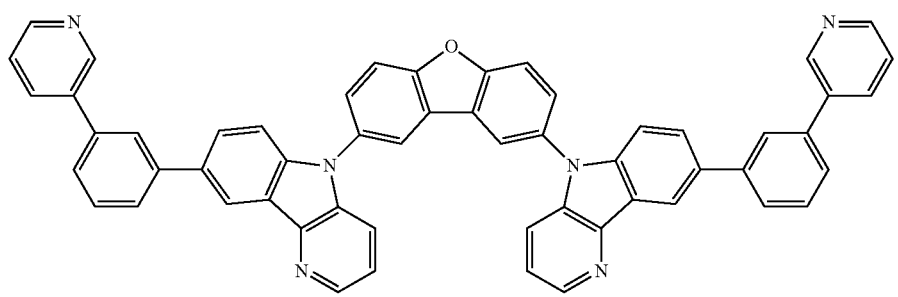
26
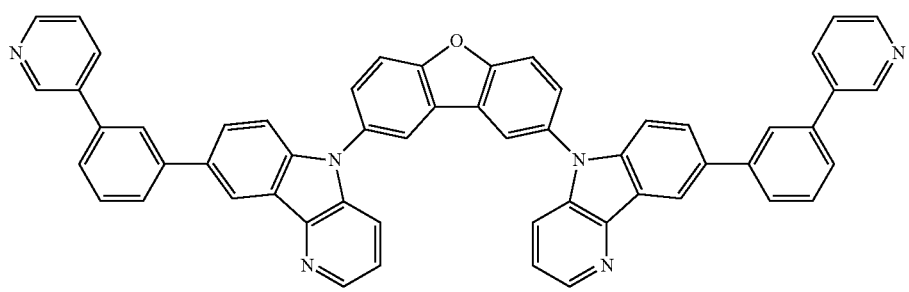
27
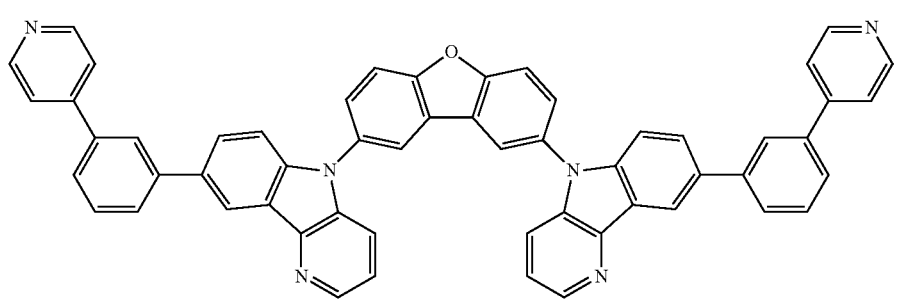
28
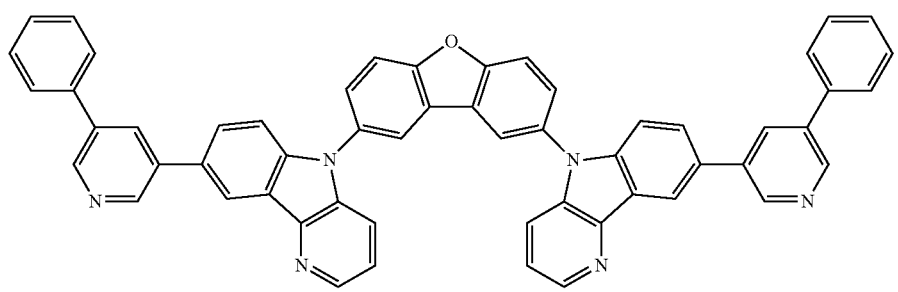
29

[Chemical Formula 39]
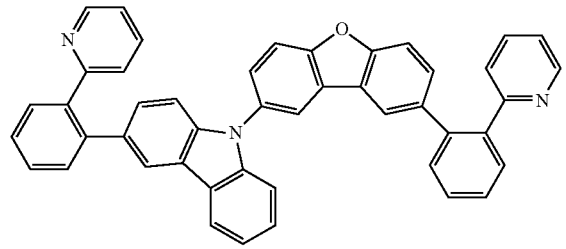
30
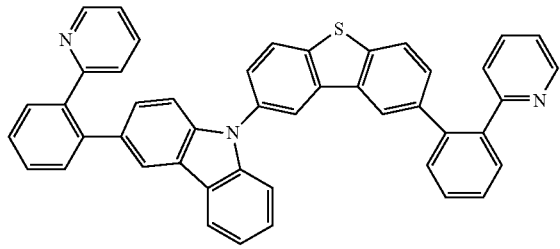
31
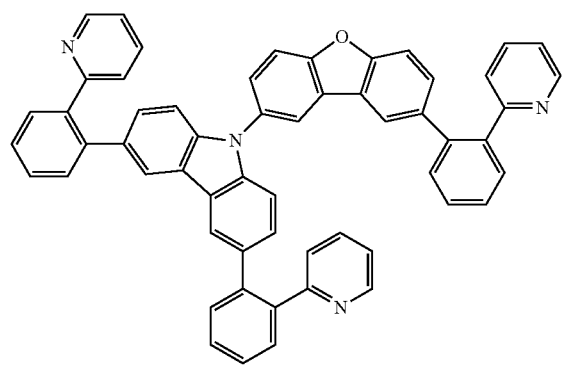
32
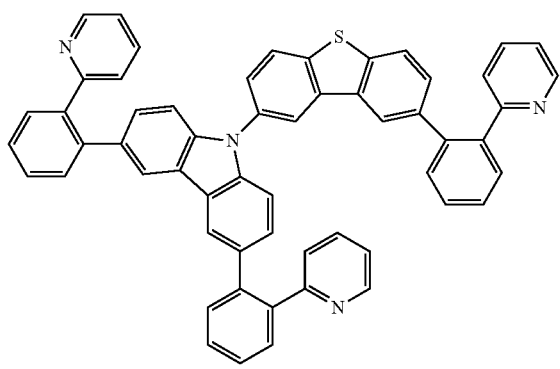
33
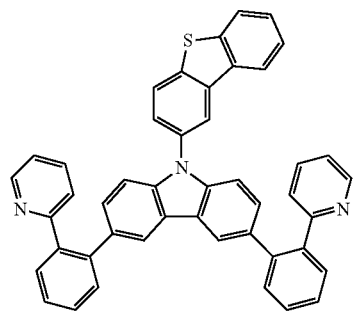
34
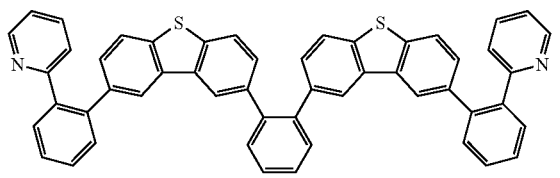
35
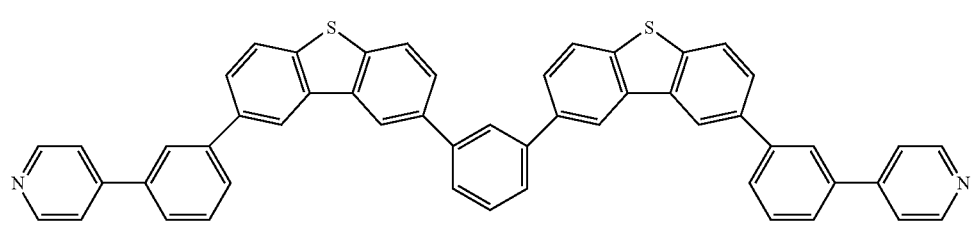
36

[Chemical Formula 40]
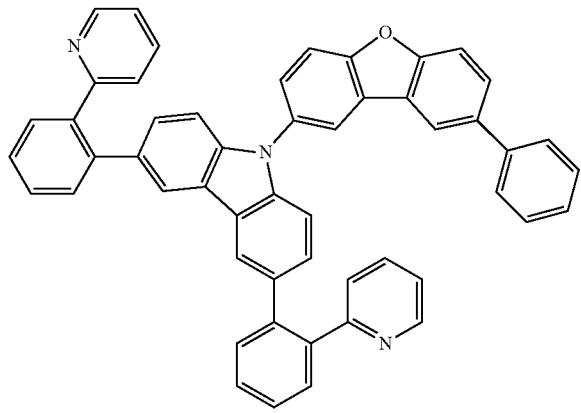
37
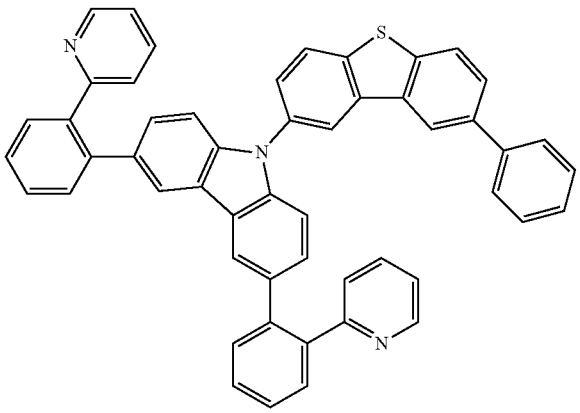
38
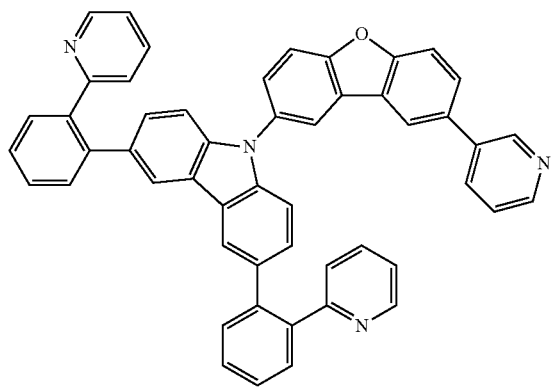
39
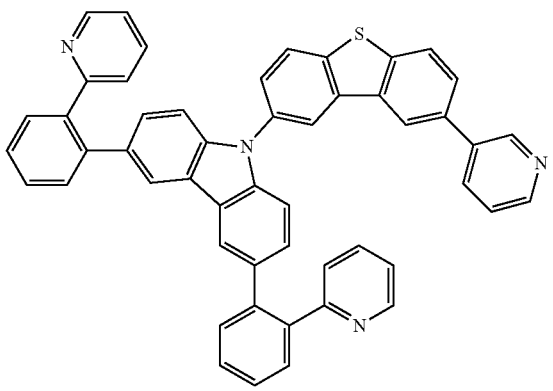
40
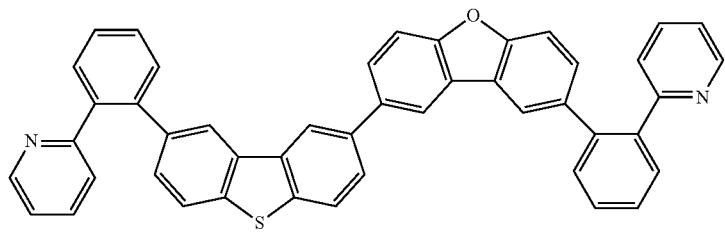
41
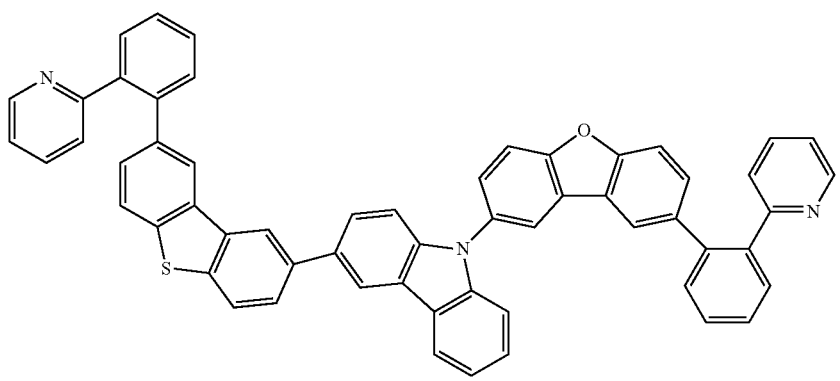
42

[Chemical Formula 41]
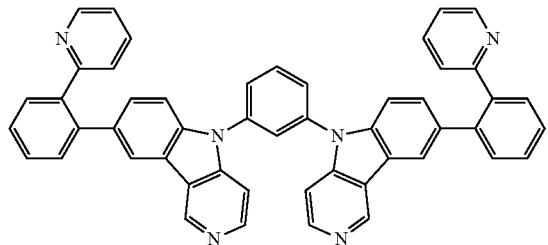
43
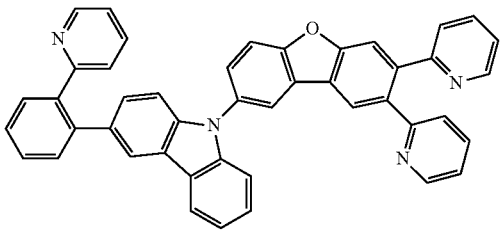
44
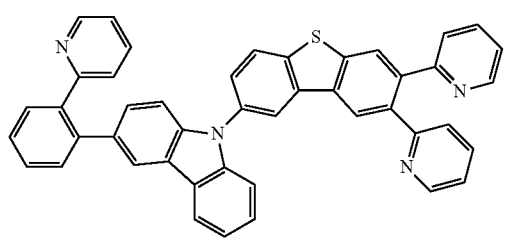
45
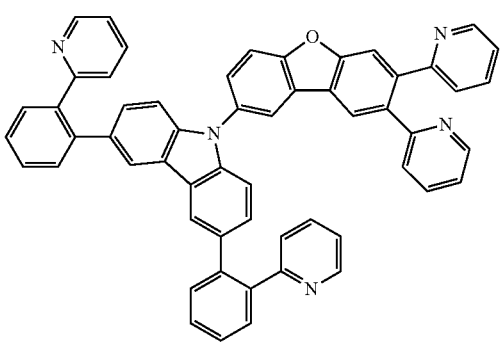
46
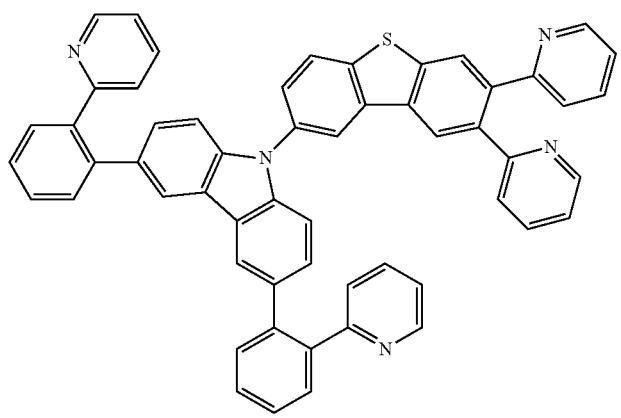
47
[Chemical Formula 42]
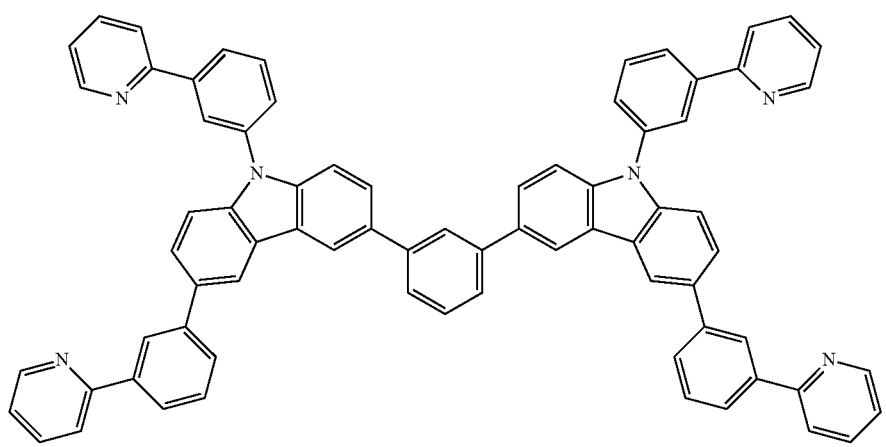
48

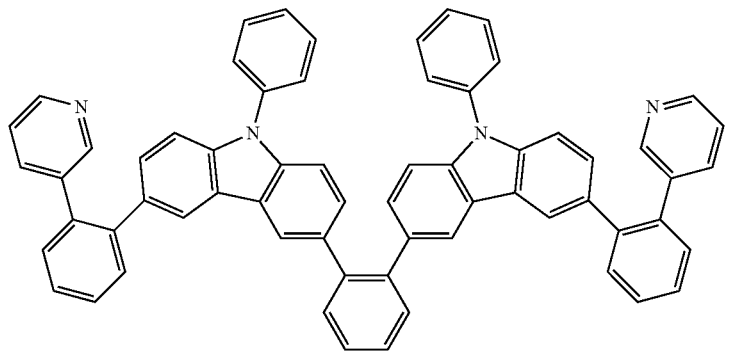
49
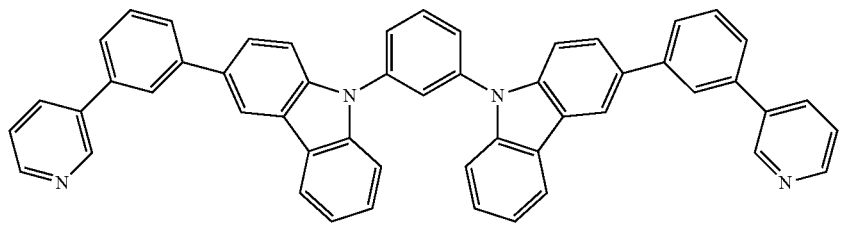
50
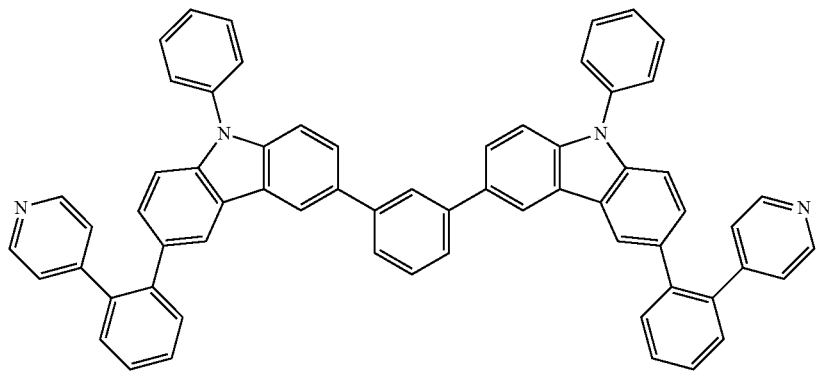
51
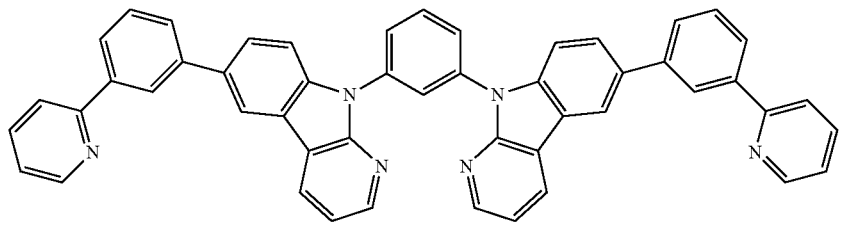
52
[Chemical Formula 43]
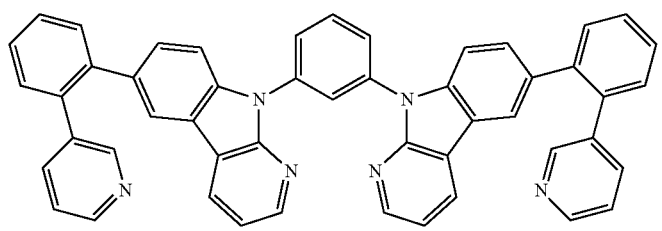
53

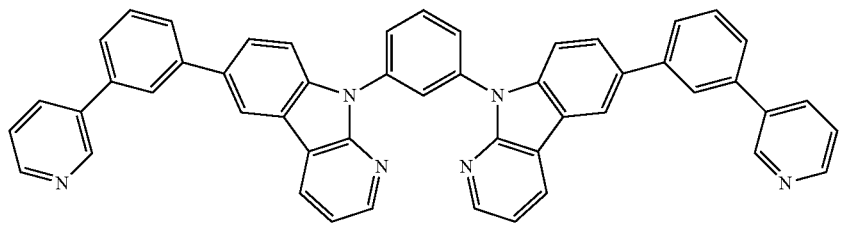
54
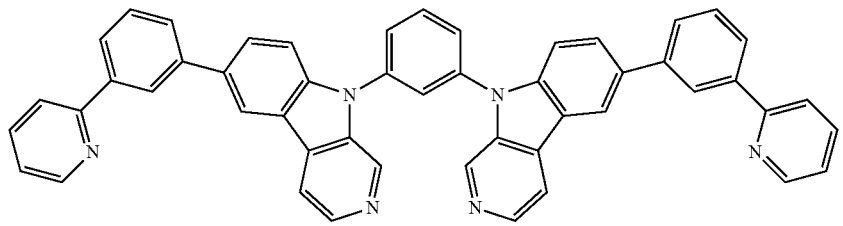
55
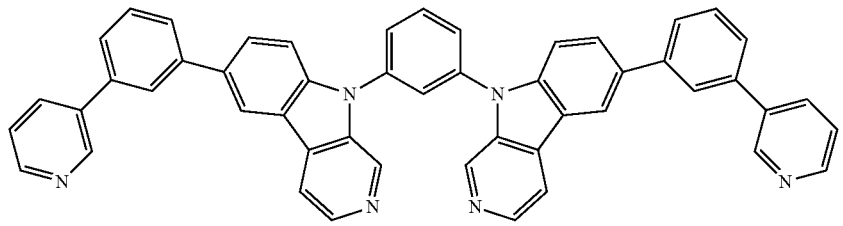
56
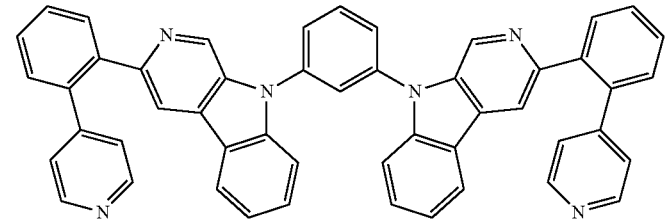
57
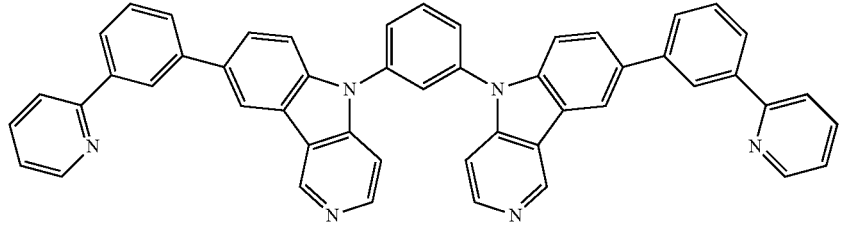
58
[Chemical Formula 44]
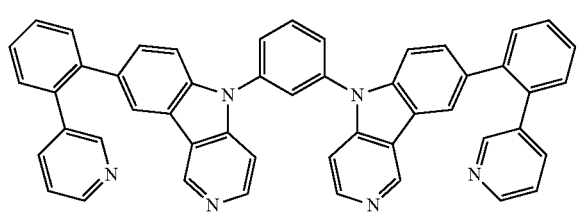
59
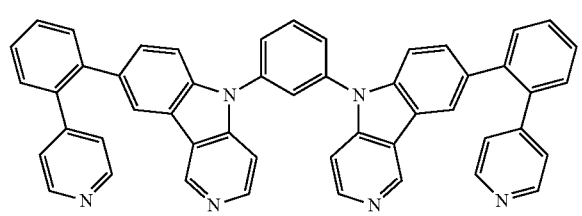
60

-continued
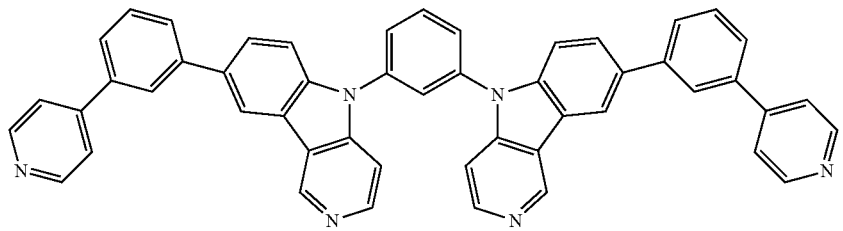
61
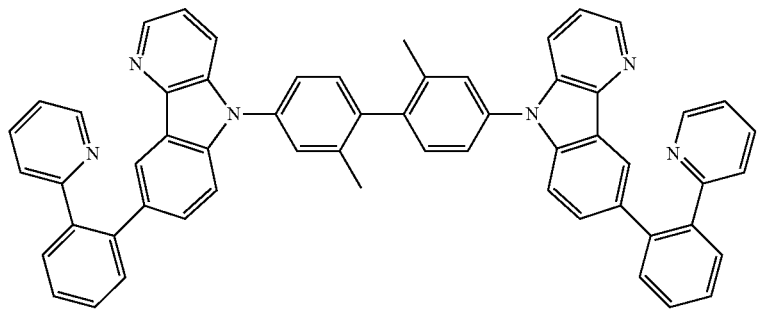
62
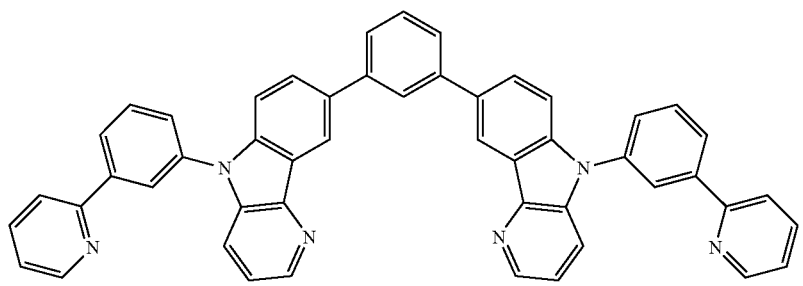
63
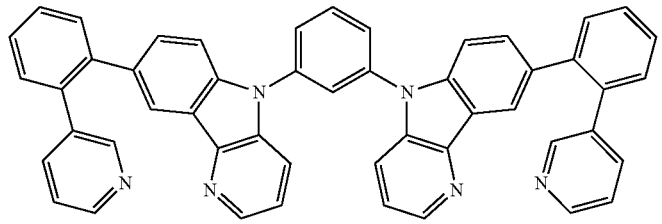
64
[Chemical Formula 45]
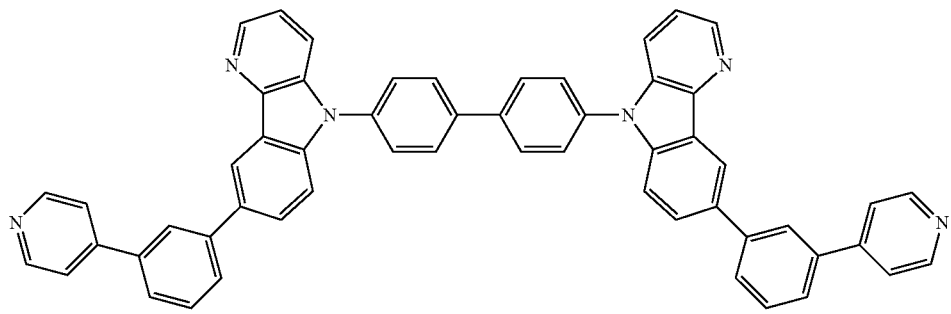
65

-continued
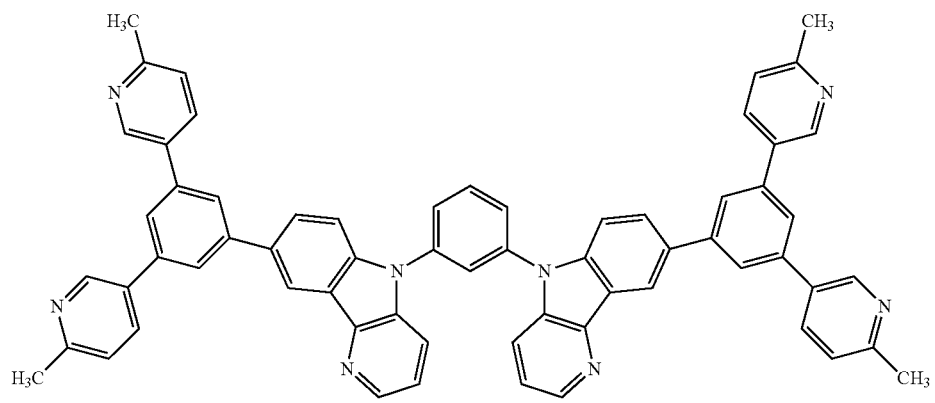
66
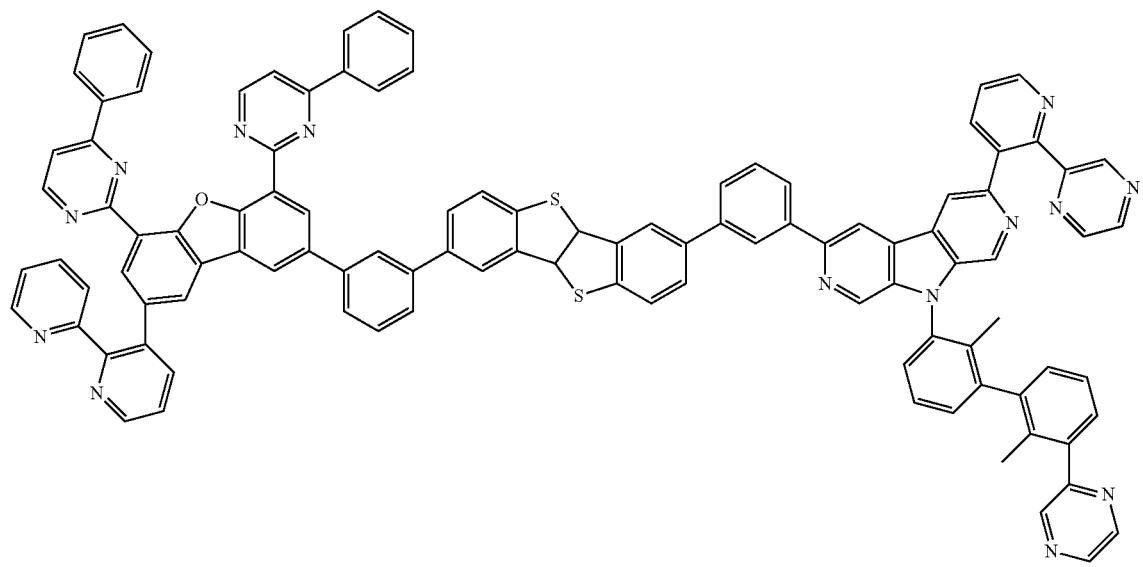
67
[Chemical Formula 46]
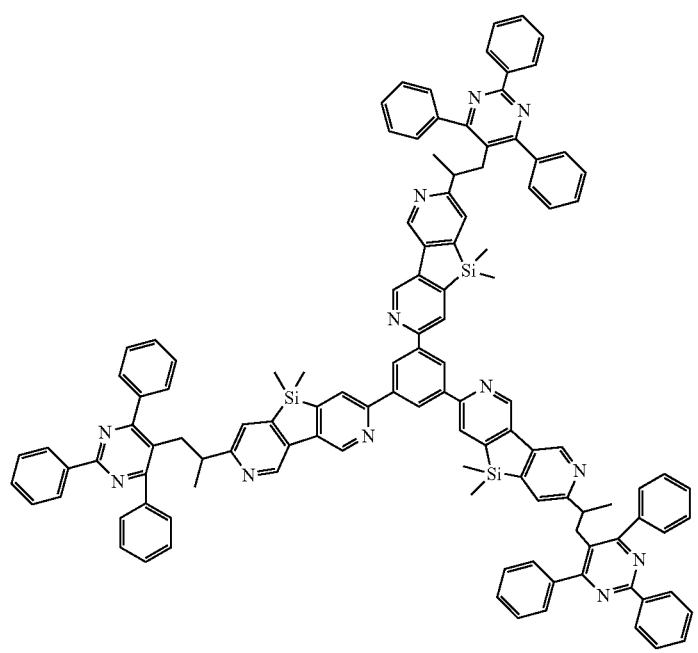
68

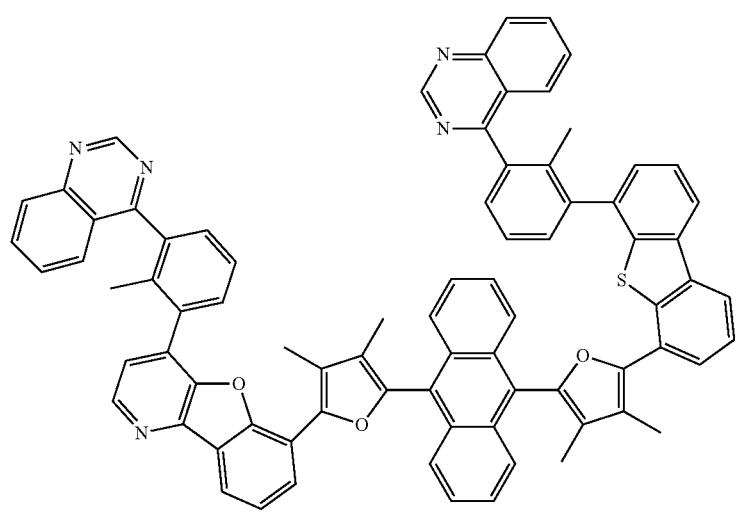
69
[Chemical Formula 47]
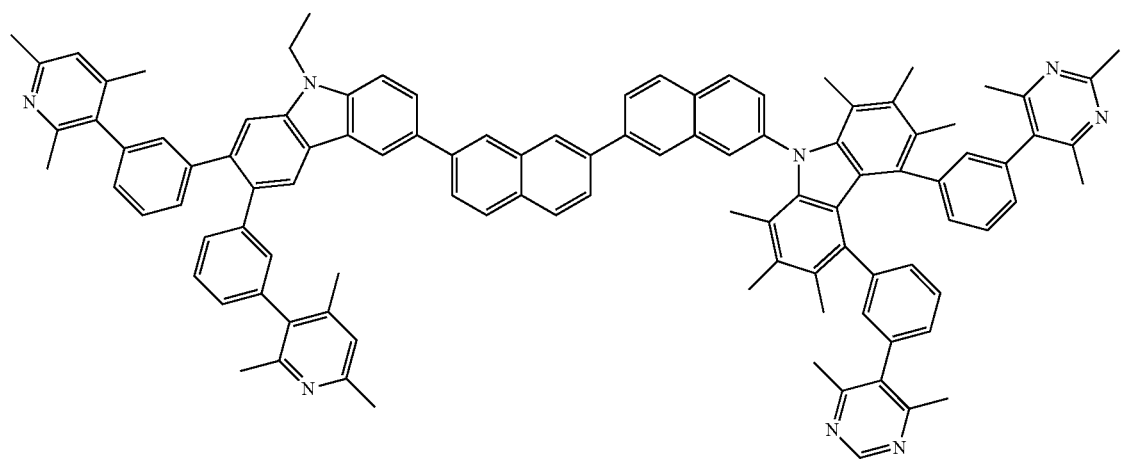
70
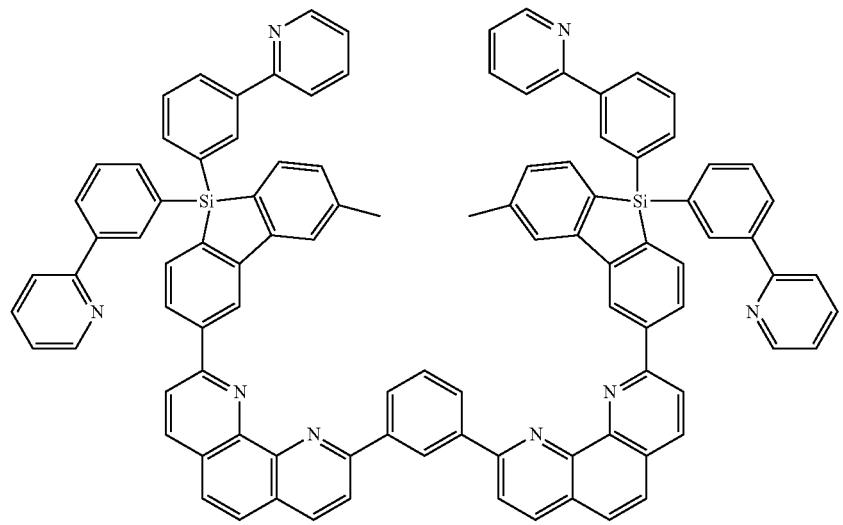
71

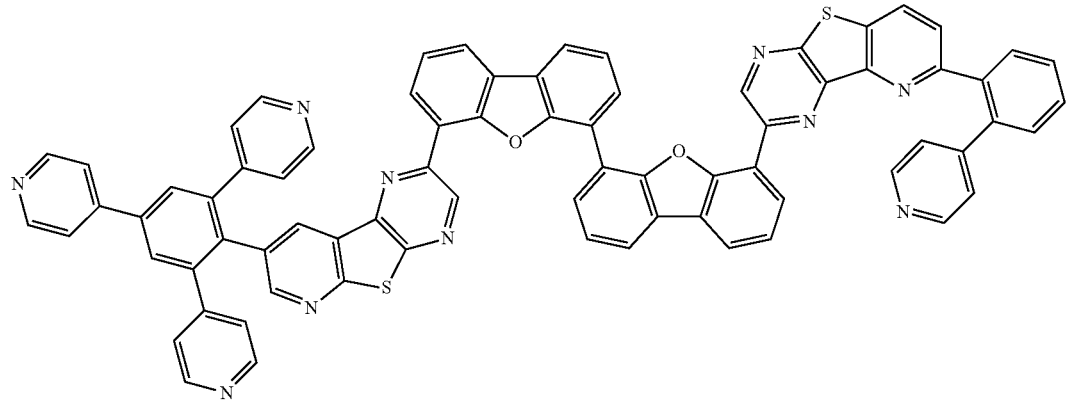
72
[Chemical Formula 48]
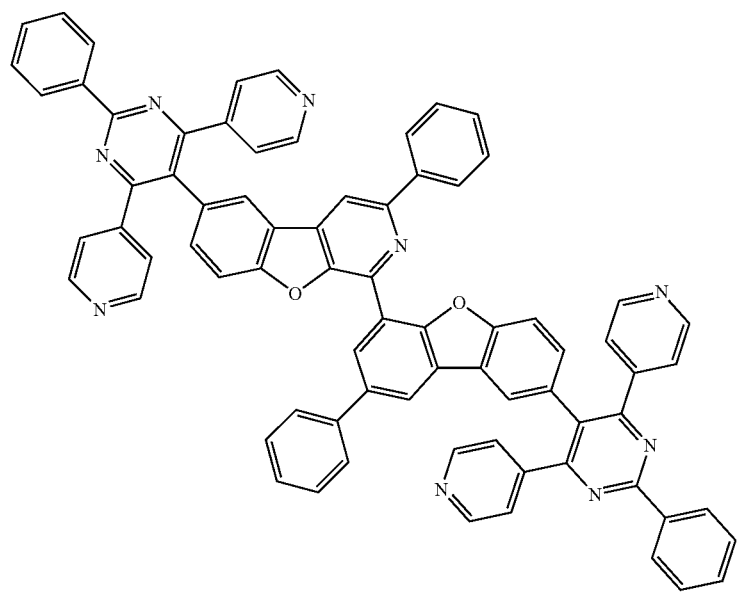
73
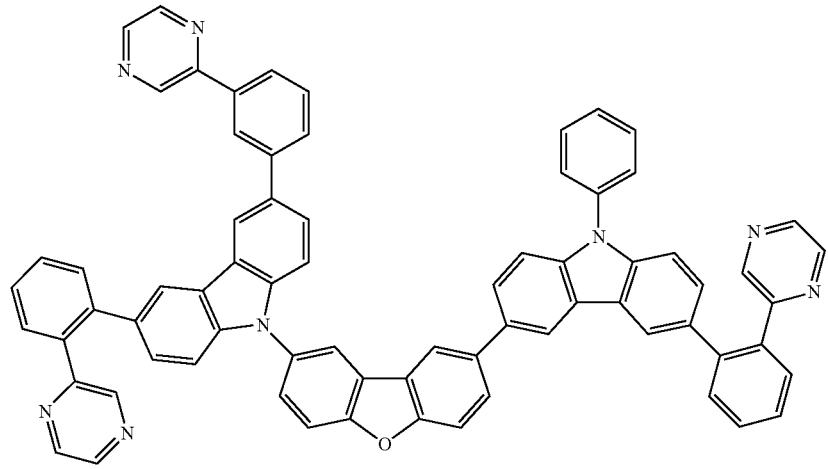
74

75
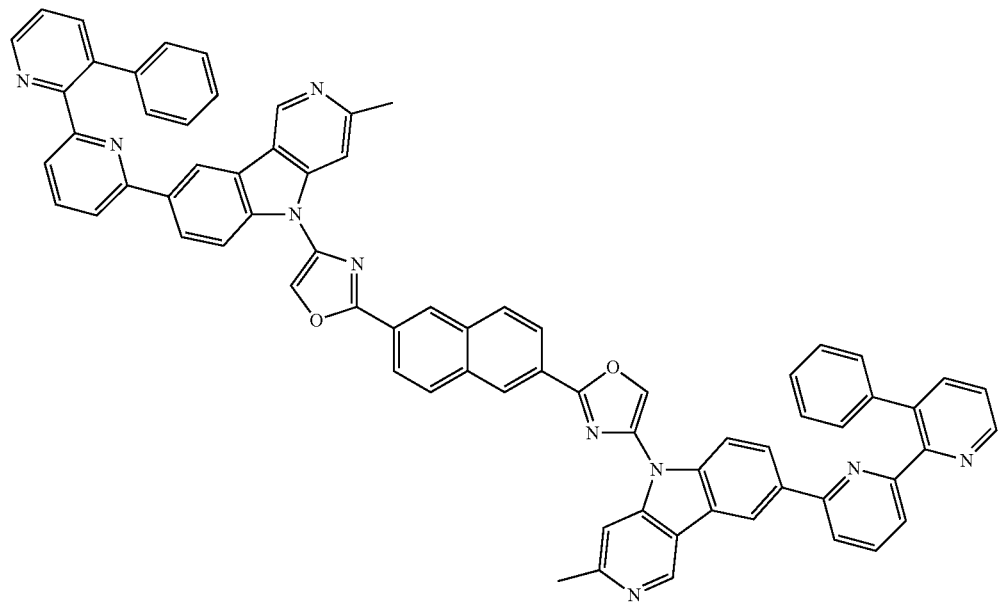
[Chemical Formula 49]
76
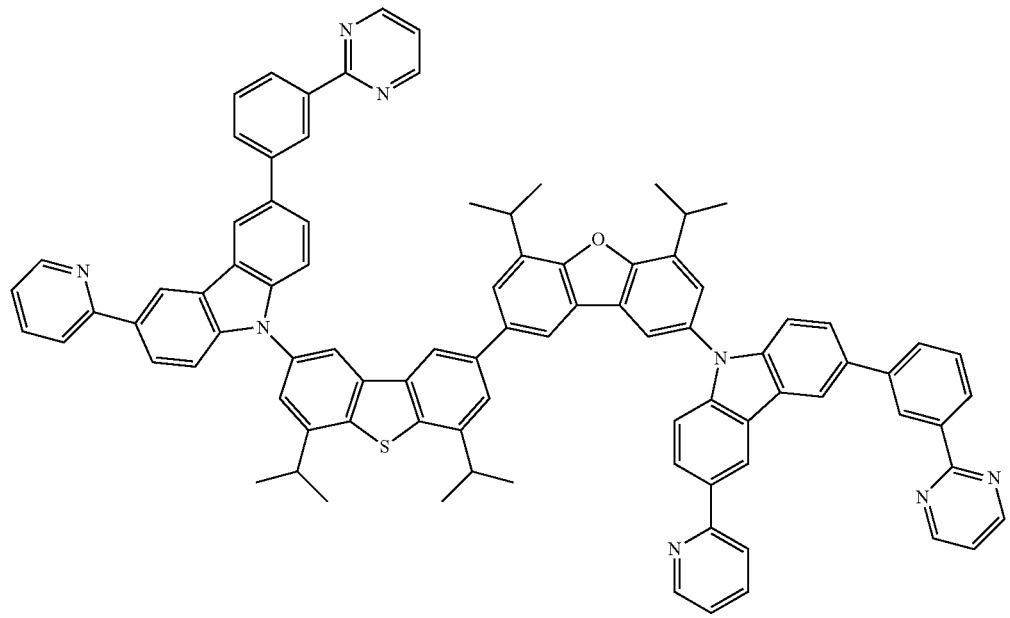
77
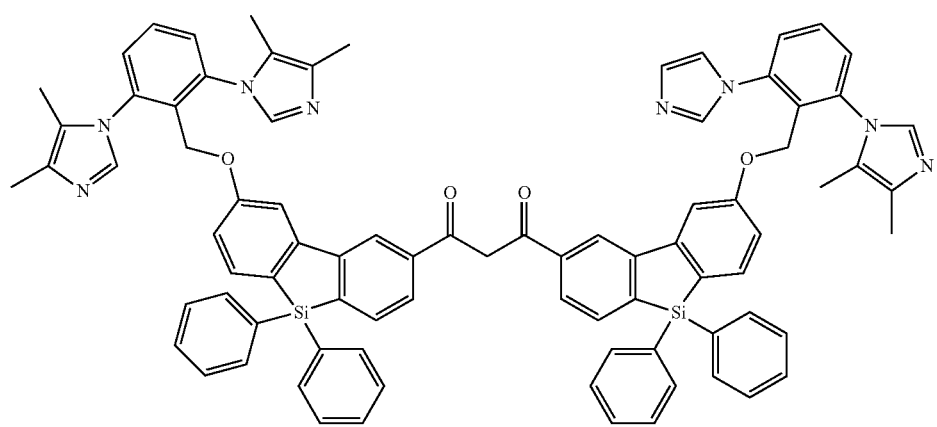

-continued
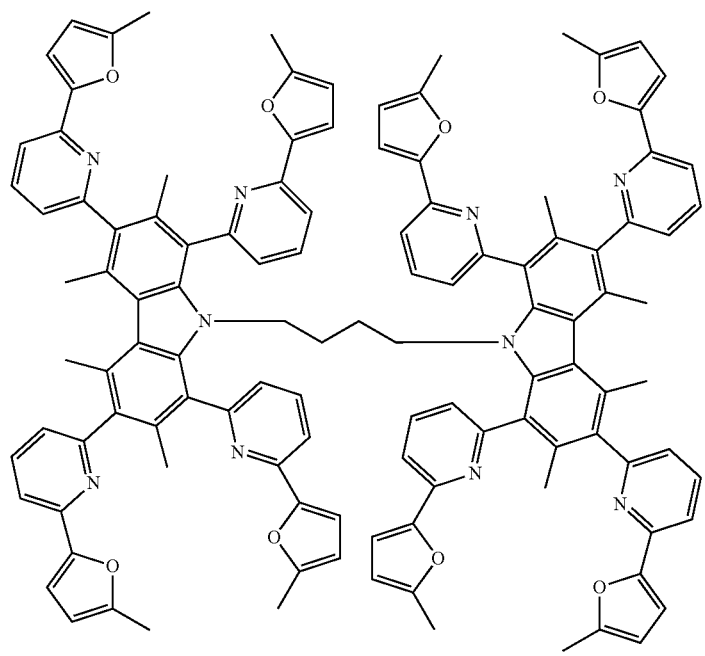
78
[Chemical Formula 50]
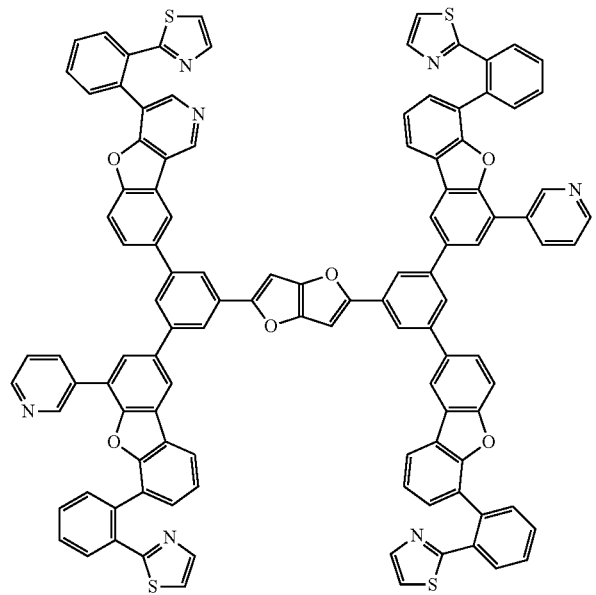
79

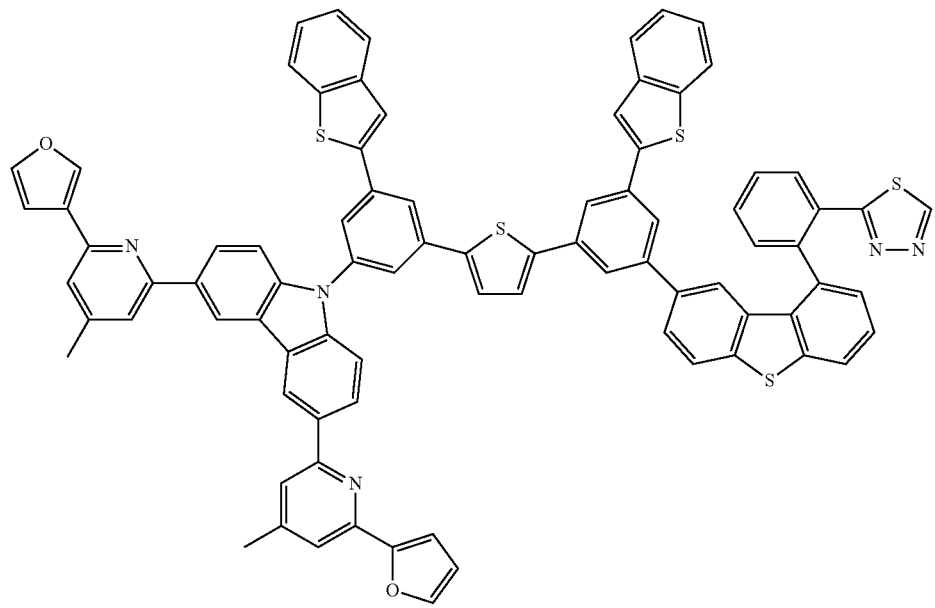
80
[Chemical Formula 51]
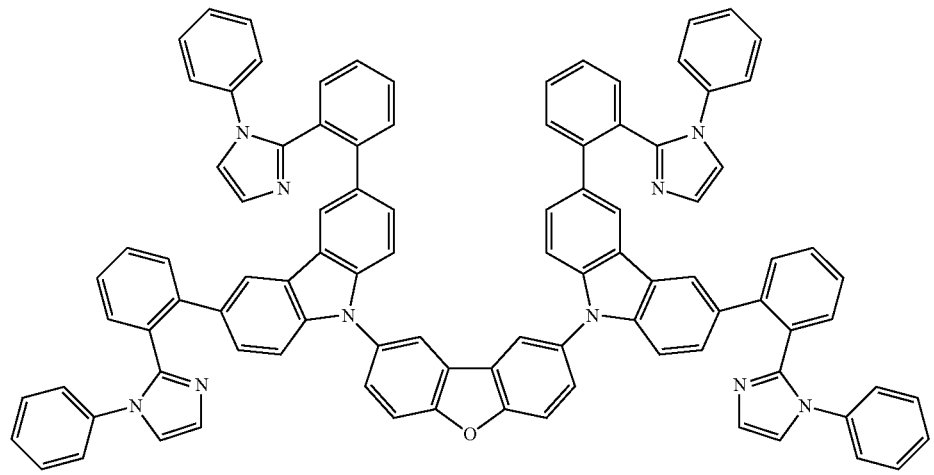
81
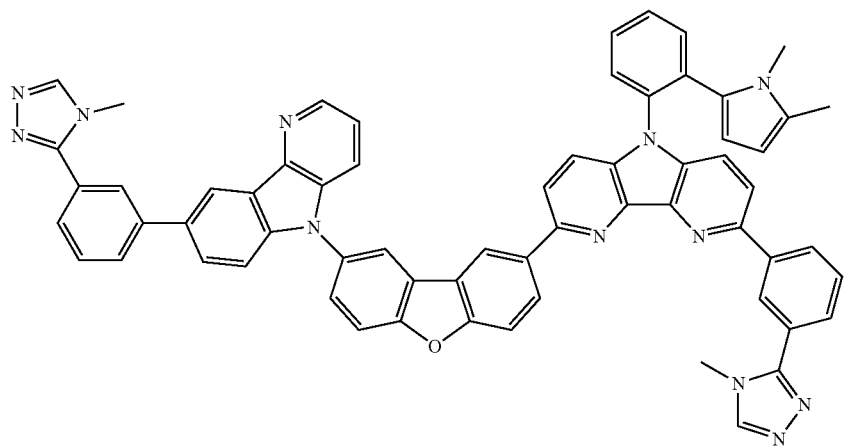
82

83
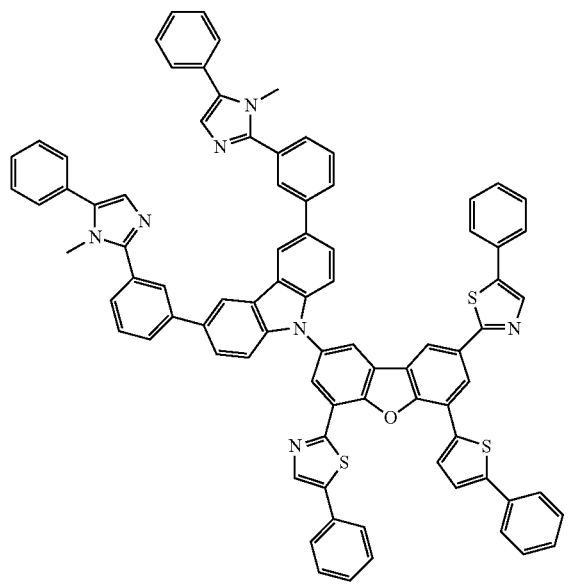
[Chemical Formula 52]
84
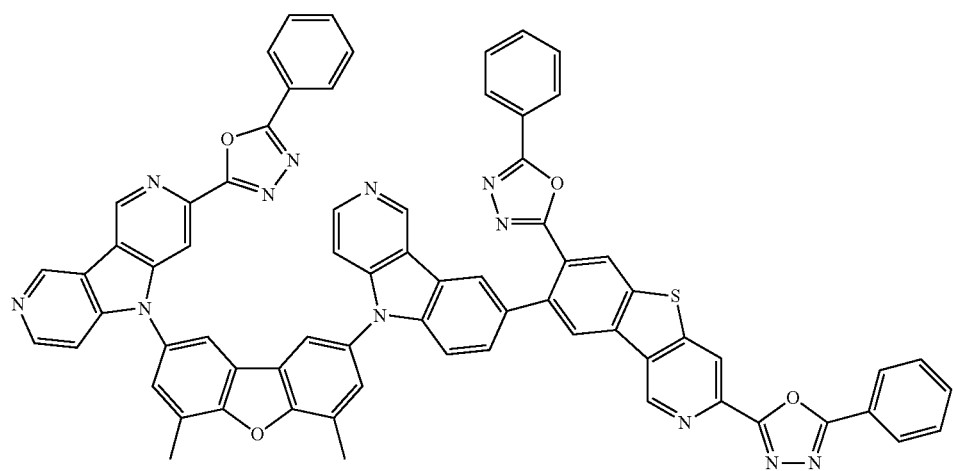

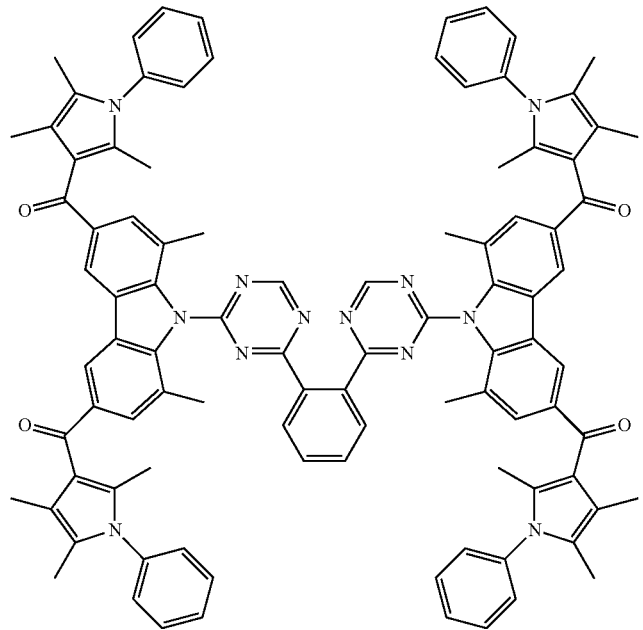
85
[Chemical Formula 53]
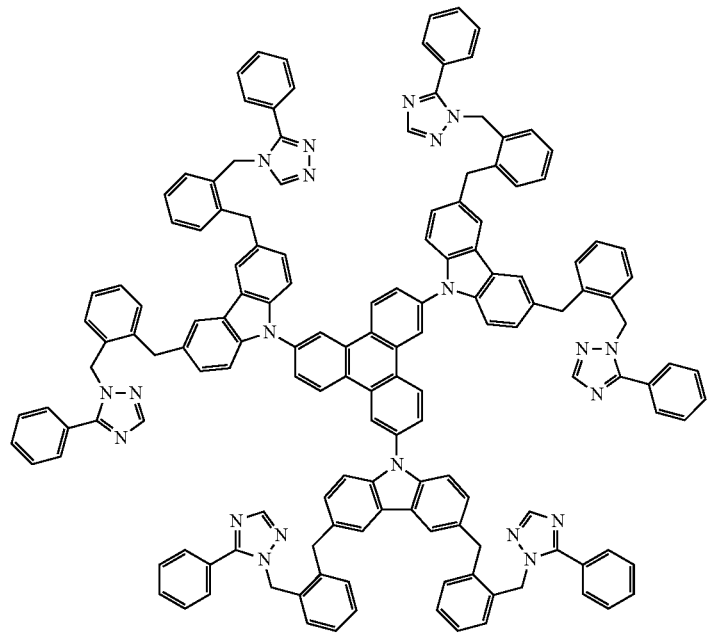
86

87
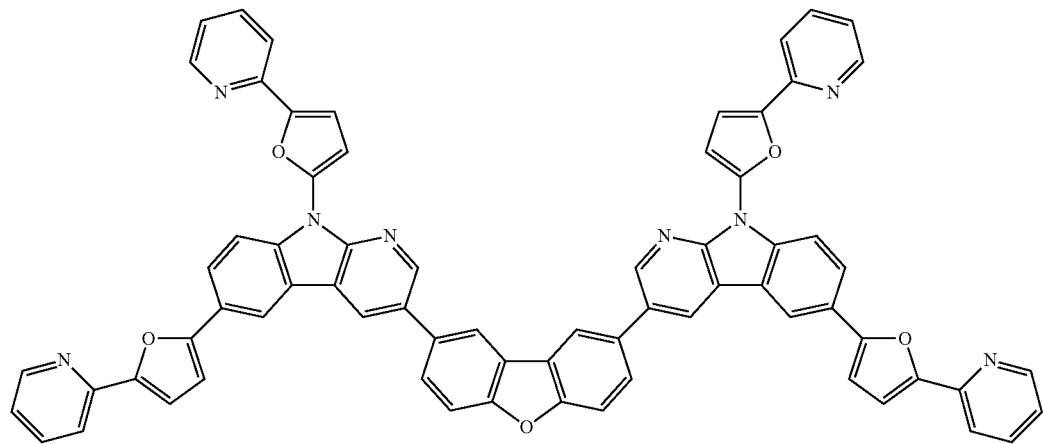
88
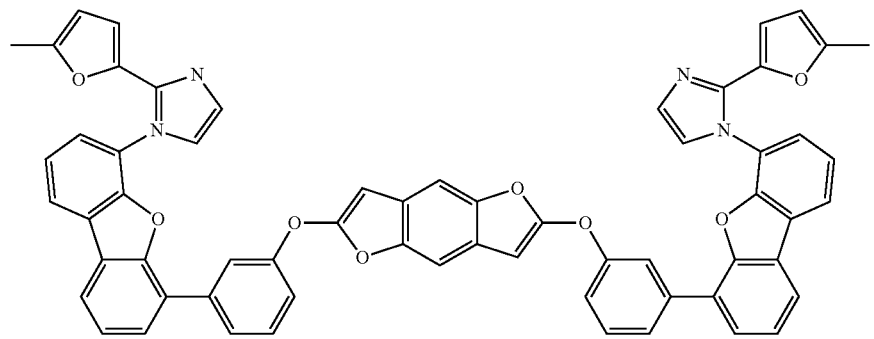
[Chemical Formula 54]
89
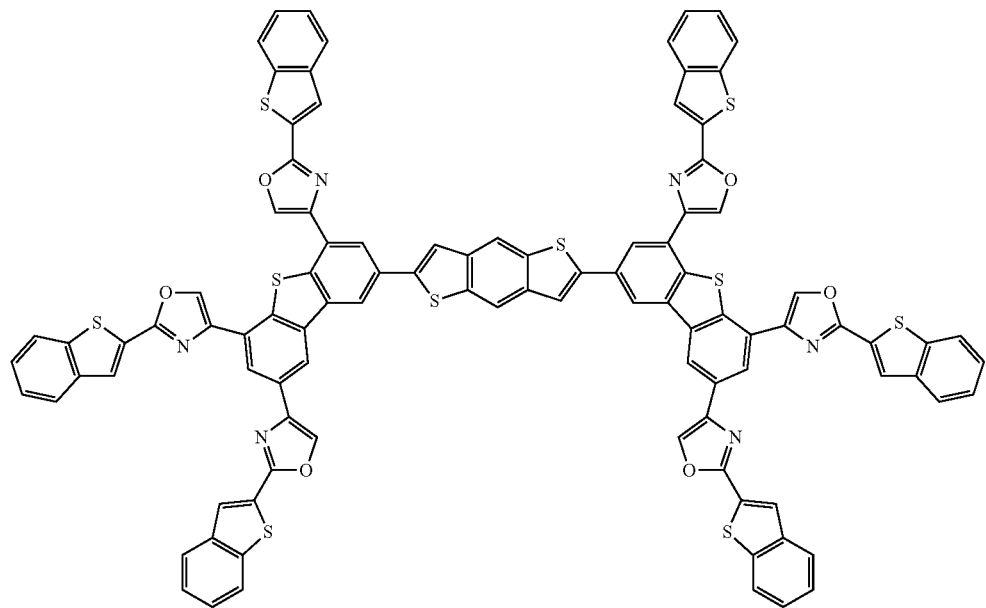

-continued
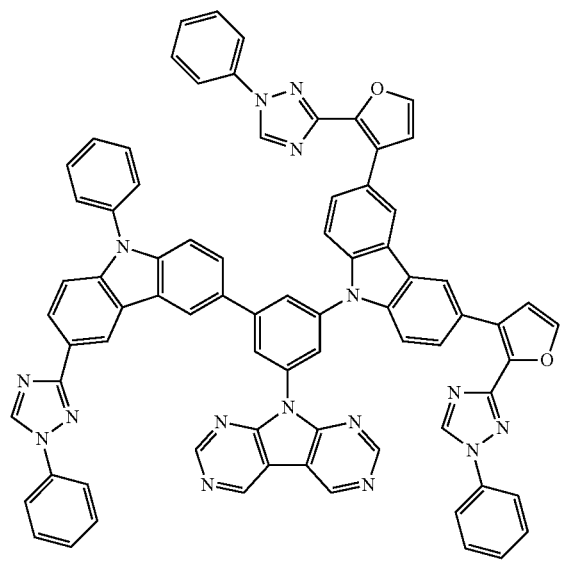
90
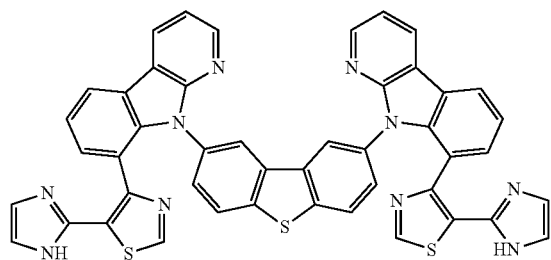
91
[Chemical Formula 55]
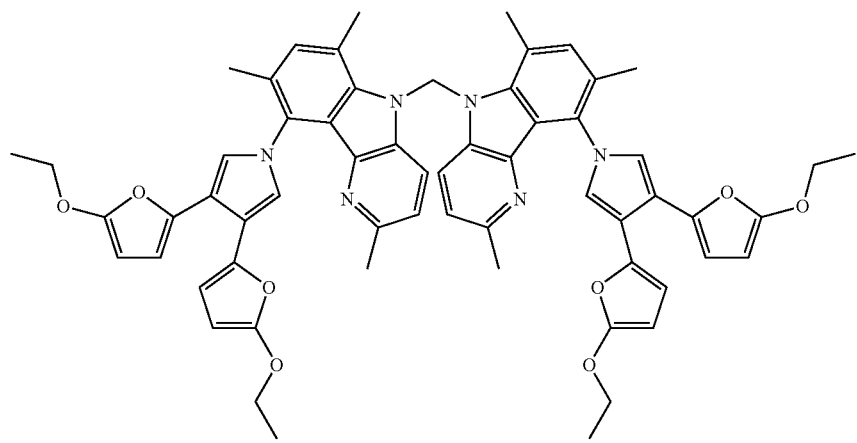
92
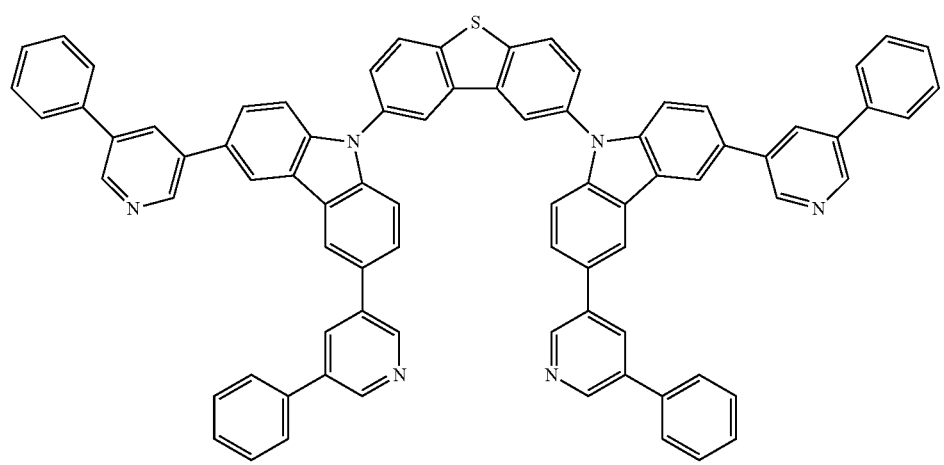
93

94
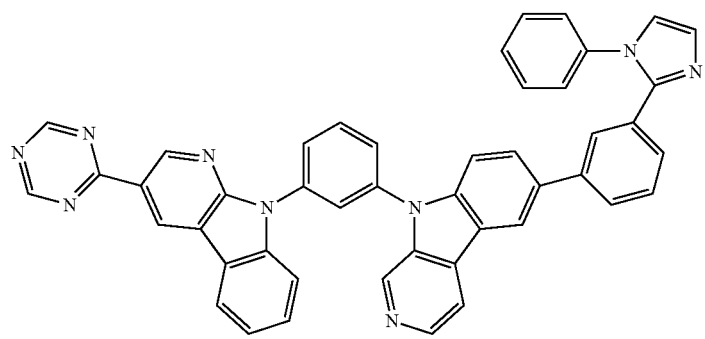
95
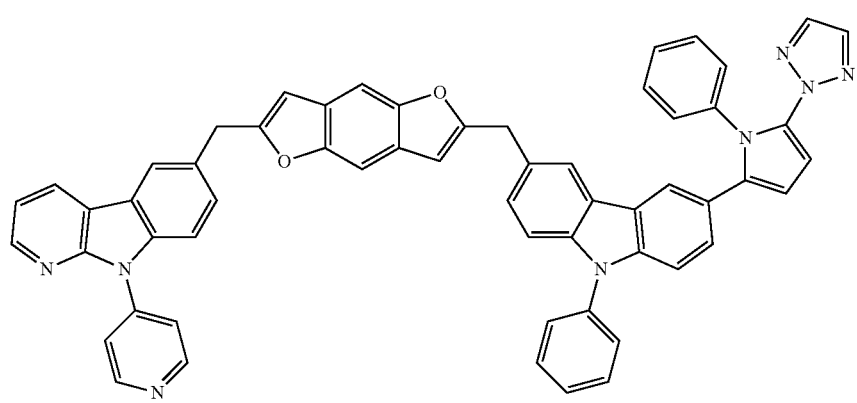
[Chemical Formula 56]
96
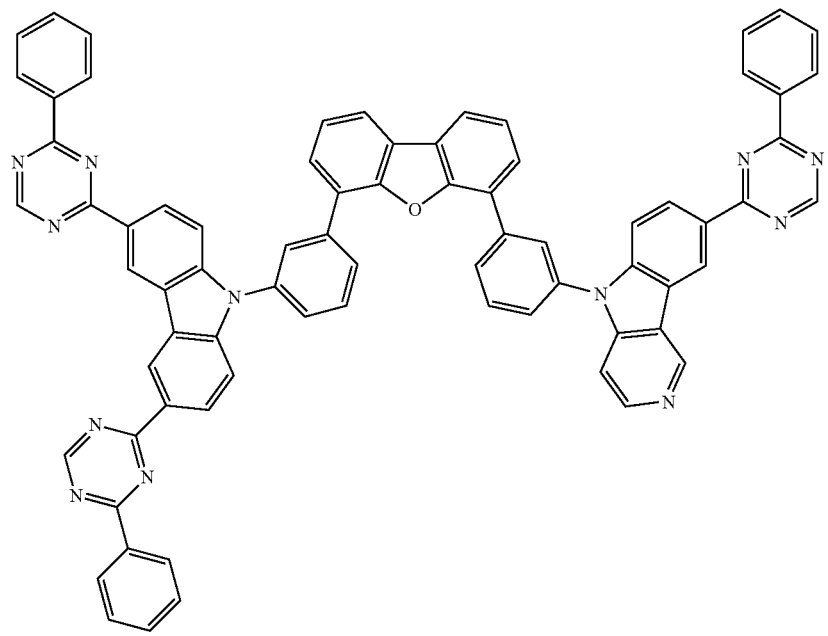

-continued
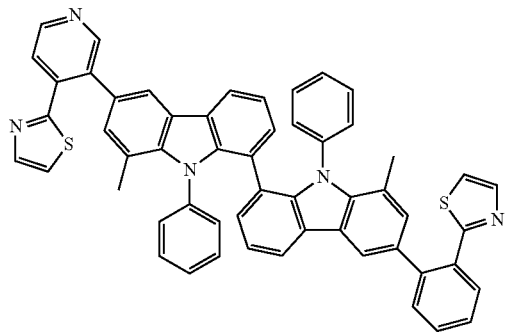
97
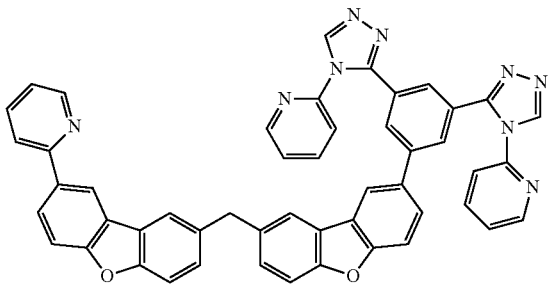
98
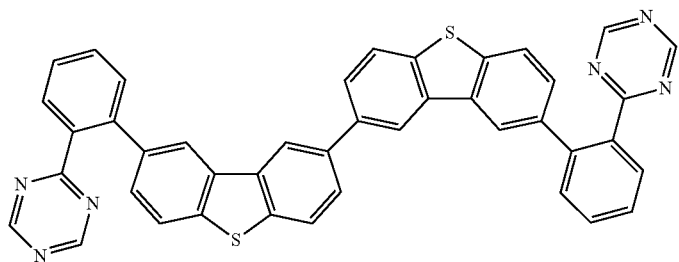
99
[Chemical Formula 57]
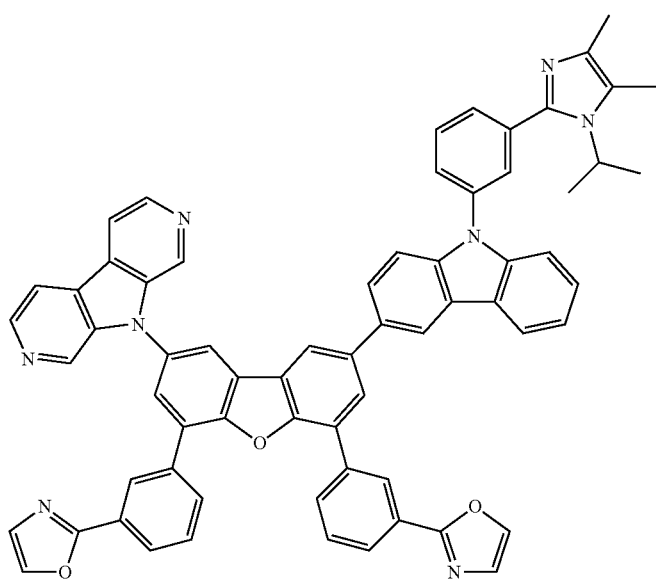
100

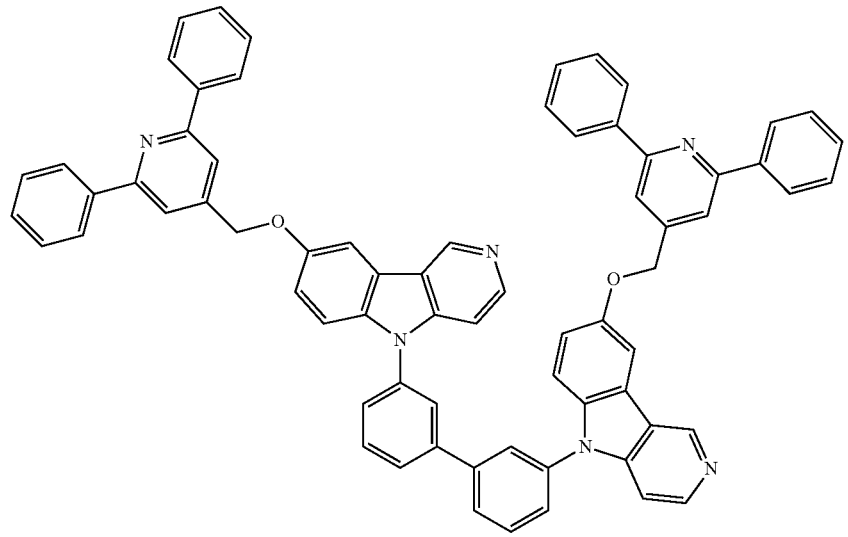
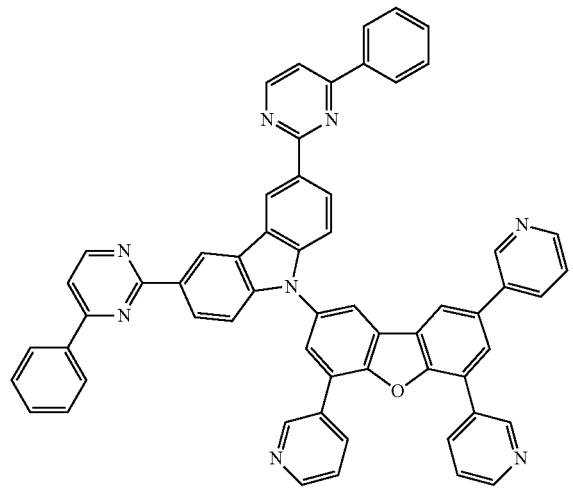
[Chemical Formula 58]
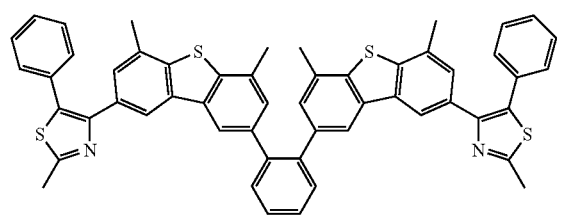
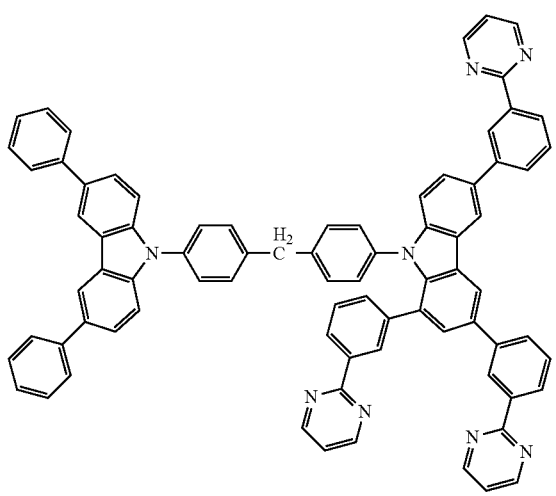

-continued
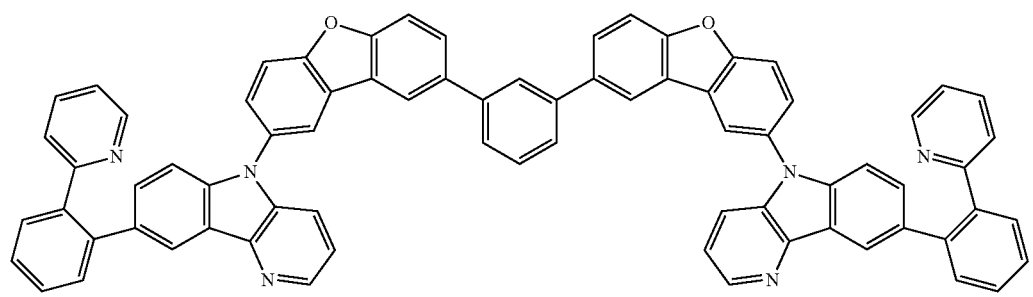
105
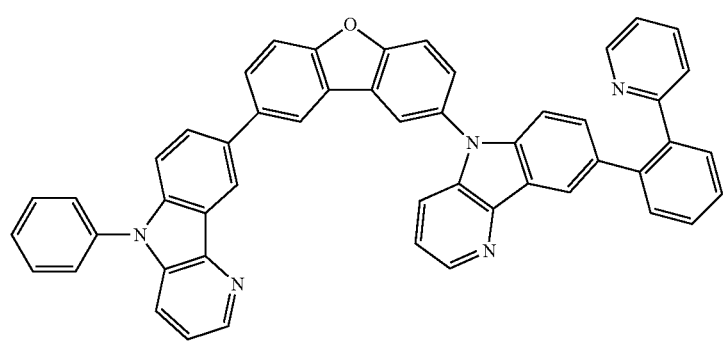
106
[Chemical Formula 59]
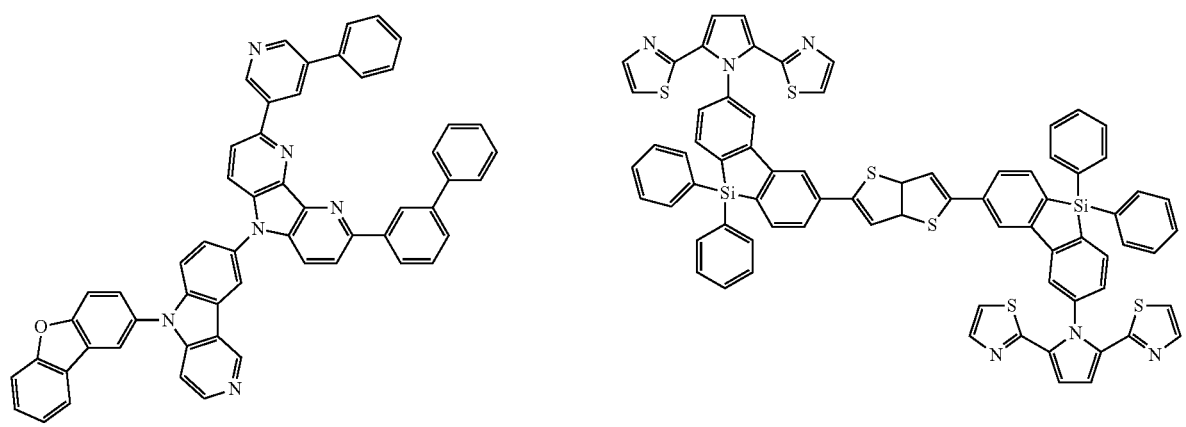
107
108
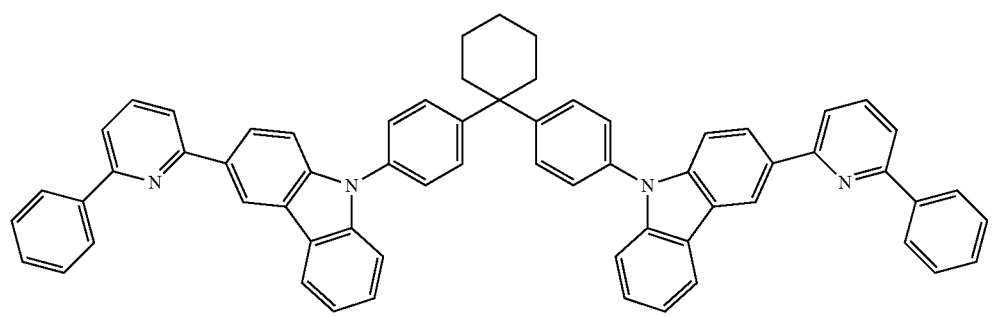
109

[Chemical Formula 60]
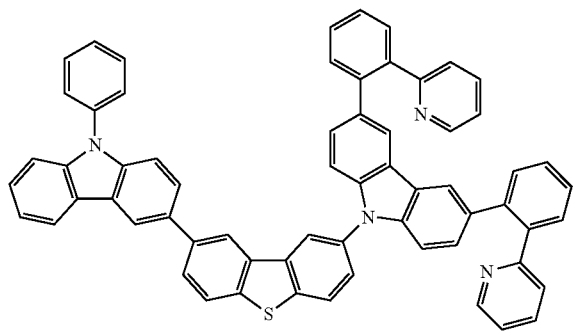
110
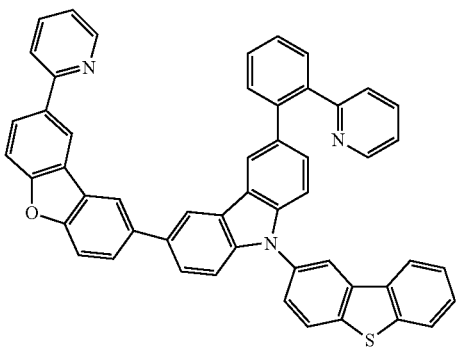
111
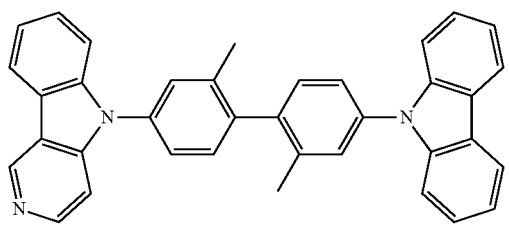
112
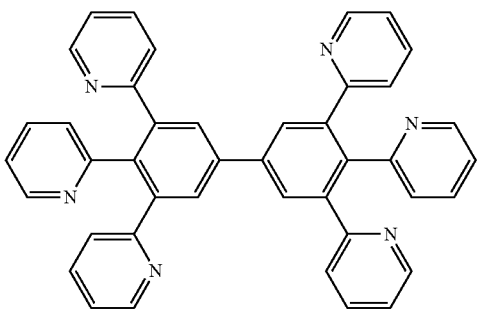
113
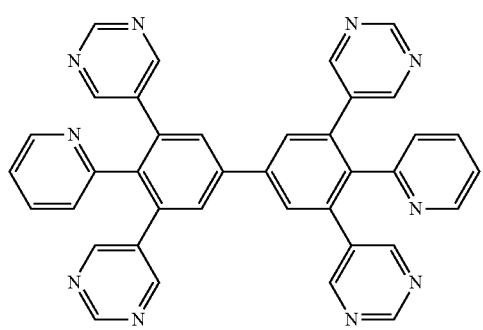
114
[Chemical Formula 61]
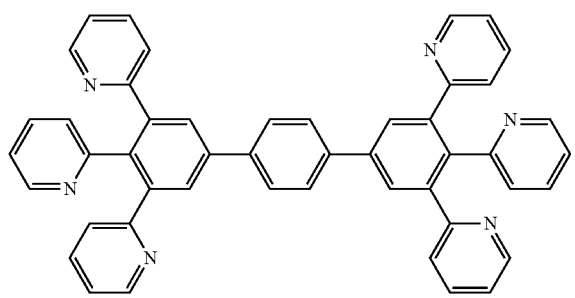
115
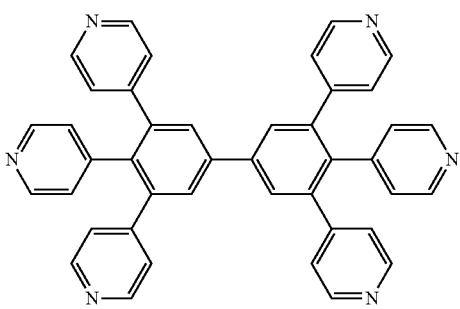
116

-continued
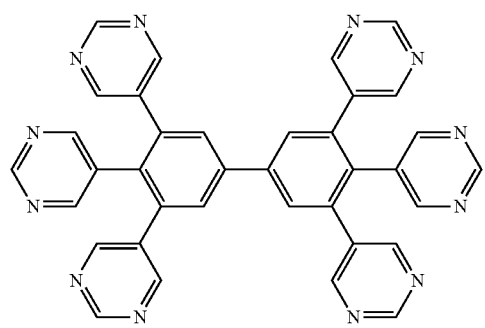
85
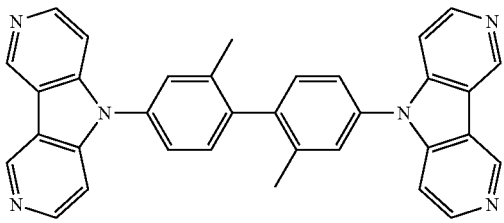
117
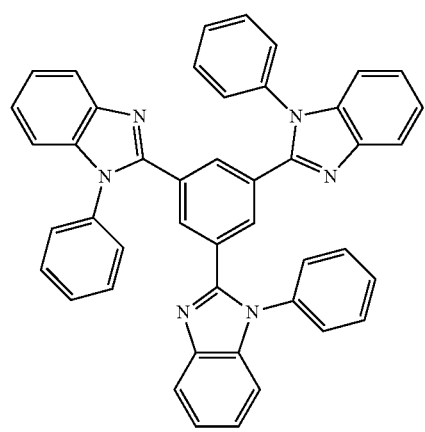
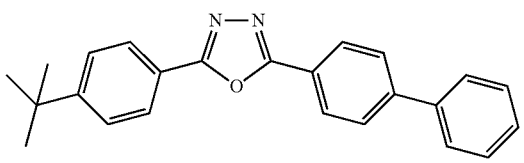
118
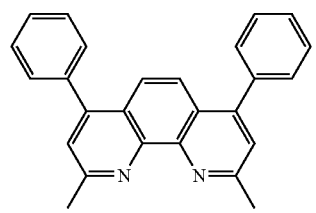
119
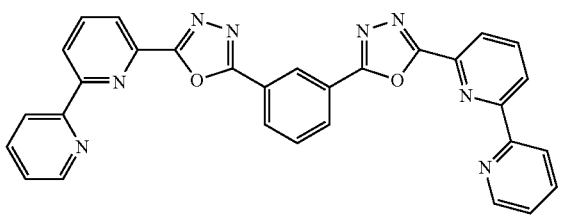
120
121
[Chemical Formula 62]
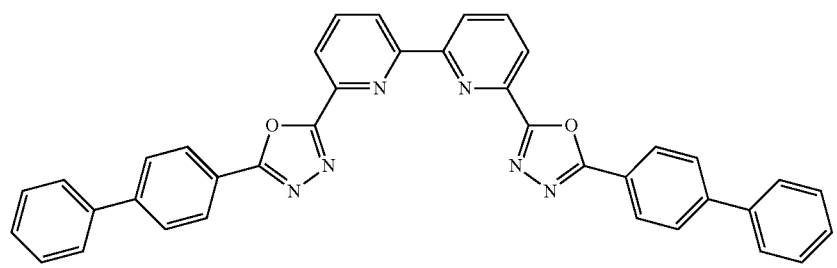
122
123
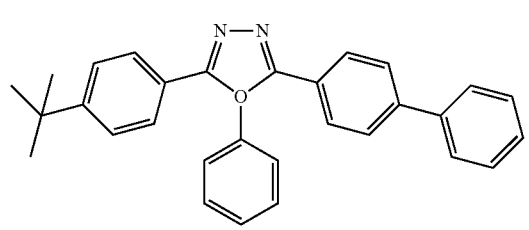
124
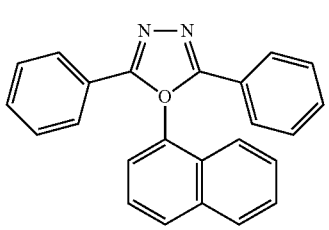
125

126
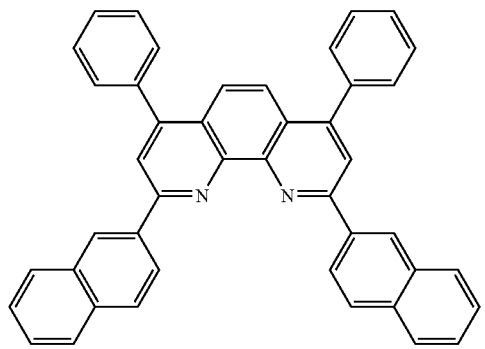
127
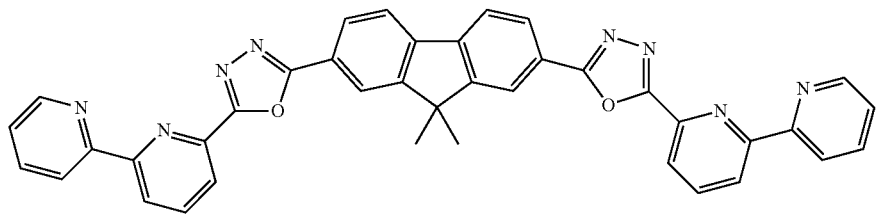
128
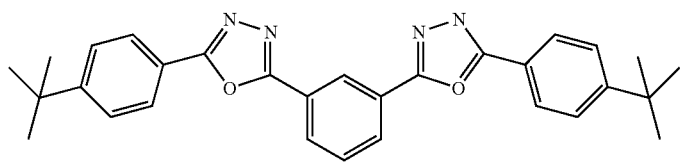
[Chemical Formula 63]
129
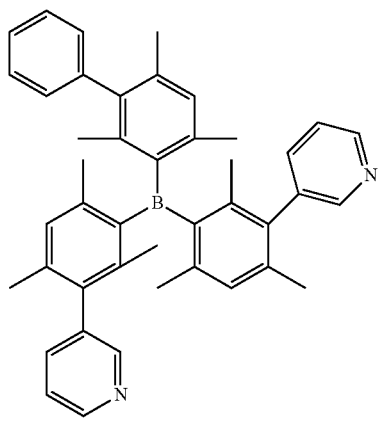
130
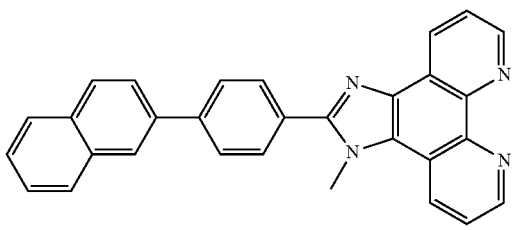

-continued
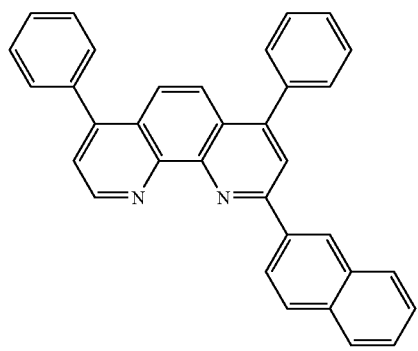
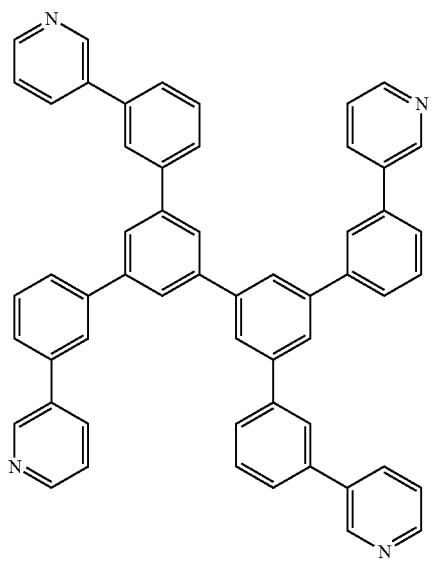
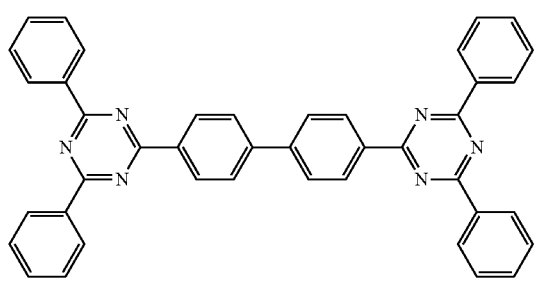
[Chemical Formula 64]
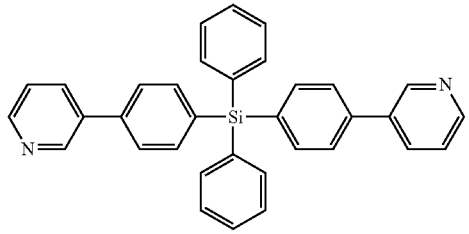
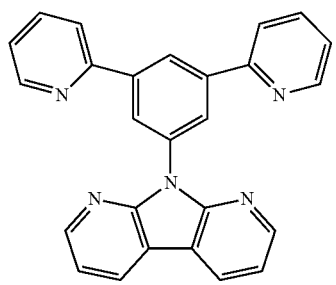
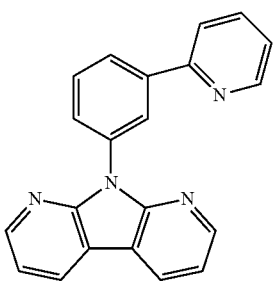
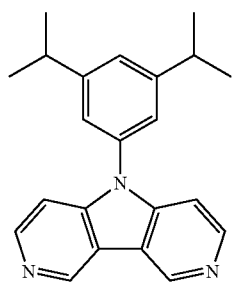
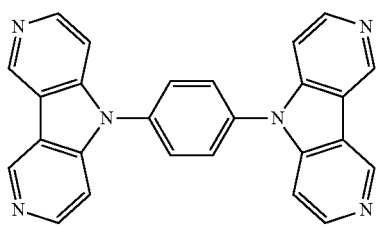

-continued
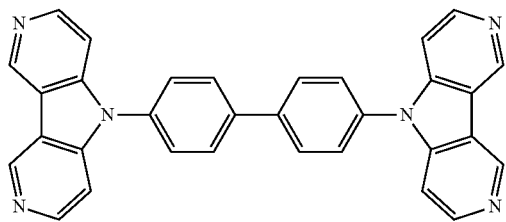
139
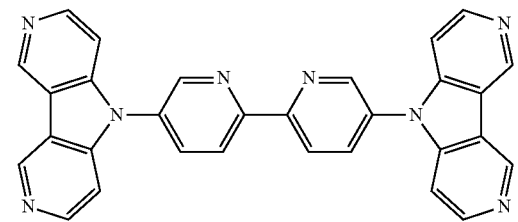
140
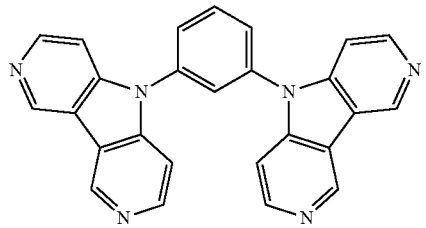
141
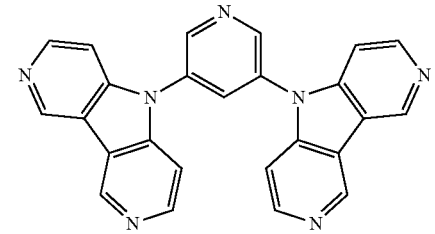
142
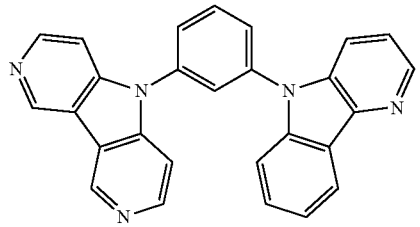
143
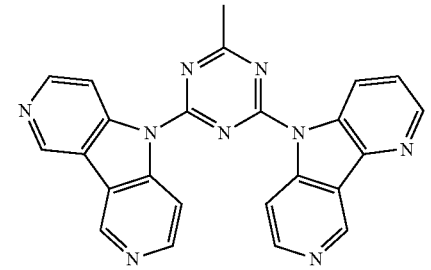
144
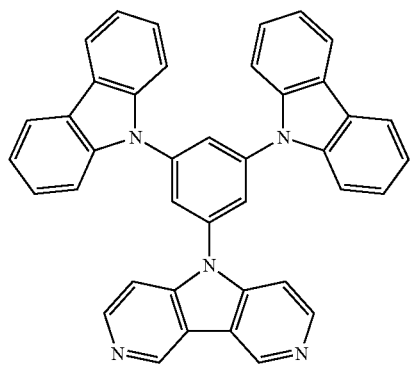
145
[Chemical Formula 65]
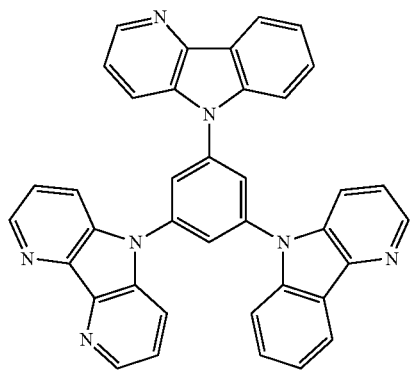
146
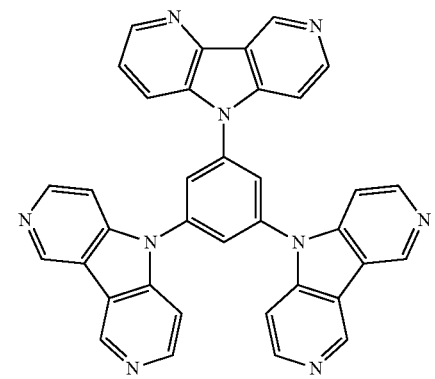
147

93 94
-continued
148 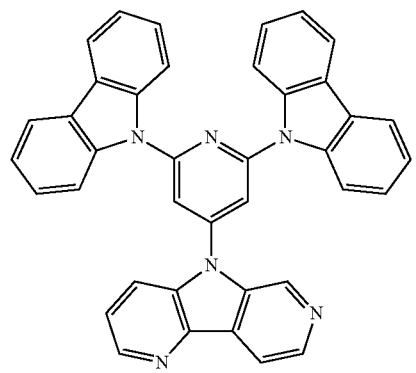 149 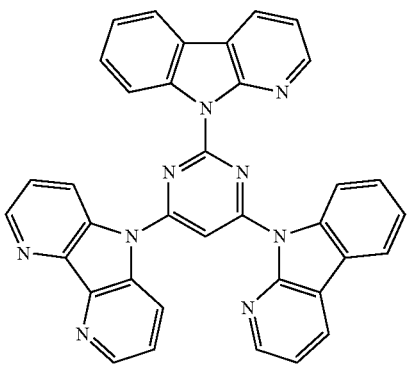
150 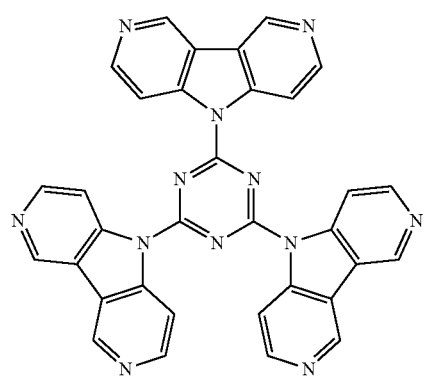 151 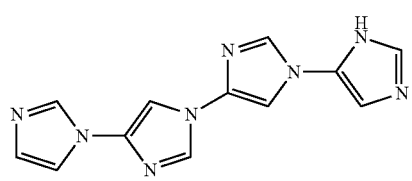
152 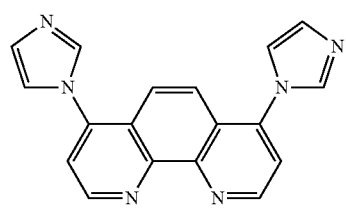 153 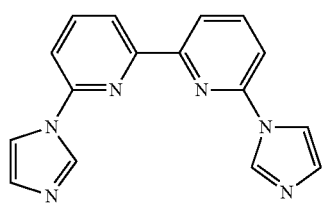
[Chemical Formula 66]
154 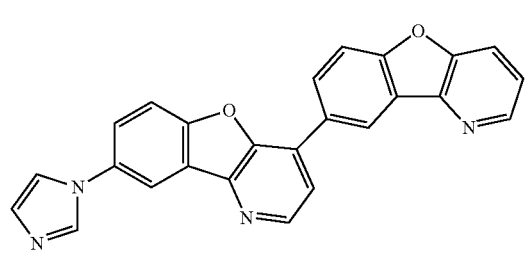 155 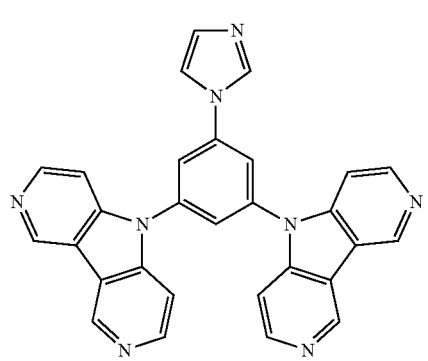

-continued
156 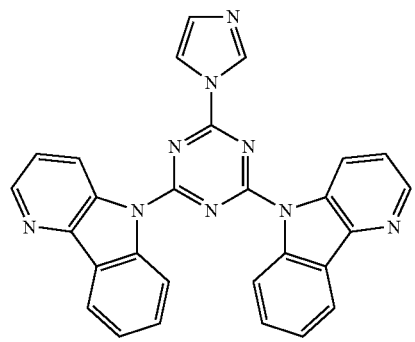
157 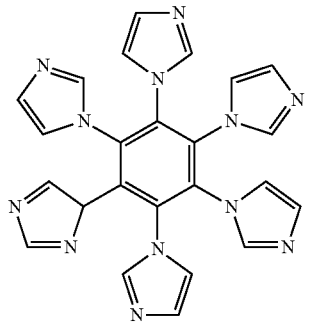
158 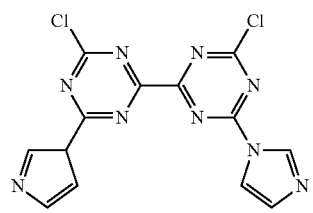
159 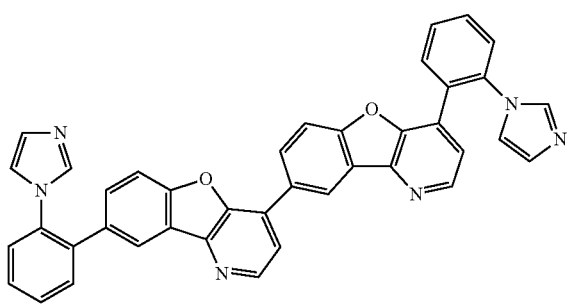
160 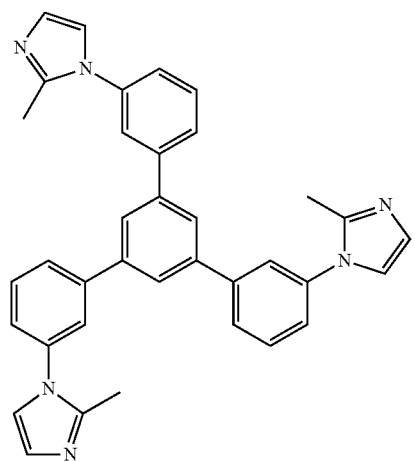
161 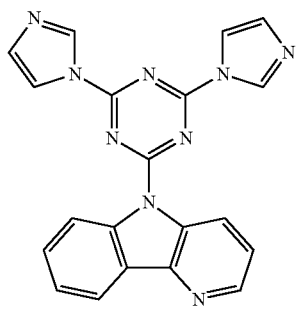
[Chemical Formula 67]
162 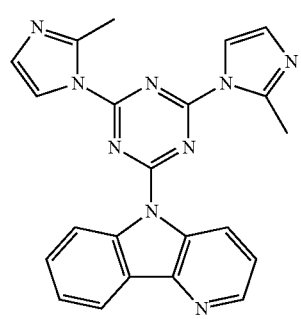
163 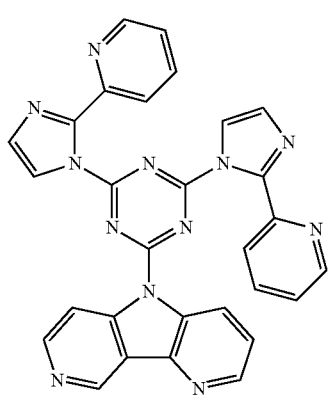

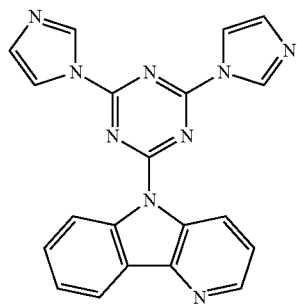
164
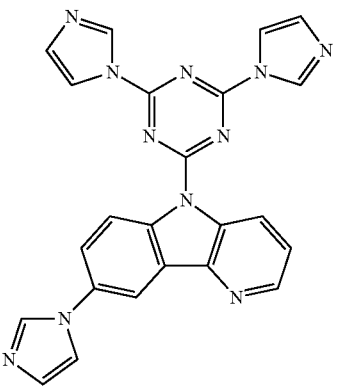
165
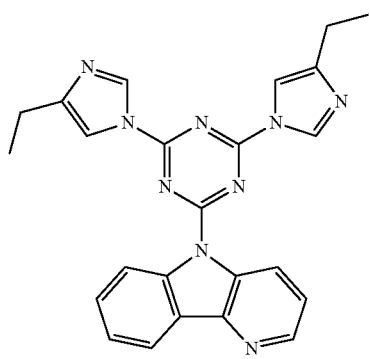
166
[Examples of Synthesis of Compounds]
Hereinafter, a specific example of synthesis of compound 5 will be shown as a non-limiting example of synthesis of a typical compound.
Synthesis of compound 5
[Chemical Formula 68]
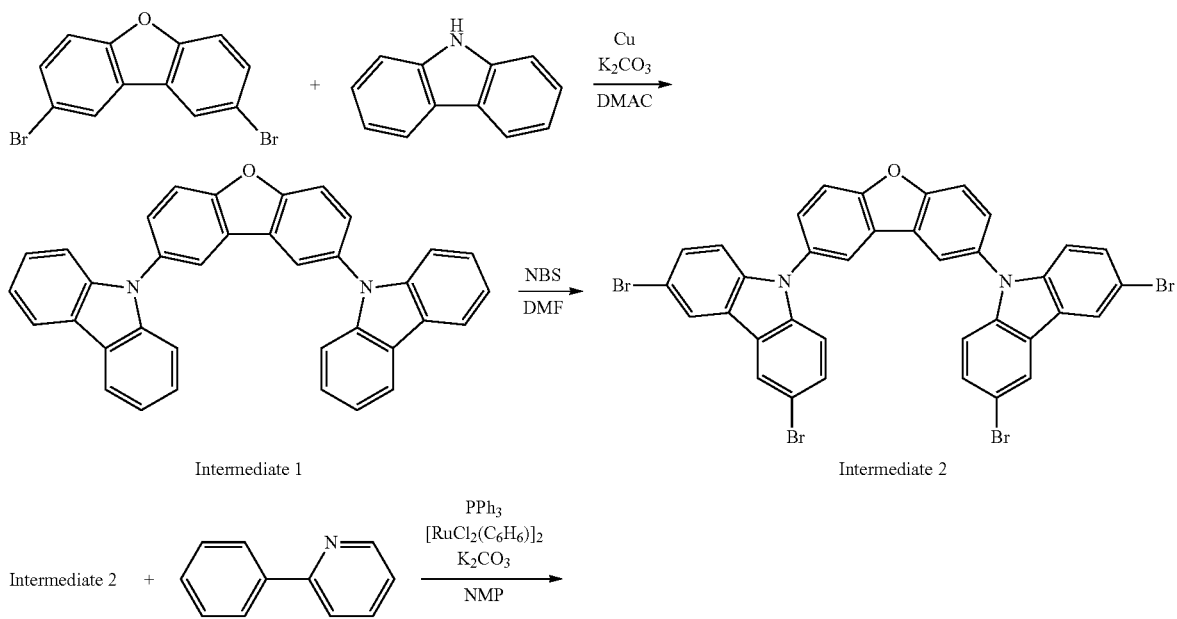

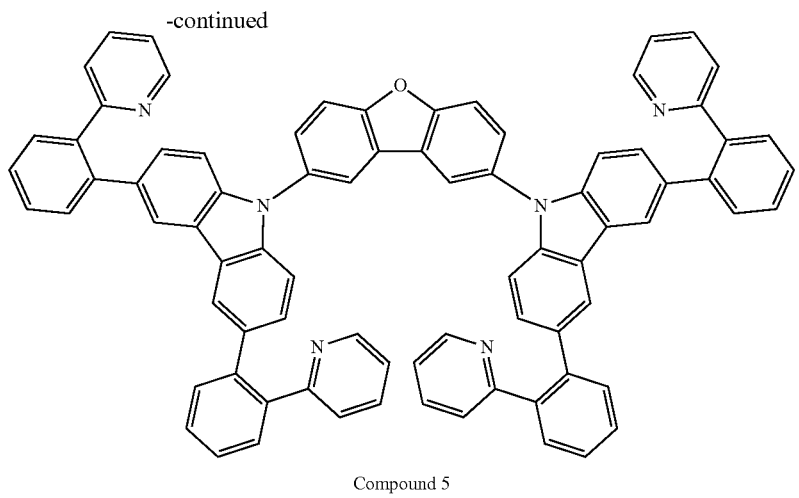

Compound 5

Step 1: (Synthesis of Intermediate 1)

Under a nitrogen atmosphere, 2,8-dibromodibenzofuran (1.0 mole), carbazole (2.0 moles), copper powder (3.0 moles), potassium carbonate (1.5 moles) were mixed in 300 ml of DMAc (dimethylacetamide) and stirred at 130° C. for 24 hours. After the resulting reaction liquid was cooled to room temperature, 1 L of toluene was added to the liquid. The mixture was washed three times with distilled water, and the solvent was removed from the washed product by distillation under a reduced pressure atmosphere. The residue was purified by silica gel flash chromatography (n-heptane:toluene=4:1 to 3:1) to give intermediate 1 with a yield of 85%.

Step 2: (Synthesis of Intermediate 2)

At room temperature, intermediate 1 (0.5 moles) was dissolved in 100 ml of DMF (dimethylformamide) under the atmosphere, and NBS (N-bromosuccinimide) (2.0 moles) was added and stirred at room temperature overnight. The resulting precipitate was separated by filtration and washed with methanol to give intermediate 2 with a yield of 92%.

Step 3: (Synthesis of Compound 5)

Under a nitrogen atmosphere, intermediate 2 (0.25 moles), 2-phenylpyridine (1.0 mole), a ruthenium complex $[(\eta_6\text{-}C_6H_6)RuCl_2]_2$ (0.05 moles), triphenylphosphine (0.2 moles), and potassium carbonate (12 moles) were mixed in 3 L of NMP (N-methyl-2-pyrrolidone) and stirred at 140° C. overnight.

After the reaction liquid was cooled to room temperature, 5 L of dichloromethane was added, and the reaction liquid was filtered. The solvent was then removed from the filtrate by distillation under a reduced pressure atmosphere (800 Pa, 80° C.). The residue was purified by silica gel flash chromatography ($CH_2Cl_2$:$Et_3N$=20:1 to 10:1).

Under a reduced pressure atmosphere, the solvent was removed from the purified product by distillation. The residue was then dissolved again in dichloromethane and washed three times with water. The washed product was dried over anhydrous magnesium sulfate. The solvent was removed from the dried product by distillation under a reduced pressure atmosphere, so that compound 5 was obtained with a yield of 68%.

[Method for Deposition of Nitrogen-Containing Layer 1a]

The nitrogen-containing layer 1a described above may be deposited on the substrate 11. In this case, the deposition method may be a method using a wet process such as application, ink-jetting, coating, or dipping, or a method using a dry process such as vapor deposition (such as resistive heating or electron beam deposition), sputtering, or CVD. In particular, vapor deposition is preferably used.

Particularly when a plurality of compounds are used to form the nitrogen-containing layer 1a, codeposition is preferably used in which the plurality of compounds are simultaneously supplied from a plurality of deposition sources. When the compound used is a polymer material, an application method is preferably used. In this case, a coating liquid including a solution of the compound in a solvent is used. The compound may be dissolved in any solvent. When a plurality of compounds are used to form the nitrogen-containing layer 1a, a solvent capable of dissolving the plurality of compounds may be used to form a coating liquid.

<Electrode Layer 1b>

The electrode layer 1b includes silver as a main component and an additive element. The electrode layer 1b is deposited adjacent to the nitrogen-containing layer 1a. The additive element used to form the electrode layer 1b is specifically a metal element selected from elements that can be uniformly dissolved with silver (Ag) to form a solid solution. Additive elements with such features include aluminum (Al), gold (Au), indium (In), copper (Cu), palladium (Pd), and platinum (Pt). The electrode layer 1b includes at least one of these elements.

The concentration of the additive element in the electrode layer 1b should be in the range of 0.01 to 10.0 at. %.

The electrode layer 1b described above may have a multilayer structure that includes two or more separate alloy layers including silver as a main component and the additive element and stacked as needed. The electrode layer 1b may be a single layer or a multilayer structure, in which the single layer or each layer of the electrode layer 1b may contain two or more different additive elements.

The electrode layer 1b preferably has a thickness in the range of 4 to 12 nm. Preferably, when the thickness is 12 nm or less, absorption or reflection by the electrode layer 1b can be kept low, so that the light transmittance of the layer 1b can be maintained. When the thickness is 4 nm or more, the electrical conductivity of the layer is also ensured.

The electrode layer 1b described above can be deposited by a method using a wet process such as application, ink-jetting, coating, or dipping or by a method using a dry process such as vapor deposition (such as resistive heating or electron beam deposition), sputtering, or CVD.

For example, the electrode layer 1b may be deposited using sputtering. In this case, a sputtering target including silver (Ag) as a main material and an additive element at a concentration adjusted in advance may be provided and used in the sputtering process.

Particularly when aluminum (Al), gold (Au), or indium (In) is used as the additive element, the electrode layer 1b should be formed using vapor deposition. In this case, silver (Ag) and any of these additive elements are co-vapor-deposited. In this process, the additive element deposition rate and the silver (Ag) deposition rate may each be adjusted so that the concentration of the additive element relative to silver (Ag) as the main material can be controlled when the vapor deposition is performed.

The electrode layer 1b deposited on the nitrogen-containing layer 1a is characterized by having sufficient electrical conductivity without being subjected to a high-temperature annealing treatment or other treatments after the deposition. If necessary, however, the electrode layer 1b may be subjected to a high-temperature annealing treatment or other treatments after the deposition.

In this way, the electrode layer 1b is deposited adjacent to the nitrogen-containing layer 1a to form the transparent electrode 1 having a multilayer structure. The top of the electrode layer 1b of the transparent electrode 1 may be covered with a protective film, or another electrically-conductive layer may be formed on the top of the electrode layer 1b. In this case, the protective film and the electrically-conductive layer should preferably be optically transparent so that the transparent electrode 1 can remain optically transparent. An optional layer may also be provided under the nitrogen-containing layer 1a, in other words, between the nitrogen-containing layer 1a and the substrate 11.

<Advantageous Effects of Transparent Electrode 1>

The transparent electrode 1, configured as described above, includes the nitrogen-containing layer 1a including a nitrogen atom-containing compound; and the electrode layer 1b including silver as a main component and provided adjacent to the nitrogen-containing layer 1a. Therefore, in the process of forming the electrode layer 1b adjacent to the nitrogen-containing layer 1a, silver atoms used to form the electrode layer 1b interact with the nitrogen atom-containing compound in the nitrogen-containing layer 1a, so that the silver atoms are reduced in diffusion length at the surface of the nitrogen-containing layer 1a and thus inhibited from aggregating. Therefore, a thin silver film can be formed in a monolayer growth mode (Frank van der Merwe (FM) mode) although in general, silver can easily form isolated islands due to nucleation growth (Volumer Weber (VW) mode). Thus, the electrode layer 1b can be obtained with a uniform thickness even when it has a small thickness.

In particular, the effective lone pair content [n/M] is used as an index to the stability of the ability of silver in the electrode layer 1b to bond the nitrogen-containing layer 1a, and a compound with an effective lone pair content of $2.0 \times 10^{-3}$ or more ($2.0 \times 10^{-3} \leq [n/M]$) is used to form the nitrogen-containing layer 1a. This makes it possible to form the nitrogen-containing layer 1a capable of reliably producing the effect of "inhibiting the aggregation of silver." As described in detail in Examples below, this has also been demonstrated from the fact that a very thin electrode layer 1b with a thickness of 6 nm capable of being measured for sheet resistance is formed on such a nitrogen-containing layer 1a.

In addition, the electrode layer 1b including silver (Ag) as a main component particularly contains at least one of aluminum (Al), gold (Au), indium (In), copper (Cu), palladium (Pd), and platinum (Pt), which are elements capable of forming a solid solution with silver (Ag). This allows the electrode layer 1b to include a solid solution in which silver (Ag) and any of these additive elements are dissolved uniformly, so that the migration of silver (Ag) is suppressed in the electrode layer 1b. Therefore, the degradation of the film quality is prevented, which would otherwise be caused by the migration of silver (Ag) in the electrode layer 1b. In addition, when the electrode layer 1b is formed by adding any of these solid solution-forming elements to silver (Ag), the oxidation or sulfuration of the electrode layer 1b is also prevented.

Thus it is ensured that the electrode layer 1b in the transparent electrode 1 can be thin so that it will reliably have optical transparency, and can also have uniform thickness so that it will have reliable conductivity. In addition, the suppression of the migration also makes it possible to maintain such optical transparency and conductivity. Therefore, the transparent electrode 1 including silver can have both higher conductivity and higher optical transparency and also have higher reliability.

The transparent electrode 1 having these features can be rare metal indium (In)-free and thus low cost. The transparent electrode 1 having these features can also be free of any chemically-unstable materials such as ZnO and thus have high long-term reliability.

<<2. Applications of Transparent Electrode>>

The transparent electrode 1 configured as described above can be used in a variety of electronic devices. Examples of electronic devices include organic electroluminescent devices, LEDs (light-emitting diodes), liquid crystal devices, solar cells, touch panels, etc. In these electronic devices, the transparent electrode 1 can be used as an electrode member required to have optical transparency.

Hereinafter, embodiments of organic electroluminescent devices each including the transparent electrode as an anode or a cathode will be described as an example of application.

<<3. First Example of Organic Electroluminescent Device (Top Emission Type)>>

<Structure of Organic Electroluminescent Device EL-1>

Figure 7:
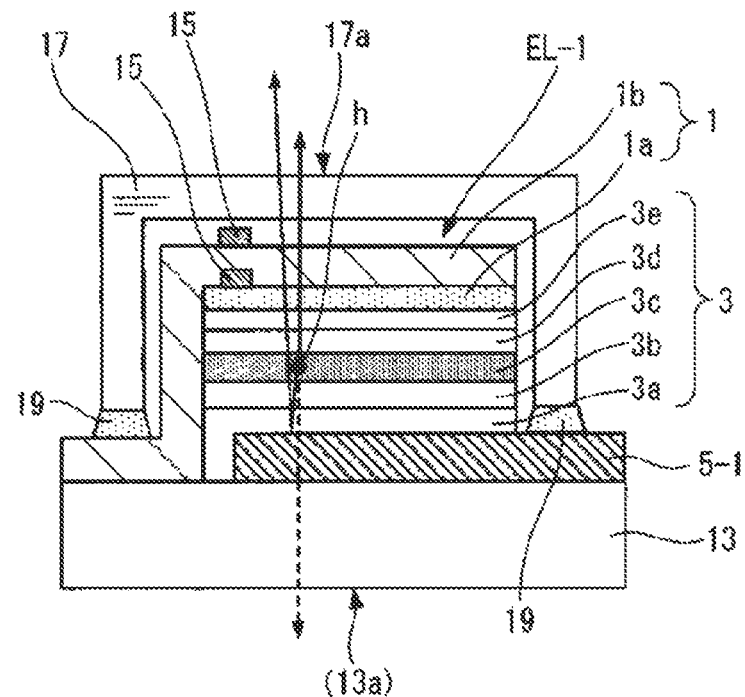
FIG. 7 is a cross-sectional view illustrating the structure of a first example of an organic electroluminescent device including a transparent electrode according to the present invention.

FIG. 7 is a cross-sectional view showing the structure of a first example of an organic electroluminescent device including the transparent electrode 1 of the present invention. Hereinafter, the structure of the organic electroluminescent device will be described with reference to the drawing.

The organic electroluminescent device EL-1 shown in FIG. 7 is provided on a substrate 13 and includes an counter electrode 5-1, a light-emitting functional layer 3 including an organic material and other materials, and the transparent electrode 1, which are stacked in this order on the substrate 13. The organic electroluminescent device EL-1 is characterized by having the transparent electrode 1 of the present invention described above. Therefore, the organic electroluminescent device EL-1 is formed as a top emission structure, in which emitted light (hereinafter expressed as emitted light h) is extracted from at least a side opposite to the substrate 13.

The overall layer structure of the organic electroluminescent device EL-1 is not restricted and may be a common layer structure. In this embodiment, the transparent electrode 1 is disposed on the cathode side so that the electrode layer 1b mainly functions as a cathode, while the counter electrode 5-1 functions as an anode.

Typical device structures for the organic electroluminescent device EL-1 include, but are not limited to, the following structures.
(1) Anode/light-emitting layer/cathode
(2) Anode/light-emitting layer/electron transport layer/cathode
(3) Anode/hole transport layer/light-emitting layer/cathode
(4) Anode/hole transport layer/light-emitting layer/electron transport layer/cathode
(5) Anode/hole transport layer/light-emitting layer/electron transport layer/electron injection layer/cathode
(6) Anode/hole injection layer/hole transport layer/light-emitting layer/electron transport layer/cathode
(7) Anode/hole injection layer/hole transport layer/(electron-blocking layer/) light-emitting layer/(hole-blocking layer/) electron transport layer/electron injection layer/cathode Among them, structure (7) is preferably used although any other structure may be used.

As an example, this embodiment shows a layer structure including a hole injection layer $3a$, a hole transport layer $3b$, a light-emitting layer $3c$, an electron transport layer $3d$, and an electron injection layer $3e$, stacked in this order on the counter electrode 5-1 as an anode, in which the light-emitting layer $3c$ including at least an organic material is an essential component.

In the present invention, the light-emitting layer may have a monolayer or multilayer structure. When a plurality of light-emitting layers are provided, a non-light-emitting intermediate layer may be provided between the respective light-emitting layers.

If necessary, a hole-blocking layer (also called a hole barrier layer) or an electron injection layer (also called a cathode buffer layer) may be provided between the light-emitting layer and the cathode, and an electron-blocking layer (also called an electron barrier layer) or a hole injection layer (also called an anode buffer layer) may be provided between the light-emitting layer and the anode.

In the present invention, the electron transport layer is a layer having the function of transporting electrons. In a broad sense, the electron transport layer also includes an electron injection layer or a hole-blocking layer. The electron transport layer may also be a multilayer structure.

In the present invention, the hole transport layer is a layer having the function of transporting holes. In abroad sense, the hole transport layer also includes a hole injection layer or an electron-blocking layer. The hole transport layer may also be a multilayer structure.

In the above typical device structure, the light-emitting functional layer 3, exclusive of the anode and the cathode, is also referred to as the "organic layer." In the light-emitting functional layer 3, for example, the electron injection layer may include an inorganic material.

In the transparent electrode 1 provided to form the cathode, the nitrogen-containing layer $1a$ may also serve as an electron injection layer or as both an electron transport layer and an electron injection layer.

(Tandem Structure)

The organic electroluminescent device according to the present invention may be a tandem structure device in which a plurality of light-emitting units (light-emitting functional layers) each including a light-emitting functional layer including at least one light-emitting layer are stacked between the anode and the cathode.

A typical example of the tandem structure device may have the following structure: [anode/first light-emitting unit/intermediate layer/second light-emitting unit/intermediate layer/third light-emitting unit/cathode]

In this structure, the first, second, and third light-emitting units may be the same or different. Alternatively, two of them may be the same and differ from the remaining one.

Two or more light-emitting units may be stacked directly on each other or stacked with an intermediate layer interposed therebetween. The intermediate layer is also generally called an intermediate electrode, an intermediate conductive layer, a charge generation layer, an electron extraction layer, a connection layer, or an intermediate insulating layer, which may include any known material as long as it forms a layer having the function of supplying electrons to the adjacent layer on the anode side and supplying holes to the adjacent layer on the cathode side.

Examples of materials that may be used to form the intermediate layer include, but are not limited to, ITO (indium tin oxide), IZO (indium zinc oxide), $ZnO_2$, TiN, ZrN, HfN, $TiO_x$, $VO_x$, CuI, InN, GaN, $CuAlO_2$, $CuGaO_2$, $SrCu_2O_2$, $LaB_6$, $RuO_2$, Al, and other conductive inorganic compound layers, $Au/Bi_2O_2$ and other two-layer films, $SnO_2/Ag/SnO_2$, ZnO/Ag/ZnO, $Bi_2O_2/Au/Bi_2O_3$, $TiO_2/TiN/TiO_2$, $TiO_2/ZrN/TiO_2$, and other multilayer films, fullerenes such as C60, oligothiophene and other conductive organic materials, metallophthalocyanines, metal-free phthalocyanines, metalloporphyrins, metal-free porphyrins, and other conductive organic compounds.

Preferred examples of the structure of the light-emitting unit (light-emitting functional layer) include, but are not limited to, structures obtained by excluding the anode and the cathode from typical device structures (1) to (7) listed above. When the light-emitting unit (light-emitting functional layer) closest to the cathode has an electron injection layer or an electron transport layer, the nitrogen-containing layer $1a$ may also serve as any of these layers.

Examples of the tandem organic electroluminescent device include, but are not limited to, the device structures and components described in U.S. Pat. No. 6,337,492, U.S. Pat. No. 7,420,203, U.S. Pat. No. 7,473,923, U.S. Pat. No. 6,872,472, U.S. Pat. No. 6,107,734, U.S. Pat. No. 6,337,492, WO 2005/009087 A, JP 2006-228712 A, JP 2006-24791 A, JP 2006-49393 A, JP 2006-49394 A, JP 2006-49396 A, JP 2011-96679 A, JP 2005-340187 A, JP 4711424 B1, JP 3496681 B1, JP 3884564 B1, JP 4213169 B1, JP 2010-192719 A, JP 2009-076929 A, JP 2008-078414 A, JP 2007-059848 A, JP 2003-272860 A, JP 2003-045676 A, and WO 2005/094130 A.

Each principal layer of the above organic electroluminescent device EL-1 will be more specifically described in the following order: the substrate 13, the transparent electrode 1, the counter electrode 5-1, each layer of the light-emitting functional layer 3, methods for forming the light-emitting functional layer 3, an auxiliary electrode 15, and a transparent sealant 17. Subsequently, a method for manufacturing the organic electroluminescent device EL-1 will be described.

[Substrate 13]

The substrate 13 may include the same material as the substrate on which the transparent electrode 1 of the present invention described above is provided. However, the organic electroluminescent device EL-1 may be of a double-side emission type in which emitted light h is also extracted from the counter electrode 5-1 side, and in this case, a transparent substrate having optical transparency should be selected from the substrates listed above and used.

[Transparent Electrode 1 (Cathode Side)]

The transparent electrode 1 is the transparent electrode 1 of the present invention described above including the nitrogen-containing layer $1a$ and the electrode layer $1b$, which are sequentially deposited from the light-emitting functional layer 3 side. In this structure, the electrode layer 1b of the transparent electrode 1 substantially serves as a cathode. In the organic electroluminescent device EL-1, the nitrogen-containing layer 1a including an organic material is disposed between the light-emitting functional layer 3 and the electrode layer 1b used as a substantial cathode. In the first example, therefore, the nitrogen-containing layer 1a of the transparent electrode 1 may also be counted as a layer forming part of the light-emitting functional layer 3.

In such a case, the nitrogen-containing layer 1a includes a compound having electron transport properties or electron injection properties, which is selected from the above compounds having an effective lone pair content [n/M] in the specified range. Alternatively, in such a case, the nitrogen-containing layer 1a may include a compound having electron transport or injection properties and a compound having a certain level of effective lone pair content [n/M], which are mixed in such a way that the nitrogen-containing layer 1a itself has an effective lone pair content [n/M] in the specified range. The drawing shows a structure in which the nitrogen-containing layer 1a is provided only on the light-emitting functional layer 3. Alternatively, as long as the light-emitting function is not affected, the nitrogen-containing layer 1a may be provided over the surface adjacent to the electrode layer 1b so that the whole of the electrode layer 1b can contribute to the electrical conductivity. The nitrogen-containing layer 1a may also be a multilayer structure. In this case, an about 5 nm-thick interfacial layer of the nitrogen-containing layer 1a on the electrode layer 1b side is preferably formed so as to have an effective lone pair content [n/M] in the specified range. On the other hand, the layer of the remaining part on the light-emitting functional layer 3 side is preferably formed as an electron transport layer or an electron injection layer including a nitrogen-containing compound.

[Counter Electrode 5-1 (Anode)]

The counter electrode 5-1 is an electrode film provided to function as an anode for supplying holes to the light-emitting functional layer 3. The material suitable as an anode is preferably an electrode material with a high work function (4 eV or more, preferably 4.5 eV or more), such as a metal, an alloy, an electrically-conductive compound, or any mixture thereof. Examples of such an electrode material include metals such as Au, CuI, indium tin oxide (ITO), $SnO_2$, ZnO, and other transparent conductive materials. A material capable of forming an amorphous transparent conductive film, such as IDIXO ($In_2O_3$—ZnO) may also be used.

The anode may be formed by a process that includes forming a thin film of any of these electrode materials by vapor deposition, sputtering, or other methods and patterning the thin film into a desired shape by photolithography. Alternatively, if high patterning accuracy is not necessary (about 100 μm or more), the electrode material may be vapor-deposited or deposited by sputtering through a mask with the desired shape to form a certain pattern.

Alternatively, a material capable of being applied by coating techniques, such as a conductive organic compound may be used. In this case, wet deposition techniques such as printing and coating may also be used. When emitted light is extracted from the anode, the anode preferably has a transmittance of more than 10%, and the sheet resistance of the anode is preferably hundreds of Ω/square or less.

The thickness of the anode is generally selected in the range of 10 nm to 1 μm, preferably in the range of 10 nm to 200 nm, although it depends on the material.

The organic electroluminescent device EL-1 may be of a double-side emission type in which emitted light h is also extracted from the counter electrode 5-1 side. In this case, a conductive material with high optical transparency may be selected from the above conductive materials and used to form the counter electrode 5-1.

[Light-Emitting Layer 3c]

In the present invention, the light-emitting layer 3c is a layer for providing a place where electrons and holes injected from the electrodes or adjacent layers are recombined to form excitons for light emission. The light-emitting part may be inside the light-emitting layer or at the interface between the light-emitting layer and the adjacent layer. In the present invention, the light-emitting layer may have any structure as long as the requirements according to the present invention are satisfied.

As a non-limiting example, the total thickness of the light-emitting layer is preferably adjusted to fall within the range of 2 nm to 5 μm, more preferably within the range of 2 nm to 500 nm, even more preferably within the range of 5 nm to 200 nm so that the film can be uniformly formed, unnecessary high-voltage can be prevented from being applied during light emission, and the stability of luminescent color at the driving current can be improved.

The thickness of the light-emitting layer is also preferably adjusted to fall within the range of 2 nm to 1 μm, more preferably within the range of 2 nm to 200 nm, even more preferably within the range of 3 nm to 150 nm.

The light-emitting layer preferably contains a light-emitting dopant (also referred to as a luminescent dopant compound, a dopant compound, or simply a dopant) and a host compound (also referred to as a matrix material, a light-emitting host compound, or simply a host).

(1) Light-Emitting Dopant

The light-emitting dopant according to the present invention will be described.

The light-emitting dopant is preferably a fluorescence-emitting dopant (also referred to as a fluorescent dopant or a fluorescent compound) or a phosphorescence-emitting dopant (also referred to as a phosphorescent dopant or a phosphorescent compound). In the present invention, at least one light-emitting layer preferably contains a phosphorescence-emitting dopant.

The concentration of the light-emitting dopant in the light-emitting layer may be freely determined based on the specific dopant to be used and the requirements for the device. The light-emitting layer may contain the dopant at a concentration uniform in the thicknesswise direction of the layer, or may have a certain dopant concentration distribution in the thicknesswise direction of the layer.

In the present invention, two or more different light-emitting dopants may be used together, and dopants with different structures may be used together, or a fluorescence-emitting dopant may be used in combination with a phosphorescence-emitting dopant. This makes it possible to obtain any desired luminescent color.

The color of the light emitted from the organic EL device of the present invention or the compound according to the present invention can be determined by measuring the light with a spectral radiance meter CS-2000 (manufactured by Konica Minolta Sensing Co., Ltd.) according to FIG. 4.16 on page 108 of Shin-Hen Shikisai Kagaku Handbook (New Handbook of Color Science) (edited by The Color Science Association of Japan, University of Tokyo Press, 1985) and determining the color from the measurement results based on the CIE chromaticity coordinates.

In the present invention, one or more light-emitting layers also preferably contain two or more light-emitting dopants with different luminescent colors to produce white emission.

Any combination of light-emitting dopants may be used to produce white emission. For example, a combination of blue and orange dopants, a combination of blue, green, and red dopants, or the like may be used.

The white color of the light from the organic EL device of the present invention is preferably such that the chromaticity of the light according to the CIE 1931 color system at 1,000 cd/m$^2$ falls within the region x=0.39±0.09, y=0.38±0.08 when the 2° view angle front luminous is measured by the above method.

(1.1) Phosphorescence-Emitting Dopant

The phosphorescence-emitting dopant according to the present invention (hereinafter also referred to as the "phosphorescent dopant") will be described.

The phosphorescent dopant according to the present invention is such a compound that emission from the excited triplet can be observed. Specifically, the phosphorescent dopant may be defined as a compound that emits phosphorescence at room temperature (25° C.) and has a phosphorescence quantum yield of 0.01 or more at 25° C. The phosphorescence quantum yield is preferably 0.1 or more.

The phosphorescence quantum yield can be measured by the method described on page 398 of The 4th Edition Jikken Kagaku Koza (Handbook of Experimental Chemistry) 7, Bunko (Spectroscopy) II (1992, Maruzen). The phosphorescence quantum yield in a solution can be measured using a variety of solvents. The phosphorescent dopant according to the present invention should have the specified phosphorescence quantum yield (0.01 or more) in any one of such solvents.

There are two principles for light emission from the phosphorescent dopant. One is an energy transfer type, according to which carriers are transported to a host compound and recombined on the host compound, so that the host compound is brought into an excited state, the energy of which is transferred to the phosphorescent dopant so that light is emitted from the phosphorescent dopant. The other is a carrier trap type, according to which carriers are recombined on the phosphorescent dopant serving as a carrier trap, so that light is emitted from the phosphorescent dopant. In both cases, it is required that the energy of the excited state of the phosphorescent dopant be lower than the energy of the excited state of the host compound.

The phosphorescent dopant (which may be used in combination with any other dopant in the present invention) may be appropriately selected from known dopants used in light-emitting layers for organic EL devices.

Examples of known phosphorescent dopants that may be used in the present invention include the compounds described in the literatures shown below.

Red phosphorescent dopants are described in the following literatures: Nature 395, 151 (1998), Appl. Phys. Lett. 78, 1622 (2001), Adv. Mater. 19, 739 (2007), Chem. Mater. 17, 3532 (2005), Adv. Mater. 17, 1059 (2005), WO 2009/100991 A, WO 2008/101842 A, WO 2003/040257 A, US 2006/835,469 A, US 2006/0,202,194 A, US 2007/0,087,321 A, and US 2005/0,244,673 A.

Green phosphorescent dopants are described in the following literatures: Inorg. Chem. 40, 1704 (2001), Chem. Mater. 16, 2480 (2004), Adv. Mater. 16, 2003 (2004), Angew. Chem. Int. Ed. 2006, 45, 7800, Appl. Phys. Lett. 86, 153505 (2005), Chem. Lett. 34, 592 (2005), Chem. Commun. 2906 (2005), Inorg. Chem. 42, 1248 (2003), WO 2009/050290 A, WO 2002/015645 A, WO 2009/000673 A, US 2002/0,034,656 A, U.S. Pat. No. 7,332,232, US 2009/0,108,737 A, US 2009/0,039,776 A, U.S. Pat. No. 6,921,915, U.S. Pat. No. 6,687,266, US 2007/0,190,359 A, US 2006/0,008,670 A, US 2009/0,165,846 A, US 2008/0,015,355 A, U.S. Pat. No. 7,250,226, U.S. Pat. No. 7,396,598, US 2006/0,263,635 A, US 2003/0,138,657 A, US 2003/0,152,802 A, and U.S. Pat. No. 7,090,928.

Blue phosphorescent dopants are described in the following literatures: Angew. Chem. Int. Ed. 47, 1 (2008), Chem. Mater. 18, 5119 (2006), Inorg. Chem. 46, 4308 (2007), Organometallics 23, 3745 (2004), Appl. Phys. Lett. 74, 1361 (1999), WO 2002/002714 A, WO 2006/009024 A, WO 2006/056418 A, WO 2005/019373 A, WO 2005/123873 A, WO 2007/004380 A, WO 2006/082742 A, US 2006/0,251,923 A, US 2005/0,260,441 A, U.S. Pat. No. 7,393,599, U.S. Pat. No. 7,534,505, U.S. Pat. No. 7,445,855, US 2007/0,190,359 A, US 2008/0,297,033 A, U.S. Pat. No. 7,338,722, US 2002/0,134,984 A, U.S. Pat. No. 7,279,704, US 2006/098,120 A, and US 2006/103,874 A.

Phosphorescent dopants with various colors (mainly blue) are described in the following literatures: WO 2005/076380 A, WO 2010/032663 A, WO 2008/140115 A, WO 2007/052431 A, WO 2011/134013 A, WO 2011/157339 A, WO 2010/086089 A, WO 2009/113646 A, WO 2012/020327 A, WO 2011/051404 A, WO 2011/004639 A, WO 2011/073149 A, US 2012/228,583 A, US 2012/212,126 A, JP 2012-069737 A, JP 2012-195554A, JP 2009-114086 A, JP 2003-81988 A, JP 2002-302671 A, and JP 2002-363552 A.

In particular, the phosphorescent dopant is preferably an organometallic complex having Ir as a central metal. The phosphorescent dopant is more preferably a complex having at least one coordination moiety from a metal-carbon bond, a metal-nitrogen bond, a metal-oxygen bond, and a metal-sulfur bond.

Examples of known phosphorescent dopants that may be used in the present invention include, but are not limited to, the following dopants (D1 to D81).

[Chemical Formula 69]

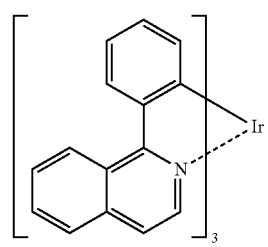

D-1

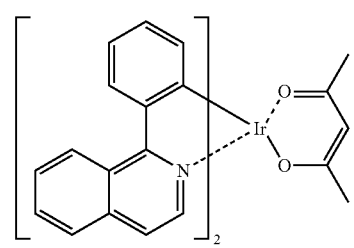

D-2

D-3 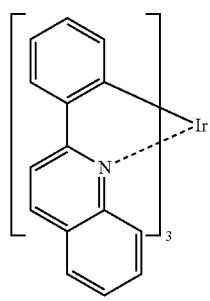
D-4 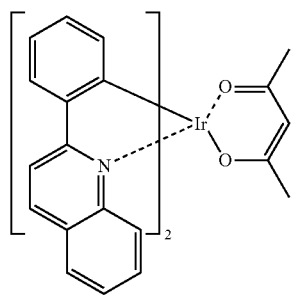
D-5 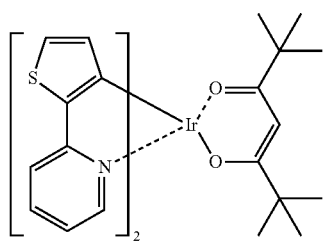
D-6 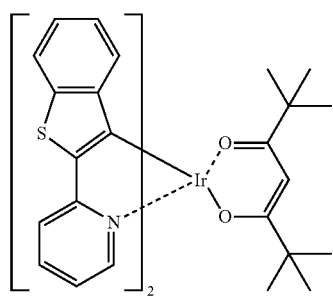
D7 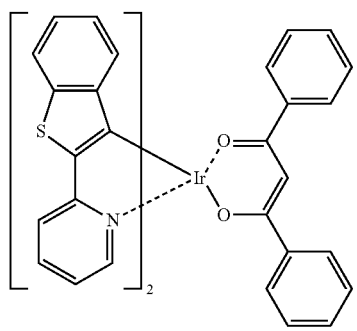
D8 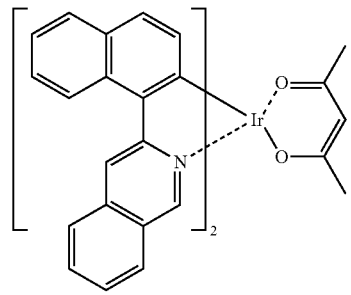
D9 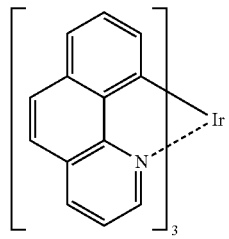
D10 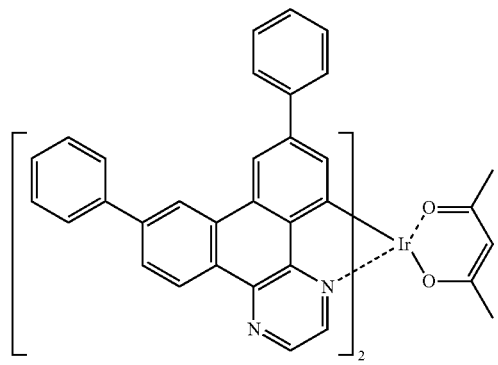
D11 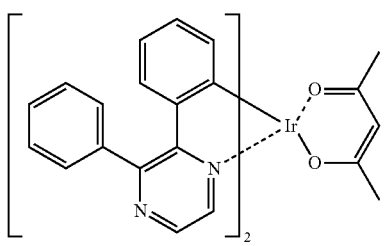
D-12 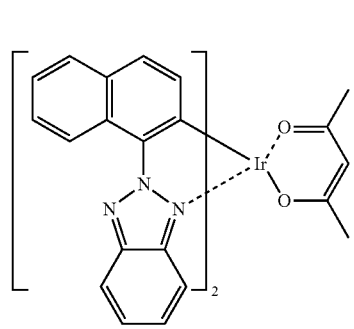

-continued
D-13
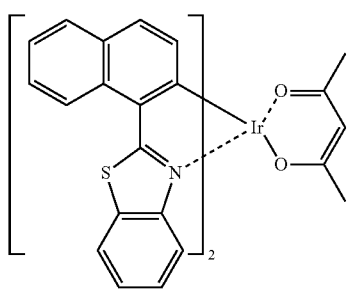
D-14
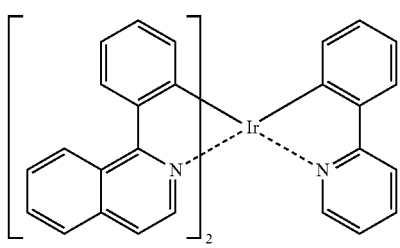
D-15
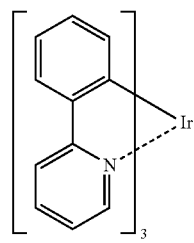
D-16
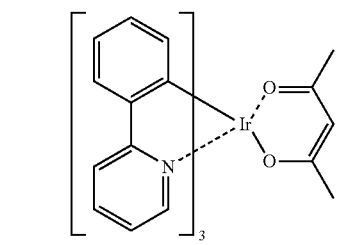
D-17
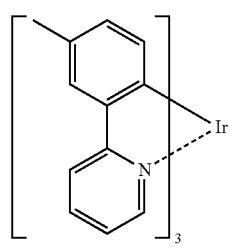
D-18
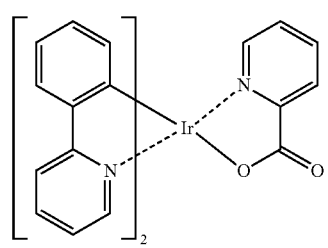
-continued
D-19
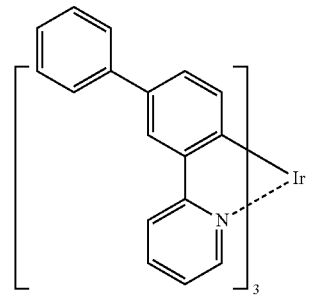
D-20
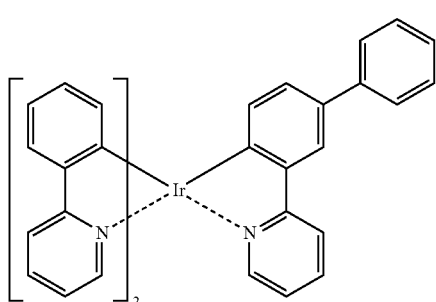
[Chemical Formula 70]
D-21
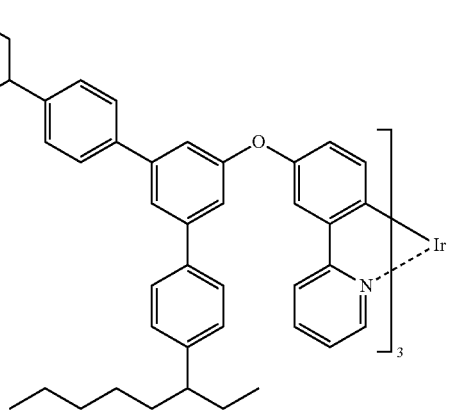
D-22
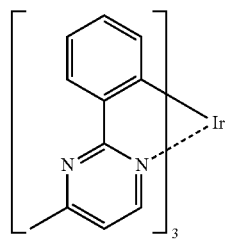
D-23
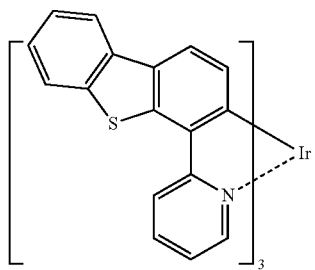

D-24 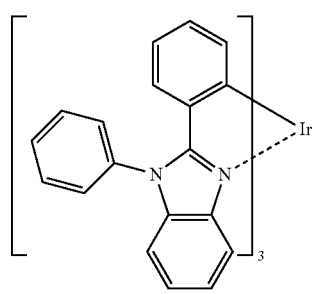
D-25 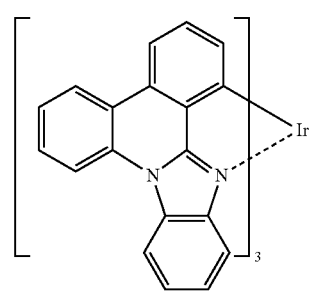
D-26 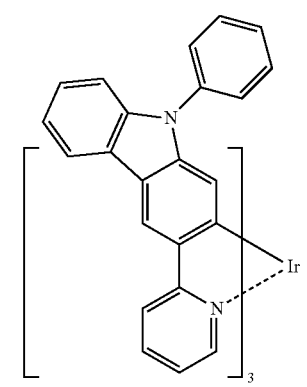
D-27 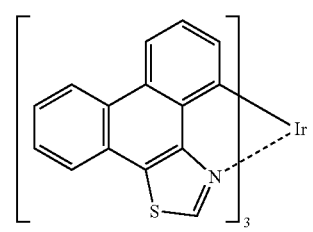
D-28 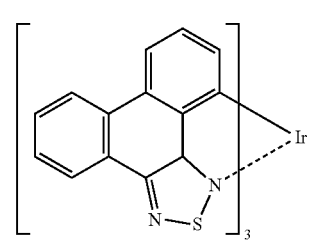
D-29 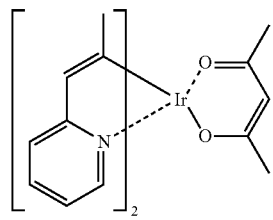
D-30 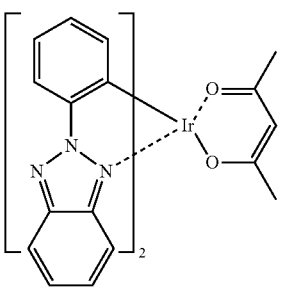
D-31 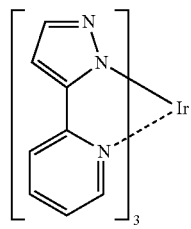
D-32 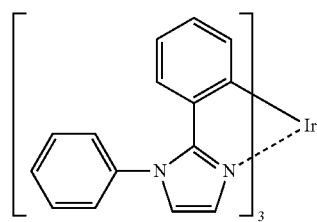
D-33 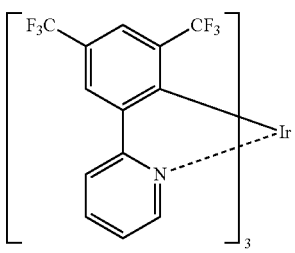
D-34 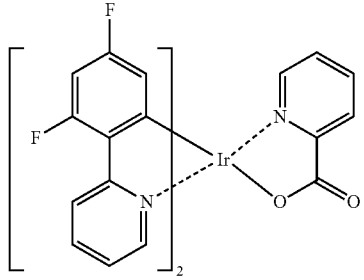

-continued
D-35
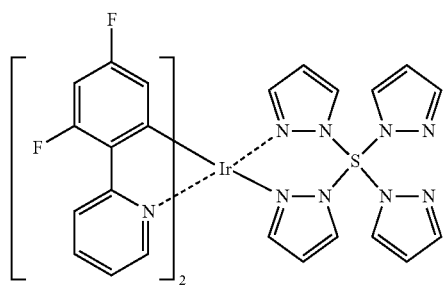
D-36
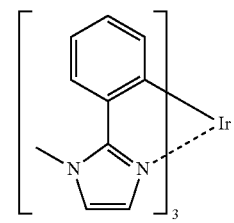
D-37
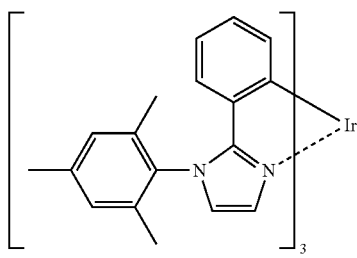
D-38
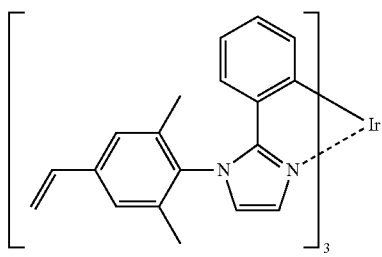
D-39
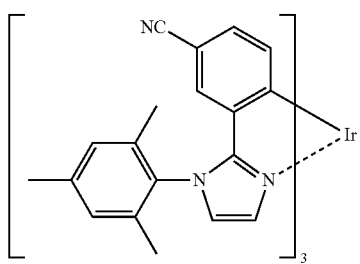
D-40
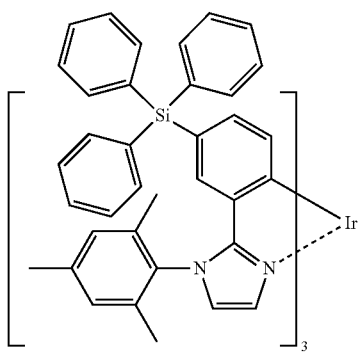
-continued
[Chemical Formula 71]
D-41
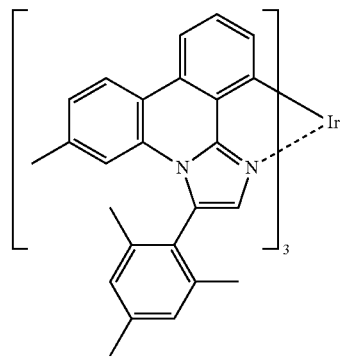
D-42
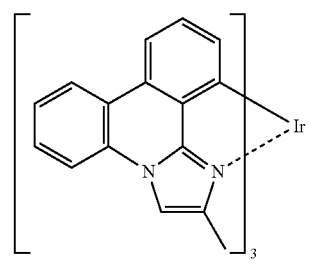
D-43
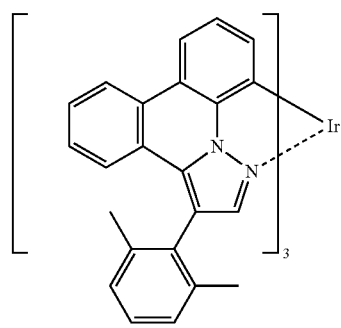
D-44
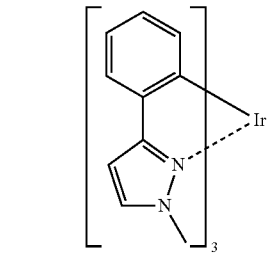
D-45
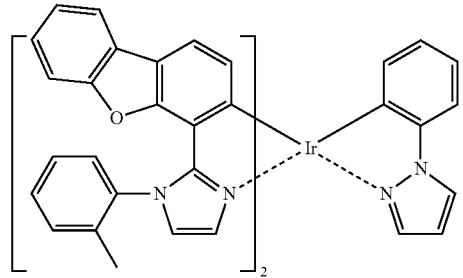

-continued
D-46
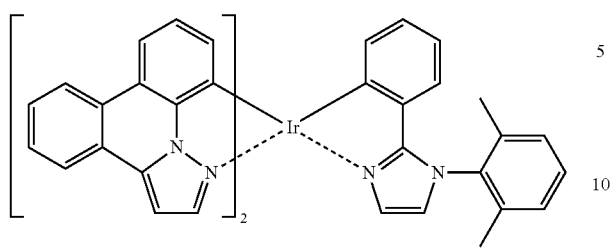
D-47
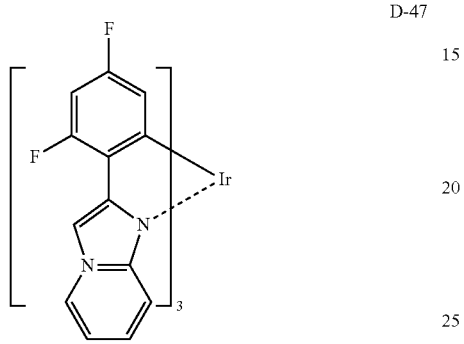
D-48
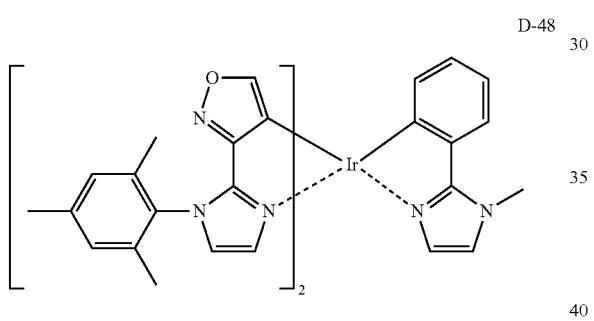
D-49
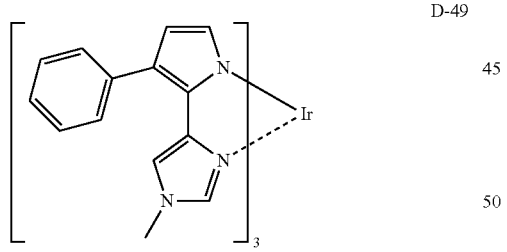
D-50
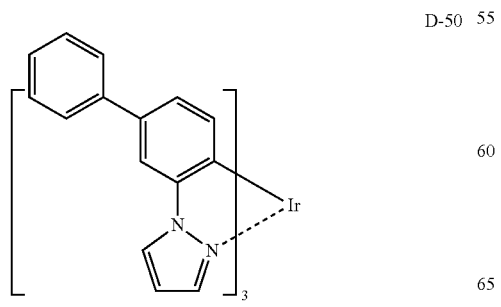
-continued
D-51
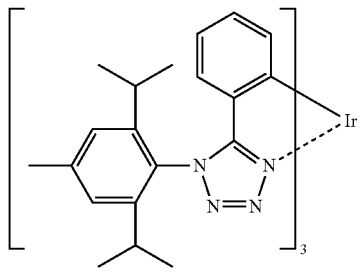
D-52
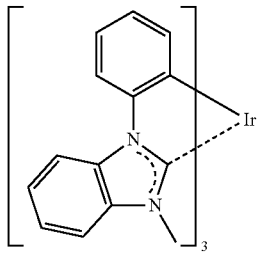
D-53
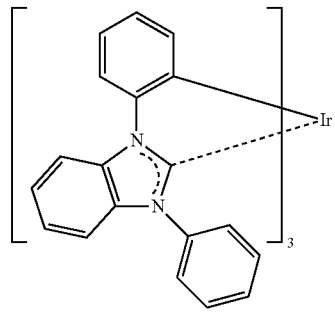
D-54
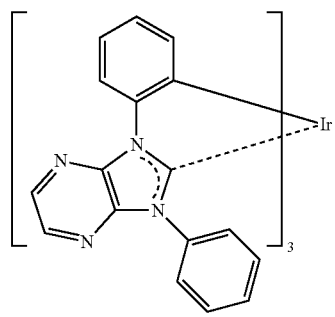
D-55
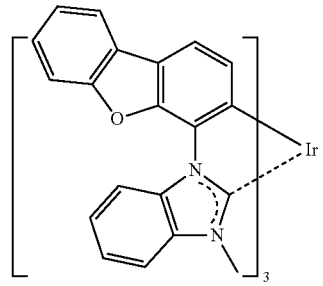

-continued
D-56
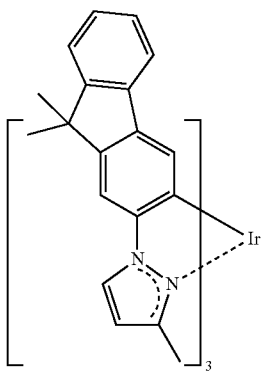
D-57
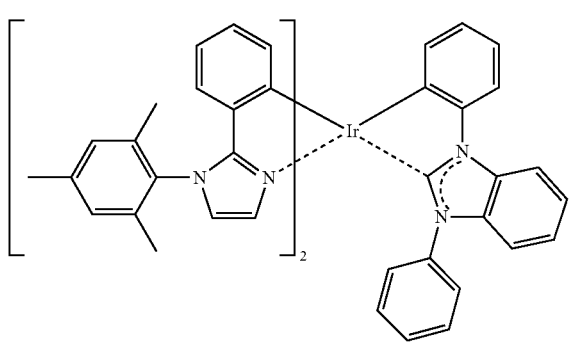
D-58
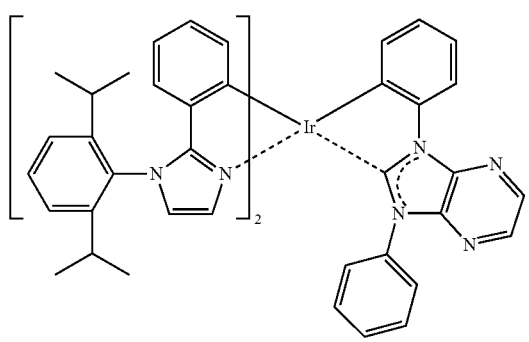
[Chemical Formula 72]
D-59
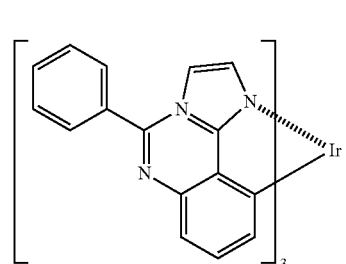
D-60
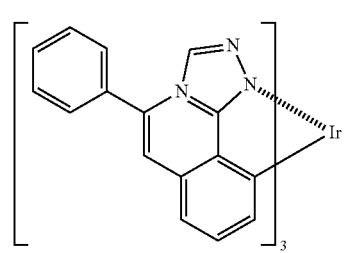
-continued
D-61
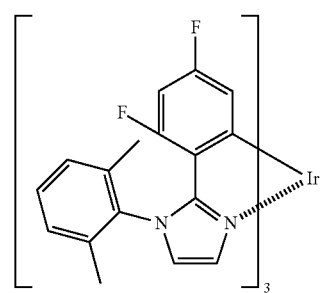
D-62
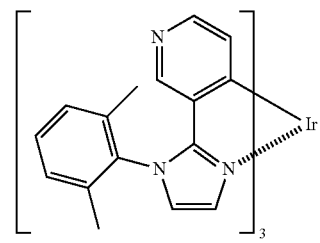
D-63
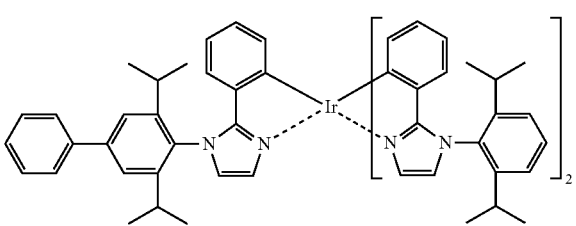
D-64
D-65

D-66
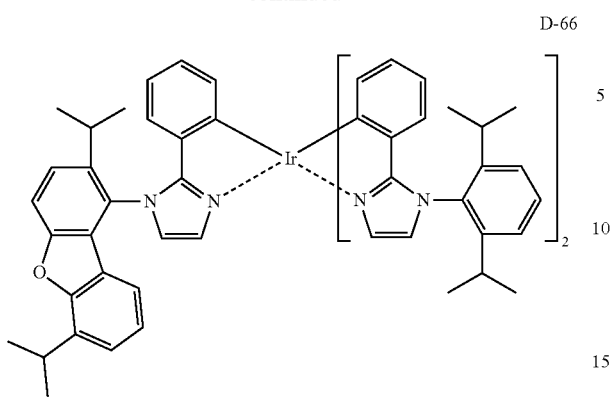
D-67
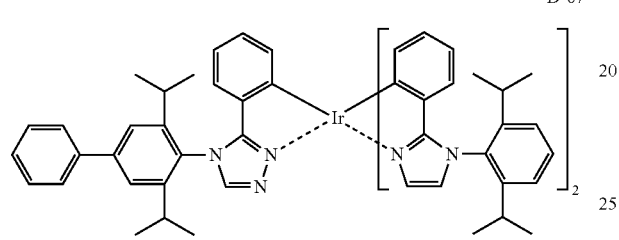
D-68
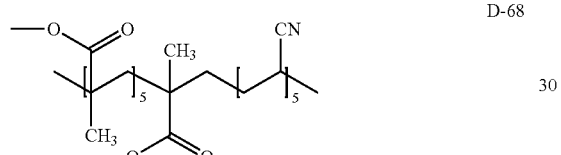
D-69
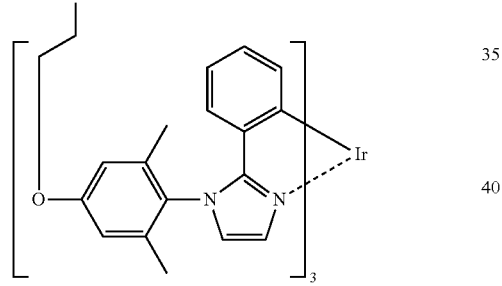
D-70
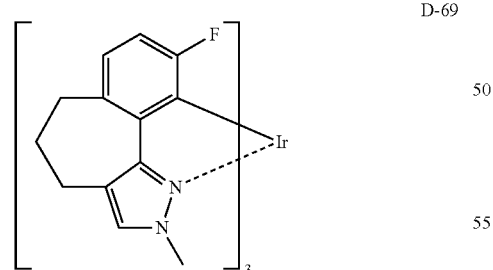
D-71
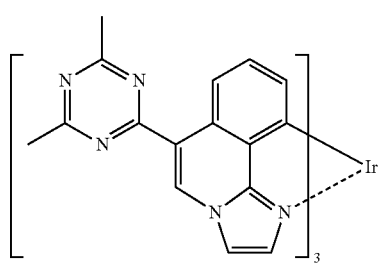
D-72
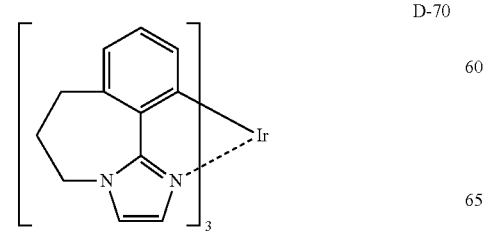
[Chemical Formula 73]
D-73
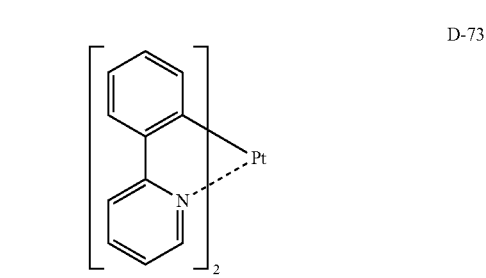
D-74
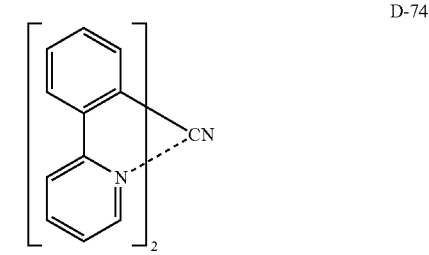
D-75
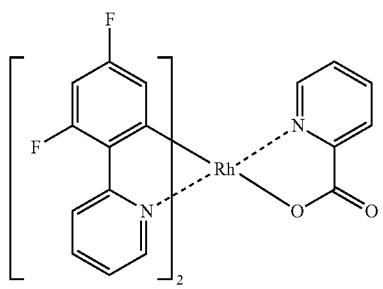
D-76
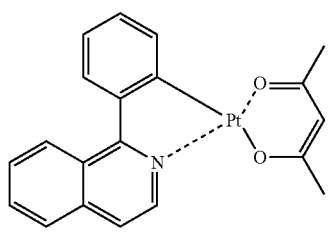

-continued

D-77 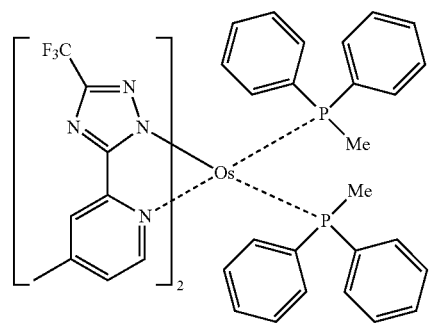

D-78 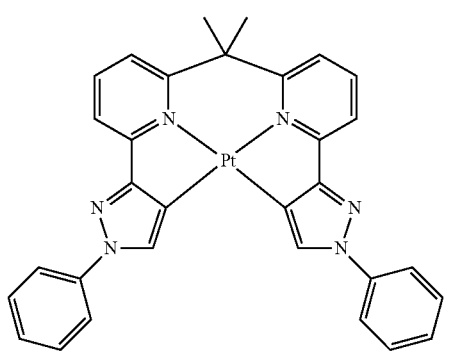

D-79 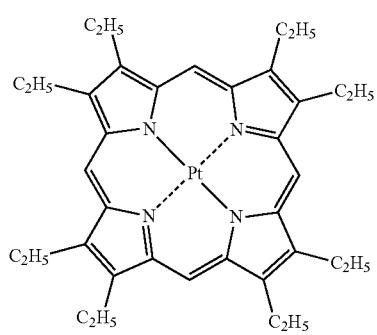

D-80 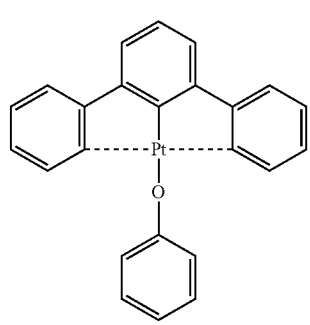

D-81 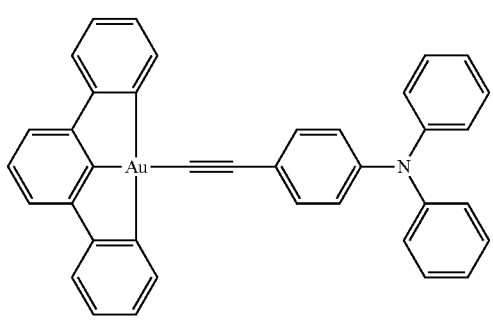

(1.2) Fluorescence-Emitting Dopant

The fluorescence-emitting dopant (hereinafter also referred to as the "fluorescent dopant") according to the present invention will be described.

The fluorescent dopant according to the present invention may be any compound capable of emitting light from the excited singlet state so that light emission from the excited singlet state can be observed.

Examples of the fluorescent dopant according to the present invention include anthracene derivatives, pyrene derivatives, chrysene derivatives, fluoranthene derivatives, perylene derivatives, fluorene derivatives, arylacetylene derivative, styrylarylene derivative, styrylamine derivatives, arylamine derivatives, boron complexes, coumarin derivatives, pyran derivatives, cyanine derivatives, croconium derivatives, squarylium derivatives, oxobenzanthracene derivatives, fluorescein derivatives, rhodamine derivatives, pyrylium derivatives, perylene derivatives, polythiophene derivatives, or rare earth complex compounds.

In recent years, light-emitting dopants capable of producing delayed fluorescence have been developed. Such dopants may also be used.

Examples of light-emitting dopants capable of producing delayed fluorescence include, but are not limited to, compounds described in WO 2011/156793 A, JP 2011-213643 A, and JP 2010-93181 A.

(2) Host Compound

The host compound according to the present invention is a compound that plays a role in injecting and transporting mainly charges in the light-emitting layer. In the organic EL device, light is not substantially observed from the host compound itself.

The host compound is preferably a compound whose phosphorescence quantum yield is less than 0.1, more preferably less than 0.01, with respect to phosphorescence emission at room temperature (25° C.). The host compound preferably makes up 20% or more of the weight of the compounds in the light-emitting layer.

In addition, the energy of the excited state of the host compound is preferably higher than the energy of the excited state of the light-emitting dopant present in the same layer.

A host compound may be used alone, or two or more host compounds may be used together. Using two or more host compounds, charge transfer can be controlled so that the organic EL device can have a high efficiency.

Any host compound conventionally used in organic EL devices may be used in the present invention. The host compound may be a low molecular weight compound, a polymer compound having a repeating unit(s), or a compound having a reactive group such as a vinyl group or an epoxy group.

Known host compounds are preferably such that they have the ability to transport holes or electrons, make it possible to prevent an increase in the emission wavelength, and also have a high glass transition temperature (Tg) so that stable operation of the organic EL device can be achieved during high-temperature driving or against the heat generated during the driving of the device. The Tg is preferably 90° C. or more, more preferably 120° C. or more.

The glass transition point (Tg) is the value determined by the method according to JIS-K-7121 using DSC (differential scanning calorimetry).

Examples of known host compounds that may be used for the organic EL device of the present invention include, but are not limited to, compounds described in the following literatures.

JP 2001-257076 A, JP 2002-308855 A, JP 2001-313179 A, JP 2002-319491 A, JP 2001-357977 A, JP 2002-334786 A, JP 2002-8860 A, JP 2002-334787 A, JP 2002-15871 A, JP 2002-334788 A, JP 2002-43056 A, JP 2002-334789 A, JP 2002-75645 A, JP 2002-338579 A, JP 2002-105445 A, JP 2002-343568 A, JP 2002-141173 A, JP 2002-352957 A, JP 2002-203683 A, JP 2002-363227 A, JP 2002-231453A, JP 2003-3165 A, JP 2002-234888 A, JP 2003-27048 A, JP 2002-255934 A, JP 2002-260861 A, JP 2002-280183 A, JP 2002-299060 A, JP 2002-302516 A, JP 2002-305083 A, JP 2002-305084 A, JP 2002-308837 A, US 2003/0,175,553 A, US 2006/0,280,965 A, US 2005/0,112,407 A, US 2009/0,017,330 A, US 2009/0,030,202 A, US 2005/0,238,919 A, WO 2001/039234 A, WO 2009/021126 A, WO 2008/056746 A, WO 2004/093207 A, WO 2005/089025 A, WO 2007/063796 A, WO 2007/063754 A, WO 2004/107822 A, WO 2005/030900 A, WO 2006/114966 A, WO 2009/086028 A, WO 2009/003898 A, WO 2012/023947 A, JP 2008-074939 A, JP 2007-254297 A, and EP 2034538.

[Electron Transport Layer]

In the present invention, the electron transport layer only needs to include a material having the function of transporting electrons and have the function of transmitting electrons to the light-emitting layer when the electrons are injected from the cathode.

In the present invention, the total thickness of the electron transport layer is generally, but not limited to, 2 nm to 5 μm, preferably 2 nm to 500 nm, more preferably 5 nm to 200 nm.

It is known that when light produced in the light-emitting layer of an organic EL device is extracted from the electrode, interference can occur between light directly extracted from the light-emitting layer and light extracted after it is reflected by the counter electrode opposite to the light extraction electrode. When light is reflected by the cathode, the total thickness of the electron transport layer may be appropriately adjusted between several nm and several μm so that the interference effect can be efficiently employed.

On the other hand, the voltage tends to increase as the thickness of the electron transport layer increases. Therefore, particularly when thick, the electron transport layer should preferably have an electron mobility of $10^{-5}$ cm$^2$/Vs or more.

The material used to form the electron transport layer (hereinafter referred to as the electron transport material) only needs to have either electron injection or transport properties or hole-barrier properties, and any suitable material may be selected from conventionally known compounds and used as the electron transport material.

Examples of the electron transport material include nitrogen-containing aromatic heterocyclic derivatives (such as carbazole derivatives, azacarbazole derivatives (which are derived by replacing at least one carbon atom in the carbazole ring with a nitrogen atom), pyridine derivatives, pyrimidine derivatives, pyrazine derivatives, pyridazine derivatives, triazine derivatives, quinoline derivatives, quinoxaline derivatives, phenanthroline derivatives, azatriphenylene derivatives, oxazole derivatives, thiazole derivatives, oxadiazole derivatives, thiadiazole derivatives, triazole derivatives, benzimidazole derivatives, benzoxazole derivatives, and benzothiazole derivatives), dibenzofuran derivatives, dibenzothiophene derivatives, silole derivatives, aromatic hydrocarbon ring derivatives (such as naphthalene derivatives, anthracene derivatives, and triphenylene), etc.

The electron transport material may also be a metal complex having a quinolinol or dibenzoquinolinol skeleton-containing ligand, such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, or bis(8-quinolinol) zinc (Znq), or a metal complex derived from any of these metal complexes by replacing the central metal with In, Mg, Cu, Ca, Sn, Ga, or Pb.

Alternatively, metal-free- or metallo-phthalocyanine or a compound derived therefrom by substitution with an alkyl group, a sulfonic acid group, or the like at the end is also preferably used as the electron transport material. Distyrylpyrazine derivatives, listed as materials for the light-emitting layer, may also be used as electron transport materials. Similarly to the hole injection layer or the hole transport layer, inorganic semiconductors such as n-type Si and n-type SiC may also be used as electron transport materials.

In addition, polymers having any of these materials incorporated in the polymer chain, or polymer materials having any of these materials in the polymer main chain may also be used.

The electron transport layer according to the present invention may also be a highly n-type (electron-rich) electron transport layer formed by doping an electron transport layer with a dopant as a guest material. The dopant may be an n-type dopant such as a metal complex, a metal halide, or a metal compound. Examples of the electron transport layer with such a composition include those described in literatures such as JP 04-297076 A, JP 10-270172 A, JP 2000-196140 A, JP 2001-102175 A, and J. Appl. Phys., 95, 5773 (2004).

Preferred examples of known electron transport materials that may be used in the organic EL device of the present invention include, but are not limited to, compounds described in the following literatures.

U.S. Pat. No. 6,528,187, U.S. Pat. No. 7,230,107, US 2005/0,025,993 A, US 2004/0,036,077 A, US 2009/0,115,316 A, US 2009/0,101,870 A, US 2009/0,179,554 A, WO 2003/060956 A, WO 2008/132085 A, Appl. Phys. Lett. 75, 4 (1999), Appl. Phys. Lett. 79, 449 (2001), Appl. Phys. Lett. 81, 162 (2002), Appl. Phys. Lett. 81, 162 (2002), Appl. Phys. Lett. 79, 156 (2001), U.S. Pat. No. 7,964,293, US 2009/030,202 A, WO 2004/080975 A, WO 2004/063159 A, WO 2005/085387 A, WO 2006/067931 A, WO 2007/086552 A, WO 2008/114690 A, WO 2009/069442 A, WO 2009/066779 A, WO 2009/054253 A, WO 2011/086935 A, WO 2010/150593 A, WO 2010/047707 A, EP 2311826, JP 2010-251675 A, JP 2009-209133 A, JP 2009-124114 A, JP 2008-277810A, JP 2006-156445 A, JP 2005-340122 A, JP 2003-45662 A, JP 2003-31367 A, JP 2003-282270 A, and WO 2012/115034 A.

In the present invention, the electron transport material is more preferably a pyridine derivative, a pyrimidine derivative, a pyrazine derivative, a triazine derivative, a dibenzofuran derivative, a dibenzothiophene derivative, a carbazole derivative, an azacarbazole derivative, or a benzimidazole derivative.

The electron transport materials may be used alone or in combination of two or more.

[Hole-Blocking Layer]

In abroad sense, the hole-blocking layer is a layer having the function of an electron transport layer. Preferably, the hole-blocking layer includes a material having the function of transporting electrons and a lower ability to transport holes so that it can increase the probability of recombination of electrons and holes by transporting electrons and blocking holes.

If necessary, the composition of the electron transport layer described above may be used to form the hole-blocking layer according to the present invention.

In the organic EL device of the present invention, the hole-blocking layer is preferably provided adjacent to the cathode side of the light-emitting layer.

In the present invention, the hole-blocking layer preferably has a thickness in the range of 3 to 100 nm, more preferably in the range of 5 to 30 nm.

The material used to form the electron transport layer described above is preferably used to form the hole-blocking layer. The material used as the host compound described above is also preferably used to form the hole-blocking layer.

[Electron Injection Layer]

In the present invention, the electron injection layer (also referred to as the "cathode buffer layer") is a layer provided between the cathode and the light-emitting layer so as to reduce the driving voltage or improve the emission luminance. Such a layer is described in detail in "Yuki EL Soshi to Sono Kogyoka-Saizensen" (Organic EL Devices and Forefront of Their Industrialization), published by NTS Inc., Nov. 30, 1998, Part 2, Chapter 2, "Denkyoku Zairyou" (Electrode Materials), pages 123-166.

In the present invention, the electron injection layer is optionally provided. As mentioned above, it may be disposed between the cathode and the light-emitting layer or between the cathode and the electron transport layer.

The electron injection layer is preferably a very thin film and preferably has a thickness in the range of 0.1 nm to 5 nm although it depends on the material. The electron injection layer may also be a nonuniform film in which the component material is intermittently deposited.

The electron injection layer is also described in detail in publications such as JP 06-325871 A, JP 09-17574 A, and JP 10-74586 A. Examples of materials preferably used to form the electron injection layer include metals such as strontium and aluminum, alkali metal compounds such as lithium fluoride, sodium fluoride, and potassium fluoride, alkaline earth metal compounds such as magnesium fluoride and calcium fluoride, metal oxides such as aluminum oxide, and metal complexes such as lithium 8-hydroxyquinolate (Liq). The electron transport material described above may also be used.

The materials for the electron injection layer may be used alone or in combination of two or more.

[Hole Transport Layer]

In the present invention, the hole transport layer only needs to include a material having the function of transporting holes so that it has the function of transmitting holes to the light-emitting layer when the holes are injected from the anode.

In the present invention, the total thickness of the hole transport layer is generally, but not limited to, 5 nm to 5 μm, preferably 2 nm to 500 nm, more preferably 5 nm to 200 nm.

The material used to form the hole transport layer (hereinafter referred to as the hole transport material) only needs to have either hole injection or transport properties or electron-barrier properties, and any suitable material may be selected from conventionally known compounds and used as the hole transport material.

Examples of the hole transport material include porphyrin derivatives, phthalocyanine derivatives, oxazole derivatives, oxadiazole derivatives, triazole derivatives, imidazole derivatives, pyrazoline derivatives, pyrazolone derivatives, phenylenediamine derivatives, hydrazone derivatives, stilbene derivatives, polyarylalkane derivatives, triarylamine derivatives, carbazole derivatives, indolocarbazole derivatives, isoindole derivatives, acene derivatives such as anthracene and naphthalene derivatives, fluorene derivatives, fluorenone derivatives, polyvinyl carbazole, polymers or oligomers having aromatic amine incorporated in the main or side chain, polysilane, and conductive polymers or oligomers (such as PEDOT:PSS, aniline copolymers, polyaniline, and polythiophene).

Triarylamine derivatives include benzidines such as αNPD, starburst derivatives such as MTDATA, and compounds having a fluorene or anthracene moiety combined with the triarylamine core.

Hexaazatriphenylene derivatives such as those described in JP 2003-519432 W and JP 2006-135145 A may also be used as hole transport materials.

In addition, an impurity-doped, highly p-type, hole transport layer may also be used. Examples of such a layer include those described in JP 04-297076 A, JP 2000-196140 A, JP 2001-102175 A, and J. Appl. Phys., 95, 5773 (2004).

In addition, inorganic materials described in JP 11-251067 A and J. Huang et. al., Applied Physics Letters 80 (2002), p. 139 may also be used, such as what are called p-type hole transport materials, p-type Si, and p-type SiC. An orthometallized organometallic complex having Ir or Pt as a central metal, such as Ir(ppy)3, is also preferably used.

Among the above hole transport materials that may be used, triarylamine derivatives, carbazole derivatives, indolocarbazole derivatives, azatriphenylene derivatives, organometallic complexes, and polymers or oligomers having aromatic amine incorporated in the main or side chain are preferably used.

Preferred examples of known hole transport materials that may be used for the organic EL device of the present invention include, but are not limited to, the compounds described in the literatures shown above and compounds described in the following literatures.

For example, Appl. Phys. Lett. 69, 2160 (1996), J. Lumin. 72-74, 985 (1997), Appl. Phys. Lett. 78, 673 (2001), Appl. Phys. Lett. 90, 183503 (2007), Appl. Phys. Lett. 90, 183503 (2007), Appl. Phys. Lett. 51, 913 (1987), Synth. Met. 87, 171 (1997), Synth. Met. 91, 209 (1997), Synth. Met. 111, 421 (2000), SID Symposium Digest, 37, 923 (2006), J. Mater. Chern. 3, 319 (1993), Adv. Mater. 6, 677 (1994), Chern. Mater. 15, 3148 (2003), US 2003/0,162,053 A, US 2002/0,158,242 A, US 2006/0,240,279 A, US 2008/0,220,265 A, U.S. Pat. No. 5,061,569, WO 2007/002683 A, WO 2009/018009 A, EP 650955, US 2008/0,124,572 A, US 2007/0,278,938 A, US 2008/0,106,190 A, US 2008/0,018,221 A, WO 2012/115034 A, JP 2003-519432 W, JP 2006-135145 A, and U.S. Ser. No. 13/585,981.

The hole transport materials may be used alone or in combination of two or more.

[Electron-Blocking Layer]

In a broad sense, the electron-blocking layer is a layer having the function of a hole transport layer. Preferably, the electron-blocking layer includes a material having the function of transporting holes and a lower ability to transport electrons so that it can increase the probability of recombination of electrons and holes by transporting holes and blocking electrons.

If necessary, the composition of the hole transport layer described above may be used to form the electron-blocking layer according to the present invention.

In the organic EL device of the present invention, the electron-blocking layer is preferably provided adjacent to the anode side of the light-emitting layer.

In the present invention, the electron-blocking layer preferably has a thickness in the range of 3 to 100 nm, more preferably in the range of 5 to 30 nm.

The material used to form the hole transport layer described above is preferably used to form the electron-blocking layer. The material used as the host compound described above is also preferably used to form the electron-blocking layer.

[Hole Injection Layer]

In the present invention, the hole injection layer (also referred to as the "anode buffer layer") is a layer provided between the anode and the light-emitting layer so as to reduce the driving voltage or improve the emission luminance. Such a layer is described in detail in "Yuki EL Soshi to Sono Kogyoka-Saizensen" (Organic EL Devices and Forefront of Their Industrialization), published by NTS Inc., Nov. 30, 1998, Part 2, Chapter 2, "Denkyoku Zairyou" (Electrode Materials), pages 123-166.

In the present invention, the hole injection layer is optionally provided and may be provided between the anode and the light-emitting layer or between the anode and the hole transport layer as mentioned above.

The hole injection layer is also described in detail in publications such as JP 09-45479 A, JP 09-260062 A, and JP 08-288069 A. Examples of the material used to form the hole injection layer include those for the hole transport layer shown above.

Particularly preferred are phthalocyanine derivatives such as copper phthalocyanine, hexaazatriphenylene derivatives such as those described in JP 2003-519432 W and JP 2006-135145 A, metal oxides such as vanadium oxide, amorphous carbon, conductive polymers such as polyaniline (Emeraldine) and polythiophene, orthometallized complexes such as tris(2-phenylpyridine)iridium complexes, and triarylamine derivatives.

The materials for the hole injection layer may be used alone or in combination of two or more.

[Additional Component]

Each layer of the light-emitting functional layer described above may also contain an additional component.

Examples of the additional component include halogen elements such as bromine, iodine, and chlorine, halides, alkali metals such as Pd, Ca, and Na, alkaline earth metals, and compounds, complexes, or salts of transition metals, etc.

The content of the additional component, which may be freely determined, is preferably 1,000 ppm or less, more preferably 500 ppm or less, even more preferably 50 ppm or less, based on the total weight (%) of the layer or layers containing the additional component.

It will be understood that such ranges will not apply for the purpose of improving the electron or hole transport properties or making advantageous the exciton energy transfer.

[Methods for Forming Light-Emitting Functional Layer]

Methods for forming each layer (hole injection layer, hole transport layer, light-emitting layer, hole-blocking layer, electron transport layer, electron injection layer, etc.) of the light-emitting functional layer will be described.

Each layer of the light-emitting functional layer may be formed using any of conventionally known methods such as vacuum vapor deposition and wet methods (also referred to as wet processes).

Wet methods include spin coating, casting, ink-jetting, printing, die coating, blade coating, roll coating, spray coating, curtain coating, LB techniques (Langmuir-Blodgett techniques), etc. In view of easy formation of uniform thin films and high productivity, methods highly suitable for roll-to-roll system are preferred, such as die coating, roll coating, ink-jetting, and spray coating.

The organic EL material according to the present invention may be dissolved or dispersed in a liquid medium. Examples of such a liquid medium that may be used include ketones such as methyl ethyl ketone and cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decalin, and dodecane, and other organic solvents such as DMF and DMSO.

The dispersion method may be ultrasonic dispersion, high shear dispersion, medium dispersion, or other methods capable of disperse the material.

The deposition method used may also differ from layer to layer. When vapor deposition is used to form the film, the deposition conditions, although varying with the type of the compound used and other factors, are preferably selected as appropriate from the following common ranges: boat heating temperature 50° C. to 450° C., the degree of vacuum $10^{-6}$ Pa to $10^{-2}$ Pa, deposition rate 0.01 nm/sec to 50 nm/sec, substrate temperature −50° C. to 300° C., film thickness 0.1 nm to 5 µm, preferably 5 nm to 200 nm.

In the present invention, the formation of the organic layers is preferably performed in such a way that the layers from the hole injection layer to the cathode are continuously formed in a single vacuum pumping process. Alternatively, however, the product may be taken out in midstream and then subjected to a different deposition process. In such a case, the operation should preferably be performed under a dry inert gas atmosphere.

[Auxiliary Electrode 15]

The auxiliary electrode 15, which is provided to reduce the resistance of the transparent electrode 1, is provided in contact with the electrode layer 1b of the transparent electrode 1. The auxiliary electrode 15 is preferably made of a low-resistance metal such as gold, platinum, silver, copper, or aluminum. Since these metals have low optical transparency, the auxiliary electrode 15 should be patterned so that the extraction of emitted light h from a light extraction surface 17a will not be affected. Such a method for forming the auxiliary electrode 15 may be vapor deposition, sputtering, printing, ink-jetting, or aerosol jetting. In view of the numerical aperture for light extraction, the auxiliary electrode 15 preferably has a line width of 50 µm or less. In view of conductivity, the auxiliary electrode 15 preferably has a thickness of 1 µm or more.

[Transparent Sealant 17]

The transparent sealant 17 is provided to cover the organic electroluminescent device EL-1. The transparent sealant 17 may be a sheet-shaped (film-shaped) sealant, which is bonded to the substrate 13 side with an adhesive 19, or a sealing film. The surface of the transparent sealant 17 forms a light extraction surface 17a from which the emitted light h of the organic electroluminescent device EL-1 is extracted. In such a case, the transparent sealant 17 is provided to cover at least the light-emitting functional layer 3 while the terminal parts of the transparent electrode 1 and the counter electrode 5-1 of the organic electroluminescent device EL-1 are exposed. The transparent sealant 17 may also be provided with electrodes, and the terminal parts of the transparent electrode 1 and the counter electrode 5-1 of the organic electroluminescent device EL-1 may be electrically connected to the electrodes, respectively.

The sheet-shaped (film-shaped) transparent sealant 17 may be, for example, a glass base material or a polymer base material. These base materials may be further formed into thin films. Specifically, the glass base material may be soda-lime glass, barium/strontium-containing glass, lead glass, aluminosilicate glass, borosilicate glass, barium borosilicate glass, quartz, or the like. The polymer base material may be polycarbonate, acrylic, polyethylene terephthalate, polyether sulfide, polysulfone, or the like.

In particular, a thin film of the polymer base material is preferably used as the transparent sealant 17, so that the device can be obtained in the form of a thin film.

In addition, such a film of the polymer base material preferably has an oxygen permeability of $1 \times 10^{-3}$ ml/(m²·24 h·atm) or less as measured by the method according to JIS K 7126 (1987) and a water-vapor permeability of $1 \times 10^{-3}$ g/(m²·24 h) or less (25±0.5° C., relative humidity (90±2)% RH) as measured by the method according to JIS K 7129 (1992).

The base material described above may also be formed into a concave sheet and then used as the transparent sealant 17. In this case, the base material member may be subjected to sand blasting, chemical etching, or other processes so that a concave shape is formed.

An adhesive 19 is used to bond such a sheet-shaped transparent sealant 17 to the substrate 13 side. The adhesive 19 is used as a sealing agent for sealing the organic electroluminescent device EL-1 sandwiched between the transparent sealant 17 and the substrate 13. Specifically, the adhesive 19 may be a photo-curing or thermosetting adhesive having a reactive vinyl group, such as an acrylic acid oligomer or a methacrylic acid oligomer, or a moisture-curing adhesive such as 2-cyanoacrylic acid ester.

Alternatively, the adhesive 19 may be of a thermosetting and chemical setting type (two-part mixing type) such as an epoxy adhesive. A hot melt adhesive such as polyamide, polyester, or polyolefin may also be used. A cationic curing or ultraviolet curing epoxy resin adhesive may also be used.

Some organic materials used to form the organic electroluminescent device EL-1 may be degraded by heat treatment. Therefore, the adhesive 19 is preferably such that it can be bonded and cured at a temperature from room temperature to 80° C. A desiccant may also be dispersed in the adhesive 19.

A commercially available disperser may be used to apply the adhesive 19 to the part where the transparent sealant 17 and the substrate 13 are to be bonded, or the adhesive 19 may be applied by printing such as screen printing. The adhesive 19 may be provided only at the circumference of the transparent sealant 17 as shown in the drawing. Alternatively, the adhesive 19, if made of a material capable of having sufficient optical transparency after curing, may be filled, with no gap left, between the transparent sealant 17 and the organic electroluminescent device EL-1.

When a gap is formed between the sheet-shaped transparent sealant 17, the substrate 13, and the adhesive 19, inert gas such as nitrogen or argon or inert liquid such as fluorinated hydrocarbon or silicone oil is preferably injected into the gap in a gas or liquid phase. Alternatively, vacuum may also be used. In addition, a moisture absorbing compound may also be sealed inside.

Examples of the moisture absorbing compound include metal oxides (such as sodium oxide, potassium oxide, calcium oxide, barium oxide, magnesium oxide, and aluminum oxide), sulfates (such as sodium sulfate, potassium sulfate, magnesium sulfate, and cobalt sulfate), metal halides (such as calcium chloride, magnesium chloride, cesium fluoride, tantalum fluoride, cerium bromide, magnesium bromide, barium iodide, and magnesium iodide), and perchlorates (such as barium perchlorate and magnesium perchlorate). Anhydrous salts are preferably used for sulfates, metal halides, and perchlorates.

On the other hand, a sealing film may be used as the transparent sealant 17. In this case, the sealing film is provided on the substrate 13 in such a way that the light-emitting functional layer 3 of the organic electroluminescent device EL-1 is completely covered while the terminal parts of the transparent electrode 1 and the counter electrode 5-1 of the organic electroluminescent device EL-1 are exposed.

Such a sealing film is made of an inorganic or organic material. Such a sealing film should be made of a material having the function of preventing the entry of water, oxygen, and other substances capable of degrading the light-emitting functional layer 3 of the organic electroluminescent device EL-1. Such a material may be, for example, an inorganic material such as silicon oxide, silicon dioxide, or silicon nitride. To improve the brittleness of the sealing film, an organic material film may also be used together with the inorganic material film to form a multilayer structure.

These films may be formed by any method such as vacuum vapor deposition, sputtering, reactive sputtering, molecular beam epitaxy, ionized cluster beam technique, ion plating, plasma polymerization, atmospheric pressure plasma polymerization, plasma CVD, laser CVD, thermal CVD, or coating.

[Protective Film or Protective Sheet]

Although not shown, a protective film or a protective sheet may be provided in such a way that the organic electroluminescent device EL and the transparent sealant 17 are sandwiched between the substrate 13 and the protective film or sheet. The protective film or sheet is provided to mechanically protect the organic electroluminescent device EL. Particularly when the transparent sealant 17 is a sealing film, the protective film or sheet is preferably provided because the mechanical protection of the organic electroluminescent device EL by the sealing film is not sufficient.

The protective film or sheet may be a glass sheet, a polymer sheet, a polymer film thinner than the above, a metal sheet, a thin metal film thinner than the metal sheet, a polymer material film, or a metal material film. In particular, a polymer film is preferably used in view of lightweight and thickness reduction.

The organic electroluminescent device EL-1 of the present invention preferably has an emitted light h extraction efficiency of 1% or more, more preferably 5% or more at room temperature. In this regard, the light extraction efficiency (%)=(the number of photons extracted from the organic electroluminescent device)/(the number of electrons allowed to flow through the organic EL device)×100. A hue improvement filter such as a color filter or a color conversion filter with a fluorescent material for converting the color of the light emitted from the organic EL device to a plurality of colors may also be used and disposed on the light extraction side.

[Method for Manufacturing Organic Electroluminescent Device]

Hereinafter, a method for manufacturing the organic electroluminescent device EL-1 shown in FIG. 7 will be described as an example.

First, the counter electrode 5-1 for serving as an anode is formed on the substrate 13 by a suitable method as described above, and then the light-emitting functional layer 3 is formed thereon by a suitable method as described above.

The nitrogen-containing layer 1a is then formed with a thickness of 1 μm or less, preferably 10 nm to 100 nm. Subsequently, the electrode layer 1b of silver (or an alloy composed mainly of silver) is formed with a thickness of 4 nm to 12 nm, so that the transparent electrode 1 on the cathode side is formed. The nitrogen-containing layer 1*a* and the electrode layer 1*b* can be formed by spin coating, casting, ink-jetting, vapor deposition, sputtering, printing, or the like. Vapor deposition is particularly preferred because it can easily form a uniform film and is less likely to form pinholes.

Specifically, the electrode layer 1*b* is formed and patterned to have a terminal part extending from the top of the light-emitting functional layer 3 to the edge of the substrate 13, while it is insulated from the counter electrode 5-1 with the light-emitting functional layer 3. If necessary, the auxiliary electrode 15 may be patterned before or after the formation of the electrode layer 1*b*. In this way, the organic electroluminescent device EL-1 is obtained. Subsequently, the transparent sealant 17 is provided to cover at least the light-emitting functional layer 3 while the terminal parts of the transparent electrode 1 and the counter electrode 5-1 of the organic electroluminescent device EL-1 are exposed. In this process, the adhesive 19 is used to bond the transparent sealant 17 to the substrate 13 side so that the organic electroluminescent device EL-1 is sealed between the transparent sealant 17 and the substrate 13.

Thus, the desired organic electroluminescent device EL-1 is obtained on the substrate 13. When the organic electroluminescent device EL-1 is manufactured in this way, it is preferable to continuously form the components from the light-emitting functional layer 3 to the counter electrode 5-1 in a single vacuum pumping process. Alternatively, however, the substrate 13 may be taken out of the vacuum atmosphere in midstream and then subjected to a different deposition process. In such a case, it is necessary to adopt special measures such as operation under a dry inert gas atmosphere.

A DC voltage of about 2 V to about 40 V may be applied to the organic electroluminescent device EL-1 obtained as described above, in which the counter electrode 5-1 is a plus pole (anode) and the electrode layer 1*b* is a minus pole (cathode), so that light emission can be observed. Alternatively, an AC voltage may be applied. The AC voltage applied may have any waveform.

<Advantageous Effects of Organic Electroluminescent Device EL-1>

The organic electroluminescent device EL-1 described above includes the transparent electrode 1 of the present invention as a cathode, which has both conductivity and optical transparency and also has improved reliability. The device EL-1 also includes the light-emitting functional layer 3 provided on the nitrogen-containing layer 1*a* side of the transparent electrode 1, and the counter electrode 5-1 as an anode, which are provided in this order. In this structure, a sufficient voltage can be applied across the transparent electrode 1 and the counter electrode 5-1, so that the organic electroluminescent device EL-1 can emit light with high luminance and the efficiency of extraction of emitted light h from the transparent electrode 1 side can be improved, so that high luminance can be achieved. In addition, such performance can be maintained for a long time, so that improved long-term reliability can be achieved. In addition, the driving voltage for a certain level of luminance can also be reduced, so that the emission lifetime can be extended.

<<4. Second Example of Organic Electroluminescent Device (Bottom Emission Type)>>

<Structure of Organic Electroluminescent Device>

Figure 8:
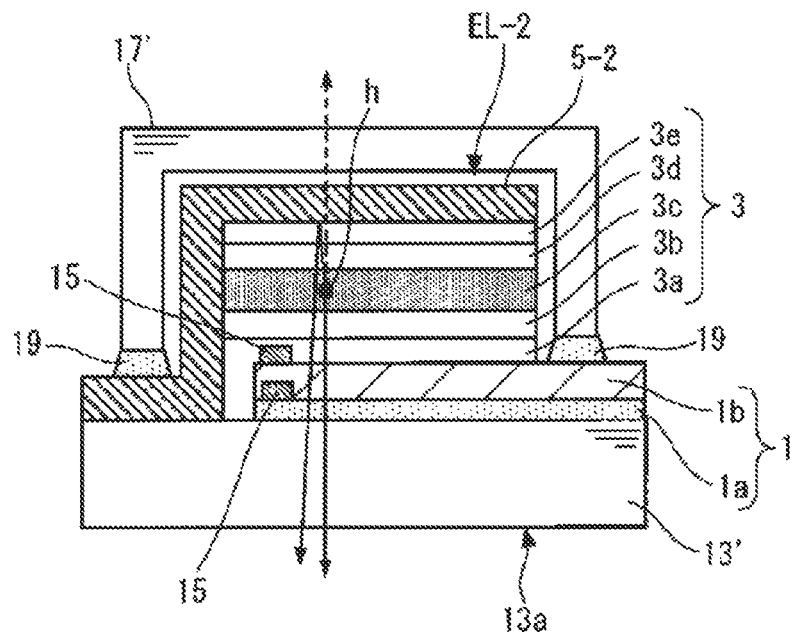
FIG. 8 is a cross-sectional view illustrating the structure of a second example of an organic electroluminescent device including a transparent electrode according to the present invention.

FIG. 8 is a cross-sectional view illustrating the structure of a second example of an organic electroluminescent device having the transparent electrode of the present invention. An organic electroluminescent device EL-2 as the second example shown in the drawing differs from the organic electroluminescent device EL-1 as the first example described with reference to FIG. 7 in that the transparent electrode 1 is provided on a transparent substrate 13' and the light-emitting functional layer 3 and a counter electrode 5-2 are provided thereon in this order. Hereinafter, characteristic elements of the organic electroluminescent device EL-2 as the second example will be described while the same elements as those in the first example will not be described in detail.

The organic electroluminescent device EL-2 shown in FIG. 8 is provided on the transparent substrate 13'. The transparent electrode 1 for serving as an anode, the light-emitting functional layer 3, and the counter electrode 5-2 for serving as a cathode are stacked in this order from the transparent substrate 13' side. This structure is characterized by having the transparent electrode 1 of the present invention described above. Therefore, the organic electroluminescent device EL-2 is a bottom emission structure, in which emitted light h is extracted from at least the transparent substrate 13' side.

In such a case, the overall layer structure of the organic electroluminescent device EL-2 is not restricted and may be any common layer structure as in the first example. In the case of the second example, an illustrative structure includes a hole injection layer 3*a*, a hole transport layer 3*b*, a light-emitting layer 3*c*, an electron transport layer 3*d*, and an electron injection layer 3*e*, which are stacked in this order on the top of the transparent electrode 1 for serving as an anode, and further includes the counter electrode 5-2 for serving as a cathode provided thereon. This structure should have, as an essential component, the light-emitting layer 3*c* including at least an organic material. The electron transport layer 3*d* may also have electron injection properties so as to also serve as the electron injection layer 3*e*.

As described for the first example, the light-emitting functional layer 3 may have any of various structures as needed, and therefore, may include a hole-blocking layer or an electron-blocking layer, which is not shown in the drawing. In this structure, only the part where the light-emitting functional layer 3 is sandwiched between the transparent electrode 1 and the counter electrode 5-2 serves as a light-emitting region in the organic electroluminescent device EL-2 similarly to the first example.

In the organic electroluminescent device EL-2 as the second example, the light-emitting functional layer 3 is provided directly on the electrode layer 1*b*, which substantially functions as an anode in the transparent electrode 1. Therefore, it is preferable that the nitrogen-containing layer 1*a* should include a compound with an effective lone pair content [n/M] in the specified range and the effective lone pair content [n/M] of the nitrogen-containing layer 1*a* itself should be in the specified range. Therefore, the nitrogen-containing layer 1*a* does not need to include a material having hole transport properties or hole injection properties. The nitrogen-containing layer 1*a* may also be a multilayer structure. In this case, an about 5-nm-thick interfacial layer of the nitrogen-containing layer 1*a* on the electrode layer 1*b* side is preferably formed to have an effective lone pair content [n/M] in the specified range.

In order to reduce the resistance of the transparent electrode 1, the layer structure shown above may also include an auxiliary electrode 15 in contact with the electrode layer 1*b* of the transparent electrode 1 as in the first example.

In addition, the counter electrode 5-2 provided on the upper side of the light-emitting functional layer 3 is an electrode film for serving as a cathode, and its interfacial layer on the side in contact with the light-emitting functional layer 3 includes a material suitable as a cathode. The material suitable as a cathode may be an electrode material with a low work function (4 eV or less) such as a metal (referred to as an electron injecting metal), an alloy, an electrically-conductive compound, or any mixture thereof. Examples of such an electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, aluminum, and rare earth metals. Among them, in view of electron injection properties and durability against oxidation or the like, preferred examples are a mixture of an electron injecting metal and a second metal that has a work function higher than that of the electron injecting metal and is more stable, such as a magnesium-silver mixture, a magnesium-aluminum mixture, a magnesium-indium mixture, an aluminum-aluminum oxide ($Al_2O_3$) mixture, or a lithium-aluminum mixture, and aluminum.

The cathode can be produced by forming a thin film of any of these electrode materials by a method such as vapor deposition or sputtering. The sheet resistance of the cathode is preferably not more than several hundred Ω/square, and the cathode generally has a thickness selected in the range of 10 nm to 5 μm, preferably in the range of 50 nm to 200 nm.

In this case, a sealant 17' used to seal the bottom emission organic electroluminescent device EL-2 does not need to have optical transparency. The sealant 17' may be made of the same material as the transparent sealant used in the first example or a metal material. The metal material may be at least one metal selected from the group consisting of stainless steel, iron, copper, aluminum, magnesium, nickel, zinc, chromium, titanium, molybdenum, silicon, germanium, and tantalum, or an alloy thereof. Any of these metal materials can be formed into a thin film when used as the sealant 17', so that the total thickness of a light-emitting panel having the organic electroluminescent device can be reduced.

When emitted light h is also extracted from the counter electrode 5-2 side in the organic electroluminescent device EL-2, the counter electrode 5-2 should include a highly light-transmitting conductive material, which is selected from the conductive materials listed above. In this case, a transparent sealant having optical transparency is used as the sealant 17'.

<Advantageous Effects of Organic Electroluminescent Device EL-2>

The organic electroluminescent device EL-2 described above includes the transparent electrode 1 of the present invention as an anode, which has both conductivity and optical transparency and also has improved reliability. The device EL-2 also includes the light-emitting functional layer 3 and the counter electrode 5-2 for serving as a cathode, which are provided on the upper side of the transparent electrode 1. Therefore, similarly to the first example, a sufficient voltage can be applied across the transparent electrode 1 and the counter electrode 5-2, so that the organic electroluminescent device EL-2 can emit light with high luminance and the efficiency of extraction of emitted light h from the transparent electrode 1 side can be improved, so that high luminance can be achieved. In addition, such performance can be maintained for a long time, so that improved long-term reliability can be achieved. In addition, the driving voltage for a certain level of luminance can also be reduced, so that the emission lifetime can be extended.

<<5. Third Example of Organic Electroluminescent Device (Double-Sided Emission Type)>>

<Structure of Organic Electroluminescent Device>

Figure 9:
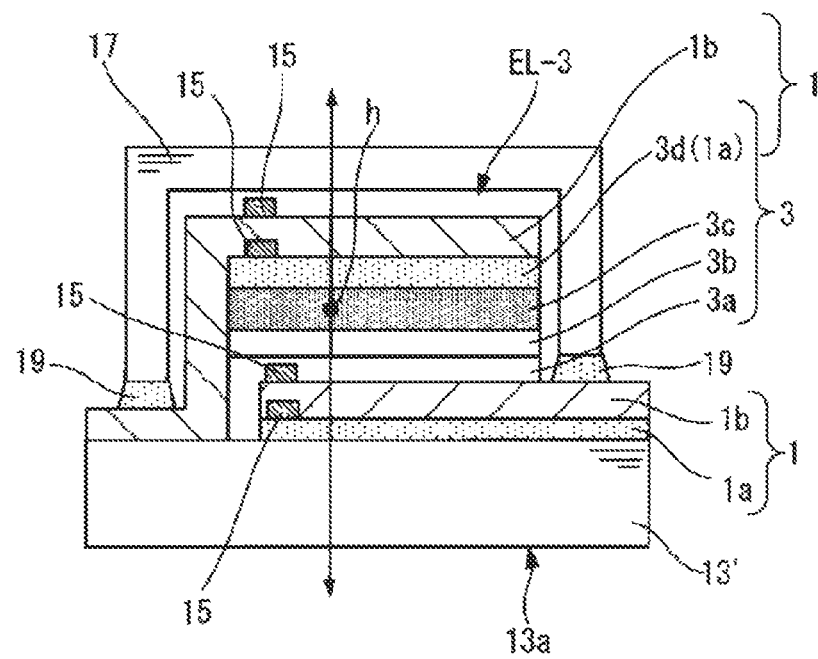
FIG. 9 is a cross-sectional view illustrating the structure of a third example of an organic electroluminescent device including a transparent electrode according to the present invention.

FIG. 9 is a cross-sectional view illustrating the structure of a third example of an organic electroluminescent device including the transparent electrode of the present invention. An organic electroluminescent device EL-3 as the third example shown in the drawing differs from the organic electroluminescent device EL-1 as the first example described with reference to FIG. 7 in that a transparent substrate 13' is used and the light-emitting functional layer 3 is disposed between two transparent electrodes 1. Hereinafter, characteristic elements of the organic electroluminescent device EL-3 as the third example will be described while the same elements as those in the first example will not be described in detail.

The organic electroluminescent device EL-3 shown in FIG. 9 is provided on the transparent substrate 13'. The transparent electrode 1 for serving as an anode, the light-emitting functional layer 3, and the transparent electrode 1 for serving as a cathode are stacked in this order from the transparent substrate 13' side. This structure is characterized by having the transparent electrode 1 of the present invention described above. Therefore, the organic electroluminescent device EL-3 is a double-sided emission structure, in which emitted light h is extracted from both the transparent substrate 13' side and the transparent sealant 17 side opposite thereto.

In such a case, the overall layer structure of the organic electroluminescent device EL-3 is not restricted and may be any common layer structure as in the first example. In the case of the third example, an illustrative structure includes a hole injection layer 3a, a hole transport layer 3b, a light-emitting layer 3c, and an electron transport layer 3d, which are provided in this order on the top of the transparent electrode 1 for serving as an anode, and further includes the transparent electrode 1 for serving as a cathode provided thereon. In the illustrated example, the electron transport layer 3d is provided to also serve as an electron injection layer and as the nitrogen-containing layer 1a of the transparent electrode 1 for serving as a cathode.

As described for the first example, the light-emitting functional layer 3 may have any of various structures as needed, and therefore, may include a hole-blocking layer or an electron-blocking layer, which is not shown in the drawing. In the structure shown above, only the part between the two transparent electrodes 1 serves as a light-emitting region in the organic electroluminescent device EL-3 similarly to the first example.

Also in the organic electroluminescent device EL-3 as the third example, the transparent electrode 1 provided on the transparent substrate 13' side includes the nitrogen-containing layer 1a and the electrode layer 1b provided in order from the transparent substrate 13' side, and the light-emitting functional layer 3 is provided directly on the electrode layer 1b, which substantially functions as an anode. Therefore, it is preferable that the nitrogen-containing layer 1a on the transparent substrate 13' side should include a compound with an effective lone pair content [n/M] in the specified range and the effective lone pair content [n/M] of the nitrogen-containing layer 1a itself should be in the specified range. Therefore, the nitrogen-containing layer 1a does not need to include a material having hole transport properties or hole injection properties. The nitrogen-containing layer 1a may also be a multilayer structure. In this case, an about 5-nm-thick interfacial layer of the nitrogen-containing layer 1a on the electrode layer 1b side is preferably formed to have an effective lone pair content [n/M] in the specified range.

On the other hand, the transparent electrode 1 provided on the light-emitting functional layer 3 includes the nitrogen-containing layer 1a and the electrode layer 1b, provided in order from the light-emitting functional layer 3 side, and the nitrogen-containing layer 1a is disposed between the light-emitting functional layer 3 and the electrode layer 1b for substantially serving as a cathode. Therefore, the nitrogen-containing layer 1a on the light-emitting functional layer 3 forms part of the light-emitting functional layer 3. In this case, the nitrogen-containing layer 1a includes a compound further having electron transport or injection properties, which is selected from the compounds having an effective lone pair content [n/M] in the specified range. Alternatively, in this case, the nitrogen-containing layer 1a may include a mixture of a compound having electron transport or injection properties and a compound having a certain level of effective lone pair content [n/M] so that the nitrogen-containing layer 1a itself has an effective lone pair content [n/M] in the specified range. The drawing shows a structure in which the nitrogen-containing layer 1a is provided only on the light-emitting layer 3c of the light-emitting functional layer 3. Alternatively, as long as the light-emitting function is not affected, the nitrogen-containing layer 1a may be provided over the surface adjacent to the electrode layer 1b so that the whole of the electrode layer 1b can contribute to the electrical conductivity. The nitrogen-containing layer 1a may also be a multilayer structure. In this case, an about 5-nm-thick interfacial layer of the nitrogen-containing layer 1a on the electrode layer 1b side is preferably formed to have an effective lone pair content [n/M] in the specified range. On the other hand, the remaining layer of the nitrogen-containing layer 1a on the light-emitting functional layer 3 side is preferably formed as an electron transport layer or an electron injection layer including a nitrogen-containing compound.

In the layer structure described above, auxiliary electrodes 15 for reducing the resistance of the transparent electrodes 1 may also be provided in contact with the electrode layers 1b of the two transparent electrodes 1 as in the first example.

The organic electroluminescent device EL-3, which is of a double-sided emission type, is sealed with a transparent sealant 17 having optical transparency.

<Advantageous Effects of Organic Electroluminescent Device EL-3>

The organic electroluminescent device EL-3 described above includes the transparent electrodes 1 of the present invention as an anode and a cathode, which have both conductivity and optical transparency and also have improved reliability. The device EL-3 also includes the light-emitting functional layer 3 disposed between these electrodes. Therefore, similarly to the first example, a sufficient voltage can be applied across the two transparent electrodes 1, so that the organic electroluminescent device EL-3 can emit light with high luminance and the efficiency of extraction of emitted light h from the two transparent electrode 1 sides can be improved, so that high luminance can be achieved. In addition, such performance can be maintained for a long time, so that improved long-term reliability can be achieved. In addition, the driving voltage for a certain level of luminance can also be reduced, so that the emission lifetime can be extended.

<<6. Fourth Example of Organic Electroluminescent Device (Inverted Structure)>>

<Structure of Organic Electroluminescent Device>

Figure 10:
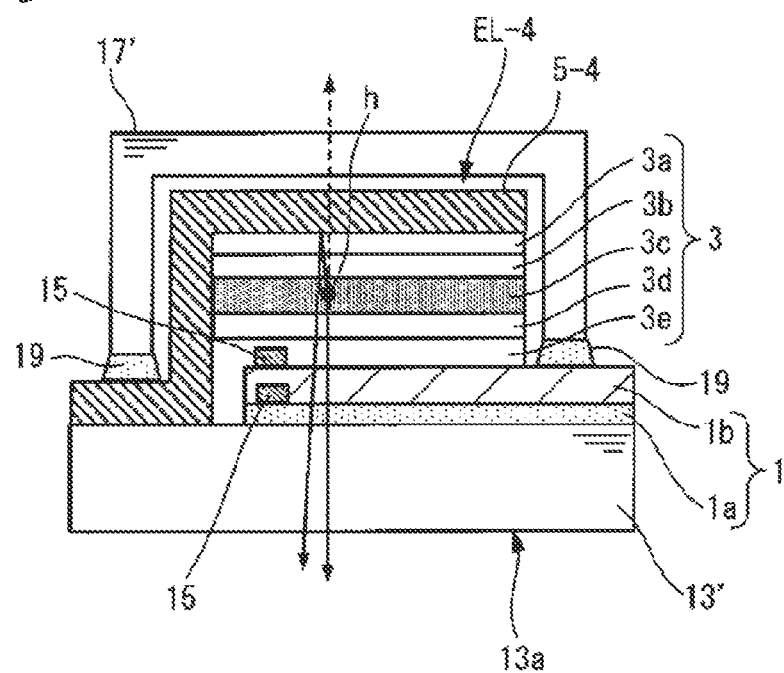
FIG. 10 is a cross-sectional view illustrating the structure of a fourth example of an organic electroluminescent device including a transparent electrode according to the present invention.

FIG. 10 is a cross-sectional view illustrating the structure of a fourth example of an organic electroluminescent device including the transparent electrode of the present invention. An organic electroluminescent device EL-4 as the fourth example shown in the drawing differs from the organic electroluminescent device EL-1 as the first example described with reference to FIG. 7 in that the layers are stacked in an inverted manner, specifically, the cathode (transparent electrode 1), the light-emitting functional layer 3, and the anode (counter electrode 5-4) are provided in this order from the transparent substrate 13' side. Hereinafter, characteristic elements of the organic electroluminescent device EL-4 as the fourth example will be described while the same elements as those in the first example will not be described in detail.

The organic electroluminescent device EL-4 shown in FIG. 10 is provided on the transparent substrate 13'. The transparent electrode 1 for serving as a cathode, the light-emitting functional layer 3, and the counter electrode 5-4 for serving as an anode are stacked in this order from the transparent substrate 13' side. This structure is characterized by having the transparent electrode 1 of the present invention described above. Therefore, the organic electroluminescent device EL-4 is a bottom emission structure, in which emitted light h is extracted from at least the transparent substrate 13' side.

In such a case, the overall layer structure of the organic electroluminescent device EL-4 is not restricted and may be any common layer structure as in the first example. In the case of the fourth example, an illustrative structure includes an electron injection layer 3e, an electron transport layer 3d, a light-emitting layer 3c, a hole transport layer 3b, and a hole injection layer 3a, which are provided in this order on the upper side of the transparent electrode 1 for serving as a cathode, and includes the counter electrode 5-4 for serving as an anode provided thereon.

As described for the first example, the light-emitting functional layer 3 may have any of various structures as needed, and therefore, may include a hole-blocking layer or an electron-blocking layer, which is not shown in the drawing. In the structure shown above, only the part between the transparent electrode 1 and the counter electrode 5-4 serves as a light-emitting region in the organic electroluminescent device EL-4 similarly to the first example.

In the organic electroluminescent device EL-4 as the fourth example, the light-emitting functional layer 3 is provided directly on the electrode layer 1b, which substantially functions as an anode, in the transparent electrode 1 provided on the transparent substrate 13' side. Therefore, it is preferable that the nitrogen-containing layer 1a should include a compound with an effective lone pair content [n/M] in the specified range and the effective lone pair content [n/M] of the nitrogen-containing layer 1a itself should be in the specified range. Therefore, the nitrogen-containing layer 1a does not need to include a material having electron transport properties or electron injection properties. The nitrogen-containing layer 1a may also be a multilayer structure. In this case, an about 5-nm-thick interfacial layer of the nitrogen-containing layer 1a on the electrode layer 1b side is preferably formed to have an effective lone pair content [n/M] in the specified range.

In the layer structure described above, an auxiliary electrode 15 for reducing the resistance of the transparent electrode 1 may also be provided in contact with the electrode layer 1b of the transparent electrode 1 as in the first example.

The counter electrode 5-4 provided as an anode on the upper side of the light-emitting functional layer 3 may be made of the same material as the anode in the first example.

As a modification of the fourth example, the transparent electrode 1 may also be used as the anode on the light-emitting functional layer 3. In this case, the electrode layer 1b, provided on the light-emitting functional layer 3 with the nitrogen-containing layer 1a interposed therebetween, serves as a substantial anode. The nitrogen-containing layer 1a provided on the light-emitting functional layer 3 also forms part of the light-emitting functional layer 3. In this case, the nitrogen-containing layer 1a includes a compound further having hole transport or injection properties, which is selected from the compounds having an effective lone pair content [n/M] in the specified range. Alternatively, in this case, the nitrogen-containing layer 1a may include a mixture of a compound having hole transport or injection properties and a compound having a certain level of effective lone pair content [n/M] so that the nitrogen-containing layer 1a itself has an effective lone pair content [n/M] in the specified range. The nitrogen-containing layer 1a may also be a multilayer structure. In this case, an about 5-nm-thick interfacial layer of the nitrogen-containing layer 1a on the electrode layer 1b side is preferably formed to have an effective lone pair content [n/M] in the specified range. On the other hand, the remaining layer of the nitrogen-containing layer 1a on the light-emitting functional layer 3 side is preferably formed as a hole transport layer or a hole injection layer including a nitrogen-containing compound.

<Advantageous Effects of Organic Electroluminescent Device EL-4>

The organic electroluminescent device EL-4 described above includes the transparent electrodes 1 of the present invention as a cathode, which has both conductivity and optical transparency and also has improved reliability. The device EL-4 also includes the light-emitting functional layer 3 and the counter electrode 5-4 as an anode, provided in this order on the cathode. Therefore, similarly to the first example, a sufficient voltage can be applied across the transparent electrode 1 and the counter electrode 5-4, so that the organic electroluminescent device EL-4 can emit light with high luminance and the efficiency of extraction of emitted light h from the transparent electrode 1 side can be improved, so that high luminance can be achieved. In addition, such performance can be maintained for a long time, so that improved long-term reliability can be achieved. In addition, the driving voltage for a certain level of luminance can also be reduced, so that the emission lifetime can be extended.

<<7. Applications of Organic Electroluminescent Device>>

The organic electroluminescent devices having the structures described above respectively are surface emitting devices and therefore can be used as a variety of light-emitting sources. Examples include illumination devices such as domestic lightings and vehicle interior lightings, backlights for watches and liquid crystal devices, lightings for sign advertisements, light sources for signals, light sources for optical recording media, light sources for electro-photographic copiers, light sources for optical communication processors, light sources for optical sensors, etc. However, these are non-limiting, and the devices can be effectively used in other applications, specifically, as backlights or illumination sources for use in combination with color filters for liquid crystal displays.

The organic electroluminescent device of the present invention may also be used as a certain type of lamp for illumination or an exposure light source. The organic electroluminescent device of the present invention may also be used for projection devices of an image projection type or displays on which viewers directly see still or moving images. In this case, a larger light-emitting surface may be formed by a technique what is called tiling, in which light-emitting panels each having the organic electroluminescent device are two-dimensionally joined together for a recent larger illumination device or display.

When the device is used in a display for reproducing moving images, the driving method may be of simple matrix (passive matrix) type or active matrix type. A color or full-color display can also be produced using two or more types of organic electroluminescent devices according to the present invention that emit light in different colors.

In the following, an illumination device will be described as an example of use, and then another illumination device having a light-emitting surface increased by tiling will be described.

<<8. Illumination Device I>>

An illumination device according to the present invention has the organic electroluminescent device described above.

The organic electroluminescent device for use in the illumination device according to the present invention may be designed to have a resonator structure incorporated in each structure described above. Examples of the purpose of the organic electroluminescent device having the resonator structure include, but are not limited to, light sources for optical recording media, light sources for electro-photographic copiers, light sources for optical communication processors, and light sources for optical sensors. The device may also be designed to perform laser oscillation for use in the above applications.

The materials used to form the organic electroluminescent device of the present invention can be used to form an organic electroluminescent device capable of emitting substantially white light (also referred to as a white organic electroluminescent device). For example, light in multiple colors may be emitted simultaneously using multiple luminescent materials and mixed to produce white light emission. The combination of multiple colors may include three maximum emission wavelengths for three primary colors, red, green, and blue, or include two maximum emission wavelengths in complementary color relationship, such as blue and yellow or blue green and orange.

The combination of luminescent materials to produce multiple luminescent colors may be either a combination of two or more materials capable of emitting different types of phosphorescence or fluorescence or a combination of a luminescent material capable of emitting fluorescence or phosphorescence and a dye material capable of emitting light using, as exciting light, the light from the luminescent material. A white organic electroluminescent device may also use a mixture of two or more light-emitting dopants.

Such a white organic electroluminescent device emits white light by itself in contrast to a structure including organic electroluminescent devices for different emission colors separately arranged parallel in an array to produce white light emission. When such a device is produced, therefore, no mask is required in forming almost all the layers of the device, and for example, an electrode film can be formed over a surface by vapor deposition, casting, spin-coating, ink-jetting, or printing, which improves the productivity.

The light-emitting layer of such a white organic electroluminescent device may be formed using any luminescent materials. For example, for a backlight in a liquid crystal display, metal complexes according to the present invention or any suitable materials selected from known luminescent materials may be so combined that they can be adapted to the wavelength range corresponding to the CF (color filter) characteristics and can produce white color.

Using the white organic electroluminescent device described above, an illumination device capable of emitting substantially white light can be obtained.

<<9. Illumination Device II>>

A plurality of organic electroluminescent devices according to the present invention may be used to form an illumination device having a large light-emitting surface. In this case, a plurality of light-emitting panels each having the organic electroluminescent device provided on a transparent substrate may be arranged (or tiled) on a support substrate to form a larger light-emitting surface. The support substrate may also serve as a sealant, and the light-emitting panels may be tiled in such a way that the organic electroluminescent devices are sandwiched between the support substrate and the transparent substrates of the light emitting panels. An adhesive may be applied between the support substrate and the transparent substrates in order to seal the organic electroluminescent devices. The terminals of the transparent electrodes and the counter electrodes should be exposed at the periphery of the light-emitting panels.

In the illumination device with such a structure, the central part of each light-emitting panel forms a light-emitting region, and a non-light-emitting region is formed between the light-emitting panels. Therefore, a light extraction member for increasing the amount of light extracted from the non-light-emitting region may be provided on the non-light-emitting region of the light extraction surface. A light condensing sheet or a light diffusion sheet may be used as the light extraction member.

Example 1

<<Preparation of Transparent Electrode>>

According to the composition shown in Table 2 below, each of transparent electrode samples 101 to 145 was prepared with a conductive region area of 5 cm×5 cm.

<Procedure for Preparing Transparent Electrode Samples 101 and 102>

As described below, each electrode layer of silver (Ag) with the thickness shown in Table 2 was formed as a transparent electrode on a glass substrate.

First, a transparent alkali-free glass substrate was fixed on a substrate holder for a commercially available vacuum deposition system, and the holder was then placed in the vacuum chamber of the vacuum deposition system. Silver (Ag) was added to a resistance heating tungsten boat, which was placed in the vacuum chamber. Subsequently, after the pressure in the vacuum chamber was reduced to $4 \times 10^{-4}$ Pa, the resistance heating boat was heated by passing a current through it, and an electrode layer of silver was formed with each thickness at a deposition rate of 0.1 nm/sec to 0.2 nm/sec. In sample 101, the electrode layer formed had a thickness of 6 nm. In sample 102, the electrode layer formed had a thickness of 15 nm.

<Procedure for Preparing Transparent Electrode Sample 103>

As described below, an electrode layer including silver (Ag) and aluminum (Al) as an additive was formed as a transparent electrode (see Table 2).

First, a transparent alkali-free glass substrate was fixed on a substrate holder for a commercially available vacuum deposition system. Silver (Ag) and aluminum (Al) were added to resistance heating tungsten boats, respectively. The substrate holder and the resistance heating tungsten boats were then placed in the vacuum chamber of the vacuum deposition system. Subsequently, after the pressure in the vacuum chamber was reduced to $4 \times 10^{-4}$ Pa, codeposition of silver (Ag) and aluminum (Al) was performed while the deposition rate was controlled by controlling the current to each resistance heating boat. In the codeposition, aluminum (Al) was added at a concentration of 20.0 at. % to silver (Ag) to form an alloy electrode layer with a thickness of 6 nm.

<Procedure for Preparing Transparent Electrode Sample 104>

As described below, an electrode layer with a multilayer structure of aluminum (Al) and silver (Ag) was formed as a transparent electrode (see Table 2).

First, a transparent alkali-free glass substrate was fixed on a substrate holder for a commercially available vacuum deposition system. Silver (Ag) and aluminum (Al) were added to resistance heating tungsten boats, respectively. The substrate holder and the resistance heating tungsten boats were then placed in the vacuum chamber of the vacuum deposition system. Subsequently, after the pressure in the vacuum chamber was reduced to $4 \times 10^{-4}$ Pa, the resistance heating boat containing aluminum (Al) was first heated by passing a current through it, and an aluminum (Al) film with a thickness of 0.1 nm was formed at a deposition rate of 0.1 nm/sec to 0.2 nm/sec. Subsequently, the resistance heating boat containing silver (Ag) was heated by passing a current through it, and a silver (Ag) film with a thickness of 6 nm was formed at a deposition rate of 0.1 nm/sec to 0.2 nm/sec, so that a two-layer structure electrode layer was formed.

<Procedure for Preparing Transparent Electrode Samples 105 to 113>

As described below, a transparent electrode with a two-layer structure was formed on a glass substrate. The two-layer structure was composed of: a nitrogen-containing layer including each material shown in Table 2; and an electrode layer of silver. In sample 105, a nitrogen-free underlying layer was formed instead of the nitrogen-containing layer.

First, a transparent alkali-free glass substrate was fixed on a substrate holder for a commercially available vacuum deposition system. For the preparation of each transparent electrode, each compound shown in Table 2 below was added to a resistance heating tantalum boat. The substrate holder and the resistance heating boat were then placed in a first vacuum chamber of the vacuum deposition system. Silver (Ag) was also added to a resistance heating tungsten boat, which was then placed in a second vacuum chamber.

Among the compounds used in this case, compound Nos. 1x to 5x are shown below, in which the nitrogen atom having an "effective lone pair" is marked by a circle. Compound No. 1x is anthracene with no nitrogen atom. Compound Nos. 2x to 5x have an effective lone pair content [n/M] of less than $2.0 \times 10^{-3}$ ($[n/M] < 2.0 \times 10^{-3}$) although they contain a nitrogen atom or atoms.

[Chemical Formula 74]

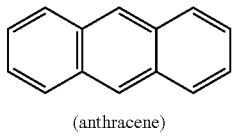

(anthracene)

No. 1x

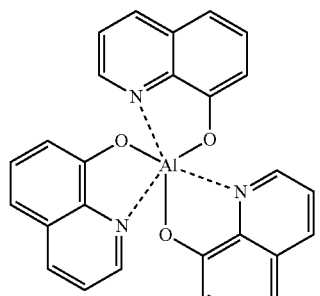

(Alq3)

No. 2x

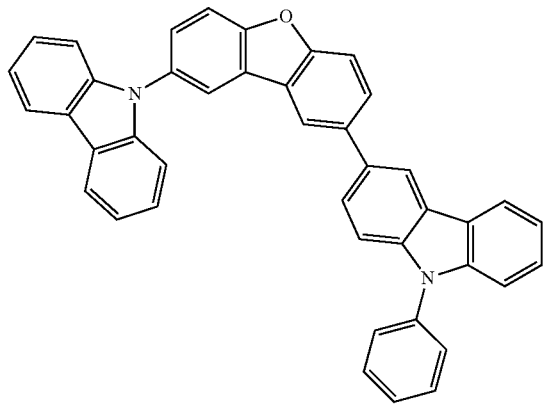

No. 3x

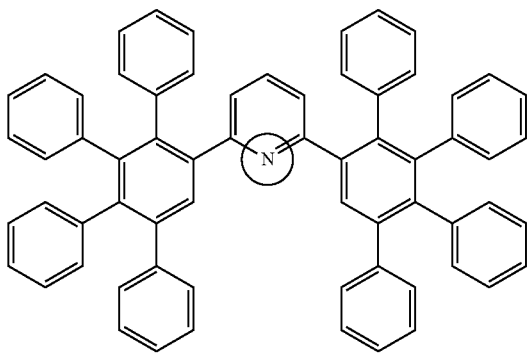

No. 4x

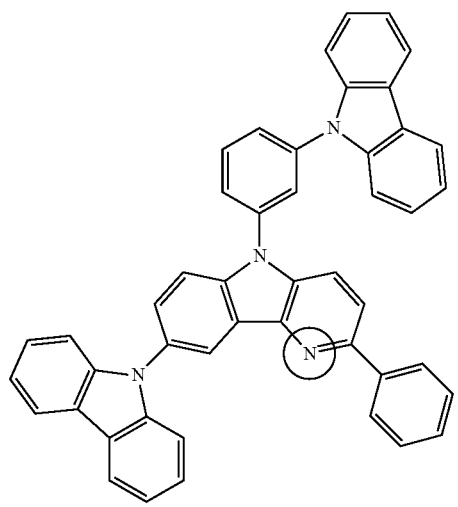

No. 5x

On the other hand, compound No. 1 and other compounds having an effective lone pair content of $2.0 \times 10^{-3}$ or more ($2.0 \times 10^{-3} \leq [n/M]$) are appropriately selected from the compounds shown in Table 1. Table 2 below also shows the number [n] of effective lone pairs, the molecular weight [M], and the effective lone pair content [n/M] with respect to the compounds used in this case.

Subsequently, after the pressure in the first vacuum chamber was reduced to $4 \times 10^{-4}$ Pa, the heating boat containing each compound was heated by passing a current through it, and a nitrogen-containing layer of each compound (an underlying layer in sample 105) with a thickness of 25 nm was formed on the substrate at a deposition rate of 0.1 nm/sec to 0.2 nm/sec.

Subsequently, the nitrogen-containing layer (underlying layer)-bearing substrate was transferred under vacuum to the second vacuum chamber. After the pressure in the second vacuum chamber was reduced to $4 \times 10^{-4}$ Pa, the heating boat containing silver was heated by passing a current through it. In this process, a silver electrode layer with a thickness of 6 nm was formed at a deposition rate of 0.1 nm/sec to 0.2 nm/sec, so that each of transparent electrode samples 105 to 113 was obtained, having a multilayer structure composed of the nitrogen-containing layer (underlying layer) and the electrode layer disposed thereon.

<Procedure for Preparing Transparent Electrode Samples 114 to 117>

According to Table 2 below, each transparent electrode with a two-layer structure was formed on a glass substrate as described below. The two-layer structure was composed of a nitrogen-containing layer of compound No. 1 and an electrode layer including silver (Ag) and aluminum (Al) as an additive element at each concentration. Compound No. 1 is an illustrative compound that has been shown to have an effective lone pair content [n/M] of $2.0 \times 10^{-3}$ or more ($[n/M] \geq 2.0 \times 10^{-3}$) in the section of embodiments. Table 2 below also shows the number [n] of effective lone pairs, the molecular weight [M], and the effective lone pair content [n/M] with respect to the compound used in this case.

First, a transparent alkali-free glass substrate was fixed on a substrate holder for a commercially available vacuum deposition system. For the preparation of each transparent electrode, compound No. 1 was added to a resistance heating tantalum boat. The substrate holder and the resistance heating boat were then placed in a first vacuum chamber of the vacuum deposition system. Silver (Ag) and aluminum (Al) were added to resistance heating tungsten boats, respectively. The substrate holder and the heating boats were then placed in a second vacuum chamber of the vacuum deposition system.

Subsequently, after the pressure in the first vacuum chamber was reduced to $4 \times 10^{-4}$ Pa, the heating boat containing compound No. 1 was heated by passing a current through it, and a nitrogen-containing layer of compound No. 1 with a thickness of 25 nm was formed on the substrate at a deposition rate of 0.1 nm/sec to 0.2 nm/sec.

Subsequently, the nitrogen-containing layer-bearing substrate was transferred under vacuum to the second vacuum chamber. After the pressure in the second vacuum chamber was reduced to $4 \times 10^{-4}$ Pa, codeposition of silver (Ag) and aluminum (Al) was performed while the deposition rate was controlled by controlling the current to each resistance heating boat. In the codeposition, an electrode layer of a solid solution including silver (Ag) and aluminum (Al) as an additive at each concentration was formed with a thickness of 6 nm. In this way, each of transparent electrode samples 114 to 117 was obtained, having the nitrogen-containing layer of compound No. 1 and the electrode layer stacked in this order, wherein the electrode layer includes silver (Ag) and aluminum (Al) as an additive element at each concentration.

<Procedure for Preparing Transparent Electrode Samples 118 to 139>

Transparent electrode samples 118 to 139 were each obtained using the same procedure as for samples 114 to 117 shown above, except for the following. Each compound shown in Table 2 below was used to form the nitrogen-containing layer. Aluminum (Al) as the additive element was added at a concentration of 5.0 at. % to the silver (Ag)-based electrode layer.

<Procedure for Preparing Transparent Electrode Samples 140 and 141>

Transparent electrode samples 140 and 141 were each obtained using the same procedure as for samples 114 to 117 shown above, except for the following. Each compound shown in Table 2 below was used to form the nitrogen-containing layer. The thickness of the silver (Ag)-based electrode layer was changed to 8 nm, and aluminum (Al) as the additive element was added at a concentration of 5.0 at. %.

<Procedure for Preparing Transparent Electrode Samples 142 and 143>

Transparent electrode samples 142 and 143 were each obtained using the same procedure as for samples 114 to 117 shown above, except for the following. A polyethylene terephthalate (PET) substrate was used instead, and each compound shown in Table 2 below was used to form the nitrogen-containing layer. The thickness of the silver (Ag)-based electrode layer was changed to 8 nm, and aluminum (Al) as the additive element was added at a concentration of 5.0 at. %.

<Procedure for Preparing Transparent Electrode Samples 144 and 145>

Transparent electrode samples 144 and 145 were each obtained using the same procedure as for samples 114 to 117 shown above, except that the nitrogen-containing layer was formed on a PET substrate by a coating method using each material shown in Table 2. Compound Nos. 7 and 14 used in this case are the illustrative compounds shown in the section of embodiments. The nitrogen-containing layer was formed by the following coating method.

Each compound was dissolved in a solvent of 1:1 toluene and TFP (trifluoroethyl phosphate) heated at 80° C., so that a coating liquid was obtained. The coating liquid was spin-coated on a PET substrate. In this process, the coating was performed at a rotation speed of 1,500 rpm for 30 seconds. The coating liquid was then dried by a heat treatment at 120° C. for 30 minutes to form a 25-nm-thick nitrogen-containing layer.

Thereafter, an 8-nm-thick electrode layer composed of silver (Ag) and aluminum (Al) as an additive element at a concentration of 5.0 at. % was formed on the nitrogen-containing layer, so that each of transparent electrode samples 144 and 145 was obtained, having a multilayer structure composed of the nitrogen-containing layer and the electrode layer disposed thereon.

<Evaluation of Each Sample in Example 1>

Transparent electrode samples 101 to 145 prepared as described above were each measured for (1) 550 nm wavelength light transmittance, (2) sheet resistance, and (3) storage stability at high temperature and high humidity.

(1) The light transmittance was measured with a spectrophotometer (U-3300 manufactured by Hitachi, Ltd.). The same substrate as that in the sample was used for the base line. (2) The sheet resistance was measured with a resistivity meter (MCP-T610 manufactured by Mitsubishi Chemical Corporation) by four-terminal four-probe method under constant current application. (3) The storage stability at high temperature and high humidity was measured as follows. Transparent electrode samples 101 to 145 were each stored in a high-temperature, high-humidity environment (temperature 60° C., humidity 90%) for 300 hours and then measured for sheet resistance. The ratio (increase rate) of the sheet resistance after the storage to the sheet resistance before the storage was calculated as a measure of high-temperature, high-humidity storage stability. The smaller the resulting value, the better the result. The results are also shown in Table 2.

TABLE 2

| Sample No. | Substrate Material | Composition | | | | | | | Evaluation results | | | |
|---|---|---|---|---|---|---|---|---|---|---|---|---|
| | | Nitrogen-containing layer (underlying layer) 25 nm in thickness | | | | Electrode layer | | | Light transmittance (%) (550 nm) | Sheet resistance (Ω/sq.) | High-temperature, high-humidity storage stability (resistance increase rate) | Note |
| | | Compound | Number [n] of lone pairs | Molecular weight [M] | [n/M] | Main material | Additive element | Additive element concentration (at. %) | Thickness (nm) | | | | |
| 101 | Glass | — | — | — | — | Ag | — | — | 6 | 45 | Unmeasurable | — | Comparative |

TABLE 2-continued

| Sample No. | Substrate Material | Nitrogen-containing layer (underlying layer) 25 nm in thickness | | | | Electrode layer | | | | Light trans-mittance (%) (550 nm) | Sheet resistance (Ω/sq.) | High-temperature, high-humidity storage stability (resistance increase rate) | Note |
|---|---|---|---|---|---|---|---|---|---|---|---|---|---|
| | | Compound | Number [n] of lone pairs | Molecular weight [M] | [n/M] | Main material | Additive element | Additive element concentration (at. %) | Thickness (nm) | | | | |
| 102 | | | | | | | | | 15 | 25 | 5 | 700% | Comparative |
| 103 | | | | | | Ag | Al | 20.0 | 6 | 50 | 150 | 500% | Comparative |
| 104 | | | | | | Ag/Al | — | — | 6/0.1 | 50 | 150 | 500% | Comparative |
| 105 | Glass | No. 1x (anthracene) | 0 | 178.23 | 0.0E+00 | Ag | — | — | 6 | 45 | Unmeasurable | — | Comparative |
| 106 | | No. 2x(Alq3) | 0 | 459.44 | 0.0E+00 | | | | | 50 | Unmeasurable | — | Comparative |
| 107 | | No. 3x | 0 | 574.67 | 0.0E+00 | | | | | 46 | Unmeasurable | — | Comparative |
| 108 | | No. 4x | 1 | 839 | 1.2E-03 | | | | | 47 | Unmeasurable | — | Comparative |
| 109 | | No. 5x | 1 | 650.77 | 1.5E-03 | | | | | 48 | Unmeasurable | — | Comparative |
| 110 | | No. 1 | 1 | 500.55 | 2.0E-03 | | | | | 55 | 280 | 200% | Comparative |
| 111 | | No. 39 | 3 | 537.65 | 5.6E-03 | | | | | 60 | 50 | 150% | Comparative |
| 112 | | No. 40 | 2 | 332.4 | 5.0E-03 | | | | | 60 | 45 | 130% | Comparative |
| 113 | | No. 38 | 4 | 538.64 | 7.4E-03 | | | | | 60 | 30 | 120% | Comparative |
| 114 | Glass | No. 1 | 1 | 500.55 | 2.0E-03 | Ag | Al | 0.01 | 5 | 54 | 280 | 105% | Inventive |
| 115 | | | | | | | | 5.0 | | 55 | 280 | 100% | Inventive |
| 116 | | | | | | | | 10.0 | | 56 | 280 | 100% | Inventive |
| 117 | | | | | | | | 20.0 | | 52 | 310 | 110% | Inventive |
| 118 | Glass | No. 4 | 2 | 655.81 | 3.0E-03 | Ag | Al | 5.0 | 6 | 60 | 180 | 100% | Inventive |
| 119 | | No. 39 | 3 | 537.65 | 5.6E-03 | | | | | 60 | 50 | 100% | Inventive |
| 120 | | No. 40 | 2 | 332.4 | 6.0E-03 | | | | | 60 | 45 | 100% | Inventive |
| 121 | | No. 38 | 4 | 538.64 | 7.4E-03 | | | | | 60 | 30 | 100% | Inventive |
| 122 | | No. 7 | 4 | 716.83 | 5.6E-03 | | | | | >70 | 25 | 100% | Inventive |
| 123 | | No. 8 | 6 | 1036.19 | 5.8E-03 | | | | | >70 | 24 | 100% | Inventive |
| 124 | | No. 9 | 4 | 551.64 | 7.3E-03 | | | | | >70 | 23 | 100% | Inventive |
| 125 | | No. 10 | 4 | 516.6 | 7.7E-03 | | | | | >70 | 20 | 100% | Inventive |
| 126 | | No. 11 | 5 | 539.63 | 9.3E-03 | | | | | >70 | 19 | 100% | Inventive |
| 127 | | No. 12 | 6 | 646.76 | 9.3E-03 | | | | | >70 | 20 | 100% | Inventive |
| 128 | | No. 13 | 4 | 412.45 | 9.7E-03 | | | | | >70 | 19 | 100% | Inventive |
| 129 | | No. 14 | 6 | 616.71 | 9.7E-03 | | | | | >70 | 19 | 100% | Inventive |
| 130 | | No. 15 | 5 | 463.53 | 1.1E-02 | | | | | >70 | 16 | 100% | Inventive |
| 131 | | No. 18 | 6 | 312.33 | 1.9E-02 | | | | | >70 | 12 | 100% | Inventive |
| 132 | | No. 41 | 4 | 502.15 | 8.0E-03 | | | | | >70 | 19 | 100% | Inventive |
| 133 | | No. 42 | 6 | 579.19 | 1.0E-02 | | | | | >70 | 17 | 100% | Inventive |
| 134 | | No. 43 | 3 | 653.22 | 4.6E-03 | | | | | >70 | 51 | 100% | Inventive |
| 135 | | No. 44 | 4 | 567.21 | 6.0E-03 | | | | | >70 | 40 | 100% | Inventive |
| 136 | | No. 45 | 6 | 579.19 | 1.0E-02 | | | | | >70 | 16 | 100% | Inventive |
| 137 | | No. 46 | 3 | 576.65 | 5.2E-03 | | | | | >70 | 17 | 100% | Inventive |
| 138 | | No. 47 | 3 | 545.55 | 5.5E-03 | | | | | >70 | 18 | 100% | Inventive |
| 139 | | No. 48 | 6 | 379.38 | 1.6E-02 | | | | | >70 | 15 | 100% | Inventive |
| 140 | Glass | No. 7 | 4 | 716.83 | 5.6E-03 | Ag | Al | 5.0 | 8 | >70 | 8 | 100% | Inventive |
| 141 | | No. 14 | 6 | 616.71 | 9.7E-03 | | | | | >70 | 7 | 100% | Inventive |
| 142 | PET | No. 7 | 4 | 716.83 | 5.6E-03 | Ag | Al | 5.0 | 8 | >70 | 8 | 100% | Inventive |
| 143 | | No. 14 | 6 | 616.71 | 9.7E-03 | | | | | >70 | 7 | 100% | Inventive |
| 144 | PET | No. 7 (coating) | 4 | 716.83 | 5.6E-03 | Ag | Al | 5.0 | 8 | >70 | 6 | 100% | Inventive |
| 145 | | No. 14 (coating) | 6 | 616.71 | 9.7E-03 | | | | | >70 | 7 | 100% | Inventive |

<Results of Valuation of Example 1>

In Table 2, transparent electrode samples 114 to 145 each include a nitrogen-containing layer of one of compound No. 1 and other compounds with an effective lone pair content [n/M] of $2.0 \times 10^{-3}$ or more ($2.0 \times 10^{-3} \leq [n/M]$) and an electrode layer provided adjacent thereto and including silver (Ag) as a main component and aluminum (Al) as a solid solution-forming additive element. Table 2 shows that transparent electrode samples 114 to 145 each have a measurable sheet resistance although the silver-based electrode layer for substantial conductivity is a very thin film of 6 nm or 8 nm, which demonstrates that the electrode layer is formed with a substantially uniform thickness in a monolayer growth mode (Frank van der Merwe (FM) mode). It has also been found that transparent electrode samples 114 to 145 have a light transmittance of 50% or more and thus are practical.

Transparent electrode samples 114 to 145 also have a value of almost 100% for high-temperature, high-storage storage stability, which demonstrates that they have high durability at high temperature and high humidity.

The same results were obtained regardless of whether the substrate was glass or a plastic material (PET). Transparent electrode samples 114 to 145 have a light transmittance of 50% or more regardless of whether the electrode layer is 6 nm or 8 nm in thickness, and a reduction in sheet resistance is observed when the thickness of the electrode layer is increased from 6 nm to 8 nm, which demonstrates that the light transmittance and the conductivity can be improved at the same time. Sample 102 without any nitrogen-containing layer or underlying layer has an electrode layer thickness as high as 15 nm and thus is low in light transmittance and not usable as a transparent electrode although having a low sheet resistance.

It has also been found that each of transparent electrode samples 114 to 116, in which only the concentration of the additive element in the electrode layer is varied in the range of 0.01 to 10.0 at. % in the structure of samples 114 to 145, has a high light transmittance, a low sheet resistance (300 Ω/square or less), and high storage stability at high temperature and high humidity.

It has also been found that transparent electrode sample 138, having a nitrogen-containing layer of compound No. 47 with a nitro group, shows good results for light transmittance, sheet resistance, and high-temperature, high-humidity storage stability. This demonstrates that the lone pair of a nitro group (—$NO_2$), although used for the resonance structure, is a lone pair neither contributing to aromaticity nor being coordinated to metal and effective as an "effective lone pair" in bonding with silver (Ag).

Figure 11:
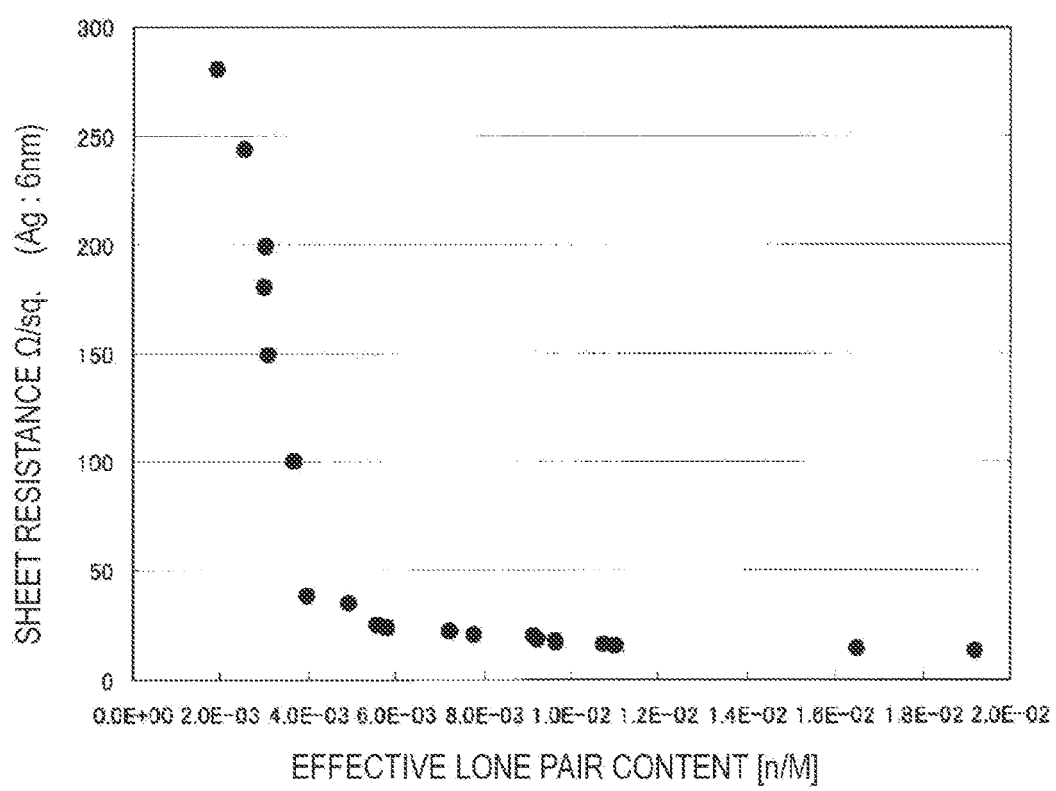
FIG. 11 is a graph illustrating the relationship between the effective lone pair content [n/M] of a nitrogen-containing layer and the sheet resistance of an electrode layer disposed on the nitrogen-containing layer.

FIG. 11 shows a graph obtained by plotting the effective lone pair content [n/M] of the compound used to form the nitrogen-containing layer against the measured sheet resistance of each transparent electrode with respect to the transparent electrodes having a 6-nm-thick silver (Ag) electrode layer provided on the nitrogen-containing layer of one of compound Nos. 1 to 20 with an effective lone pair content [n/M] of $2.0 \times 10^{-3}$ to $1.9 \times 10^{-2}$ ($2.0 \times 10^{-3} \leq [n/M] \leq 1.9 \times 10^{-2}$).

The graph of FIG. 11 shows that the sheet resistance of the transparent electrode tends to decrease as the effective lone pair content [n/M] increases in the range of $2.0 \times 10^{-3}$ to $1.9 \times 10^{-2}$ ($2.0 \times 10^{-3} \leq [n/M] \leq 1.9 \times 10^{-2}$). It has also been found that in the range $3.9 \times 10^{-3} \leq [n/M]$, the effect of dramatically reducing the sheet resistance can be achieved as the effective lone pair content [n/M] is increased from $3.9 \times 10^{-3}$. It has also been found that when the effective lone pair content [n/M] is $6.5 \times 10^{-3}$ or more ($6.5 \times 10^{-3} \leq [n/M]$), the effect of reducing the sheet resistance can be ensured.

The same results were obtained for the samples whose nitrogen-containing layer was formed by the coating method. The same results were also obtained for the samples whose nitrogen-containing layer was formed of a mixture of a nitrogen-containing compound and an additional compound.

It is apparent from the above that when the compound is selected based on its effective lone pair content [n/M] as an index and used to form the nitrogen-containing layer adjacent to the electrode layer, the resulting electrode film (namely, the resulting transparent electrode) has low resistance while it is thin enough to be optically transparent.

Example 2

<<Preparation of Bottom Emission Organic Electroluminescent Device>>

Figure 12:
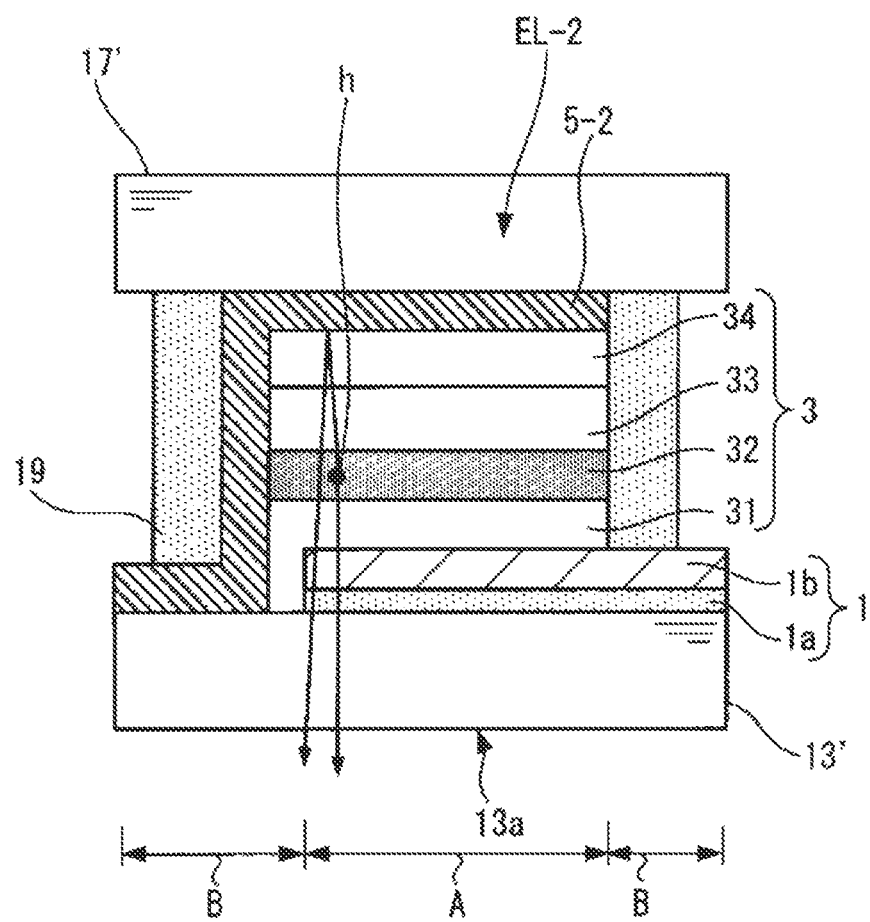
FIG. 12 is a cross-sectional view illustrating the structure of a bottom emission organic electroluminescent device prepared in Example 2.

Each transparent electrode was formed according to the composition shown in Table 3 below. Bottom emission organic electroluminescent device samples 201 to 231 were each prepared using the transparent electrode as an anode, which was provided on the lower side of the light-emitting functional layer. The procedure for the preparation will be described with reference to FIG. 12. Table 3 shows the composition of the transparent electrodes used to form organic electroluminescent device samples 201 to 231.

<Procedure for Preparing Organic Electroluminescent Device Samples 201 to 231>

(Formation of Transparent Electrode 1)

For samples 201 to 231, each transparent electrode of the composition shown in Table 3 below was formed on the top of a transparent substrate 13' made of transparent PET. The transparent electrode of each structure was formed using the same procedure as for the transparent electrode of the corresponding structure in Example 1.

(Formation of Hole Transport/Injection Layer 31)

First, a heating boat containing α-NPD of the structural formula shown below as a hole transport/injection material was heated by passing a current through it so that a hole transport/injection layer 31 of α-NPD for serving as both a hole injection layer and a hole transport layer was formed on the transparent electrode 1. In this process, the deposition rate was 0.1 nm/sec to 0.2 nm/sec, and the thickness of the layer was 20 nm.

[Chemical Formula 75]

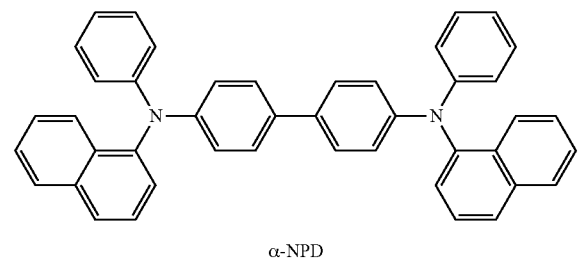

α-NPD (Formation of Light-Emitting Layer 32)

Subsequently, a heating boat containing host material H-1 of the structural formula shown below and a heating boat containing phosphorescence-emitting compound Ir1 of the structural formula shown below were each independently energized so that a light-emitting layer 32 composed of host material H-1 and phosphorescence-emitting compound Ir1 was formed on the hole transport/injection layer 31. In this process, the passage of current through the heating boats was controlled so that the deposition rate ratio of host material H-1 to phosphorescence-emitting compound Ir1 was 100:6. The thickness of the layer was 30 nm.

[Chemical Formula 76]

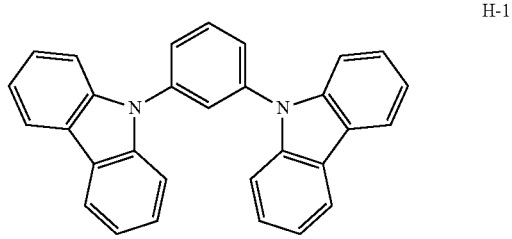

H-1

-continued

Ir1

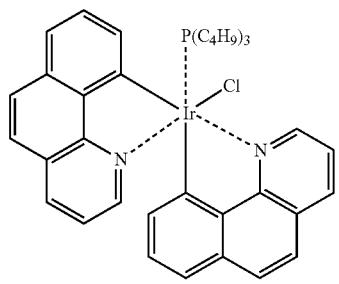

(Formation of Hole-Blocking Layer 33)

Subsequently, a heating boat containing BAlq of the structural formula shown below as a hole-blocking material was heated by passing a current through it so that a hole-blocking layer 33 of BAlq was formed on the light-emitting layer 32. In this process, the deposition rate was 0.1 nm/sec to 0.2 nm/sec, and the thickness of the layer was 10 nm.

[Chemical Formula 77]

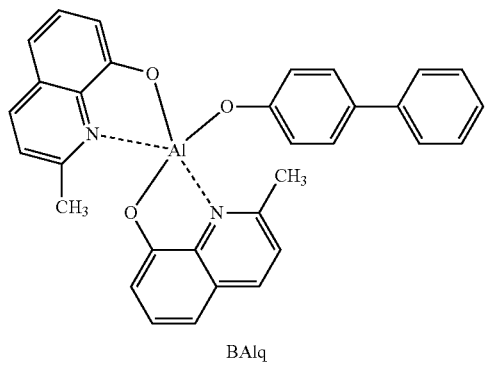

BAlq (Formation of Electron Transport/Injection Layer 34)

Subsequently, a heating boat containing compound 10 of the structural formula shown above as an electron transport material and a heating boat containing potassium fluoride were each independently energized so that an electron transport/injection layer 34 composed of compound 10 and potassium fluoride for serving as both an electron injection layer and an electron transport layer was formed on the hole-blocking layer 33. In this process, the passage of current through the heating boats was controlled so that the deposition rate ratio of compound 10 to potassium fluoride was 75:25. The thickness of the layer was 30 nm. Compound 10 corresponds to compound No. 7 with an effective lone pair content [n/M] in the specified range.

(Formation of Counter Electrode 5-2 (Formation of Cathode))

After the process, the light-emitting functional layer 3-bearing transparent substrate 13' was transferred into a second vacuum chamber of the vacuum deposition system. After the pressure in the second vacuum chamber was reduced to $4 \times 10^{-4}$ Pa, a heating boat containing aluminum, placed in the second vacuum chamber, was heated by passing a current through it. In this process, a counter electrode 5-2 of aluminum with a thickness of 100 nm was formed at a deposition rate of 0.3 nm/sec. The counter electrode 5-2 is used as a cathode. In this way, a bottom emission organic electroluminescent device EL-2 was formed on the transparent substrate 13'.

(Sealing of Device)

Subsequently, the organic electroluminescent device EL-2 was covered with a sealant 17' of a 300-μm-thick glass base material. While the organic electroluminescent device EL-2 was covered, an adhesive 19 (sealing material) was applied between the sealant 17' and the transparent substrate 13'. The adhesive 19 used was a photo-curing epoxy adhesive (LUX-TRAK LC0629B manufactured by Toagosei Co., Ltd.). The adhesive 19 applied between the sealant 17' and the transparent substrate 13' was irradiated with UV light from the glass base material sealant 17' side, so that the adhesive 19 was cured to seal the organic electroluminescent device EL-2.

In the process of forming the organic electroluminescent device EL-2, a vapor deposition mask was used in the formation of each layer, so that a 4.5 cm×4.5 cm light-emitting region A was formed at the center of the 5 cm×5 cm transparent substrate 13', and a non-light-emitting region B with a width of 0.25 cm was formed around the whole of the light-emitting region A. The electrode layer 1b of the transparent electrode 1 as an anode was formed to have a terminal part extending to the edge of the transparent substrate 13', while it was insulated from the counter electrode 5-2 as a cathode with the components from the hole transport/injection layer 31 to the electron transport/injection layer 34.

In this way, each of light-emitting panels of organic electroluminescent device samples 201 to 231 was obtained, which had the organic electroluminescent device EL-2 provided on the transparent substrate 13' and sealed with the sealant 17' and the adhesive 19. In each light-emitting panel, emitted light h of each color produced by the light-emitting layer 32 is extracted from the transparent substrate 13' side.

<Evaluation of Each Sample in Example 2>

The prepared organic electroluminescent device EL-2 samples 201 to 231 (light-emitting panels) were evaluated for (1) driving voltage, (2) luminance uniformity, and (3) storage stability at high temperature and high humidity, respectively. The results are also shown in Table 3.

(1) In the measurement, the driving voltage was determined as the voltage obtained when the front luminance on the transparent electrode 1 side (namely, the transparent substrate 13' side) of each organic electroluminescent device EL-2 reached 1,000 cd/m². The luminance was measured with a spectral radiance meter CS-1000 (manufactured by Konica Minolta Sensing Co., Ltd.). The smaller the measured driving voltage, the better the result.

(2) The luminance uniformity was evaluated as follows. A current of 2.5 mA/cm² was applied to each organic electroluminescent device EL-2 when the luminance at the center of the light-emitting surface (the central luminance) on the transparent electrode 1 side (namely, the transparent substrate 13' side) and the luminance at an end part close to the feeding point (the end luminance) on the transparent electrode 1 side were measured. The luminance was measured with the spectral radiance meter CS-1000 (manufactured by Konica Minolta Sensing Co., Ltd.). The ratio of the measured central luminance to the measured end luminance was calculated as the degree of luminance uniformity. Therefore, the closer to 100% the degree of luminance uniformity is, the better the result.

(3) The storage stability at high temperature and high humidity was evaluated as follows. Ten pieces of each of sealed organic electroluminescent device EL-2 samples 201 to 231 were prepared and stored in a high-temperature, high-humidity environment. The pieces of each sample were then evaluated for (a) the number (/10 pieces) of light-emitting pieces, (b) the difference [ΔV] between the driving voltages of each piece before and after the storage, and (c) rectification ratio [log]. The high-temperature, high-humidity environment was at a temperature of 60° C. and a humidity of 90%, and the storage time was 300 hours. During the storage, each organic electroluminescent device EL-2 was driven at a driving voltage for a luminance of 1,000 cd. (a) The number (/10 pieces) of light-emitting pieces was the number of pieces of each of samples 201 to 231 from which light emission was observed also after the storage of the 10 pieces of each sample for 300 hours. The closer to 10 the number is, the better the result. (b) The driving voltage difference [ΔV] was calculated as an average change in the driving voltage measured for the pieces of each of organic electroluminescent device EL-2 samples 201 to 231 from which light emission was observed after the storage. The smaller the calculated value, the better the result. (c) The rectification ratio [log] was determined as follows. After the storage, the current values were measured when a forward driving voltage of +2.5 V was applied to each light-emitting panel and when a backward driving voltage of −2.5 V was applied to each light-emitting panel. The rectification ratio [log] was calculated as the logarithm of the ratio between the current values [(the current value at +2.5 V)/(the current value at −2.5 V)]. The higher the rectification ratio [log], the better the leakage characteristics. The results are also shown in Table 3 below.

<Results of Evaluation in Example 2>

In Table 3, organic electroluminescent device EL-2 samples 206 to 231 each has the transparent electrode 1 including the nitrogen-containing layer 1a of a compound with an effective lone pair content [n/M] of $2.0\times10^{-3}$ or more ($2.0\times10^{-3} \leq [n/M]$) and the electrode layer 1b provided adjacent thereto and including silver (Ag) as a main component and aluminum (Al) as a solid-solution-forming additive element. Table 3 show that organic electroluminescent device EL-2 samples 206 to 231 can emit light with a front luminance of 1,000 cd/m² at a driving voltage of 10 V or less, specifically, a driving voltage of as low as 6 V or less.

In organic electroluminescent device EL-2 samples 206 to 231, the luminance uniformity in the light-emitting surface is 90% or more, which demonstrates that variations in the luminance are kept at low level. After the storage in the high-temperature, high-humidity environment, light emission was observed from all the ten pieces of each of organic electroluminescent device EL-2 samples 206 to 231. The driving voltage difference [ΔV] between before and after the storage of samples 206 to 231 is 2.3 V or less, and the rectification ratio [log] after the storage of samples 206 to 231 is satisfactory so that leakage is suppressed. These results demonstrate that samples 206 to 231 have high storage stability at high temperature and high humidity.

TABLE 3

| | Composition of transparent electrode (anode (lower electrode)) | | | | | | Evaluation results | | | | | |
|---|---|---|---|---|---|---|---|---|---|---|---|---|
| | Nitrogen-containing layer (underlying layer) 25 nm | | Electrode layer | | | | | | High-temperature high-humidity storage stability | | | |
| | | | Main | Additive | Additive element concentration (at. %) | Thickness (nm) | Driving voltage (V) | Luminance uniformity | Number (/10 pieces) of light-emitting pieces | Driving voltage difference (ΔV) | Rectification ratio [log] | |
| Sample No. | Compound | [n/M] | material | element | | | | | | | | Note |
| 201 | — | — | Ag | Al | 20.0 | 6 | 8 | 60% | 3 | >10 | 3 | Comparative |
| 202 | | | Ag/Al | — | — | 6/0.1 | 7 | 55% | 2 | >10 | 3 | Comparative |
| 203 | No. 2x(Alq3) | 0.0E+00 | Ag | — | — | 6 | >10 | <50% | No emission | | | Comparative |
| 204 | No. 4x | 1.2E−03 | | | | | >10 | <50% | No emission | | | Comparative |
| 205 | No. 39 | 5.6E−03 | | | | | 6.5 | 90% | 6 | 6 | 2 | Comparative |
| 206 | No. 39 | 5.6E−03 | Ag | Al | 0.01 | 6 | 6 | 93% | 10 | 2.1 | 4 | Inventive |
| 207 | | | | | 5.0 | | 6 | 92% | 10 | 2 | 4 | Inventive |
| 208 | | | | | 10.0 | | 6 | 92% | 10 | 2 | 4 | Inventive |
| 209 | | | | | 20.0 | | 6 | 90% | 10 | 2.3 | 4 | Inventive |
| 210 | No. 6 | 3.7E−03 | Ag | Al | 5.0 | 6 | 5.5 | 97% | 10 | 1.5 | 4 | Inventive |
| 211 | No. 7 | 5.6E−03 | | | | | <5 | 98% | 10 | <1 | 5 | Inventive |
| 212 | No. 8 | 5.8E−03 | | | | | <5 | 98% | 10 | <1 | 5 | Inventive |
| 213 | No. 9 | 7.3E−03 | | | | | <5 | 99% | 10 | <1 | 5 | Inventive |
| 214 | No. 10 | 7.7E−03 | | | | | <5 | 99% | 10 | <1 | 5 | Inventive |
| 215 | No. 11 | 9.3E−03 | | | | | <5 | 99% | 10 | <1 | 5 | Inventive |
| 216 | No. 12 | 9.3E−03 | | | | | <5 | 99% | 10 | <1 | 5 | Inventive |
| 217 | No. 13 | 9.7E−03 | | | | | <5 | 99% | 10 | <1 | 5 | Inventive |
| 218 | No. 14 | 9.7E−03 | | | | | <5 | 99% | 10 | <1 | 5 | Inventive |
| 219 | No. 15 | 1.1E−02 | | | | | <5 | 99% | 10 | <1 | 5 | Inventive |
| 220 | No. 41 | 8.0E−03 | | | | | <5 | 99% | 10 | <1 | 5 | Inventive |
| 221 | No. 42 | 1.0E−02 | | | | | <5 | 99% | 10 | <1 | 5 | Inventive |
| 222 | No. 43 | 4.6E−03 | | | | | <5 | 99% | 10 | <1 | 5 | Inventive |
| 223 | No. 44 | 6.0E−03 | | | | | <5 | 99% | 10 | <1 | 5 | Inventive |
| 224 | No. 45 | 1.0E−02 | | | | | <5 | 99% | 10 | <1 | 5 | Inventive |
| 225 | No. 46 | 5.2E−03 | | | | | <5 | 99% | 10 | <1 | 5 | Inventive |
| 226 | No. 47 | 5.5E−03 | | | | | <5 | 99% | 10 | <1 | 5 | Inventive |
| 227 | No. 48 | 1.6E−03 | | | | | <5 | 99% | 10 | <1 | 5 | Inventive |
| 228 | No. 18 | 1.9E−02 | | | | | <5 | 99% | 10 | <1 | 5 | Inventive |
| 229 | No. 7 | 5.6E−03 | Ag | Al | 5.0 | 8 | <5 | 99% | 10 | <1 | 5 | Inventive |
| 230 | No. 14 | 9.7E−03 | | | | | <5 | 99% | 10 | <1 | 5 | Inventive |
| 231 | No. 14 (coating) | 9.7E−03 | Ag | Al | 5.0 | 8 | <5 | 99% | 10 | <1 | 5 | Inventive |

It is apparent from the above that the organic electroluminescent device EL-2 having the transparent electrode 1 configured according to the present invention can emit light with high luminance at a low driving voltage and has high long-term reliability. This also indicates the potential for reducing driving voltage for a certain level of luminance and the potential for improving emission lifetime.

Example 3

Transparent electrode samples 114 to 145 prepared in Example 1 according to the structure of the present invention were each used as an anode to form white bottom emission organic electroluminescent devices, in which the anode was provided on the lower side of the light-emitting functional layer. Each prepared organic electroluminescent device was evaluated as in Example 2. As a result, it has been found that as in Example 2, variations in luminance are kept at small level and high storage stability at high temperature and high humidity is achieved. Thus, it has been demonstrated that the structure of the present invention is also advantageously effective in providing white light-emitting organic electroluminescent devices.

In Example 3, each white light-emitting organic electroluminescent device was prepared by the procedure shown below.

First, each of transparent electrode samples 114 to 145 in Example 1 according to the structure of the present invention was formed as an anode on a transparent glass substrate with a size of 30 mm×30 mm and a thickness of 0.7 mm. Each anode-bearing transparent substrate was then fixed on the substrate holder of a commercially available vapor deposition system.

On the other hand, each vapor deposition crucible in the vacuum deposition system was charged with the material, for each layer to be subsequently formed, in an amount optimal for the preparation of each device. Each crucible was fixed in the vacuum deposition system. The vapor deposition crucible used was made of a molybdenum or tungsten material for resistance heating.

Subsequently, after the pressure in the vacuum deposition system was reduced to a degree of vacuum of $1 \times 10^{-4}$ Pa, the vapor deposition crucible containing α-NPD shown above was heated by passing a current through it, and α-NPD was vapor-deposited at a deposition rate of 0.1 nm/sec to form a 40-nm-thick hole injection/transport layer on the transparent electrode.

Subsequently, compound BD-1 shown below as a blue light-emitting dopant and compound H-2 shown below as a host compound were co-vapor-deposited at a deposition rate of 0.1 nm/sec in such a way that compound BD-1 was at a concentration of 5%, so that a 15-nm-thick fluorescent light-emitting layer for blue emission was formed.

[Chemical Formula 78]

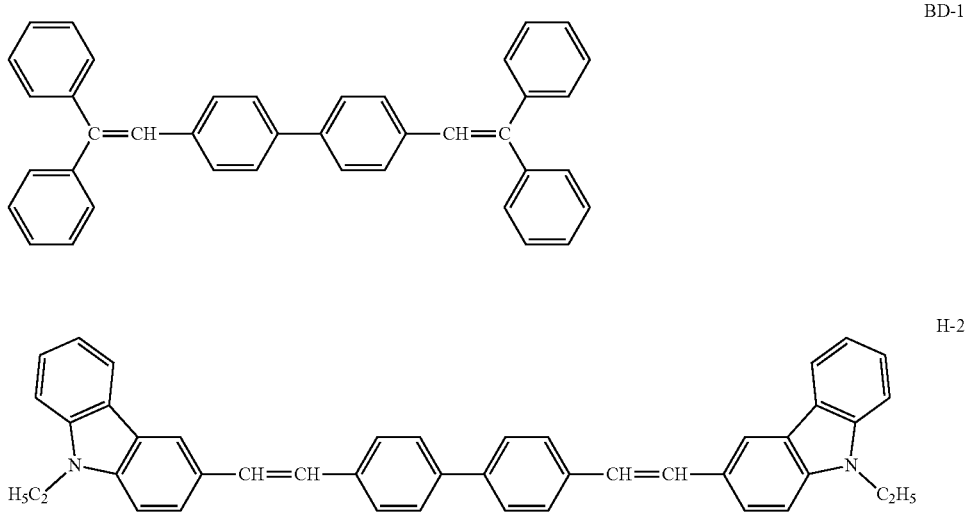

BD-1

H-2

Subsequently, compound GD-1 shown below as a green light-emitting dopant, compound RD-1 shown below as a red light-emitting dopant, and compound H-3 shown below as a host compound were co-vapor-deposited at a deposition rate of 0.1 nm/sec in such a way that compound GD-1 and compound RD-1 were at concentrations of 17% and 0.8%, respectively, so that a 15-nm-thick phosphorescent light-emitting layer for yellow color was formed. Compound GD-1 corresponds to compound D-15 shown above as a light-emitting dopant, and compound RD-1 corresponds to compound D-1 shown above as a light-emitting dopant.

[Chemical Formula 79]

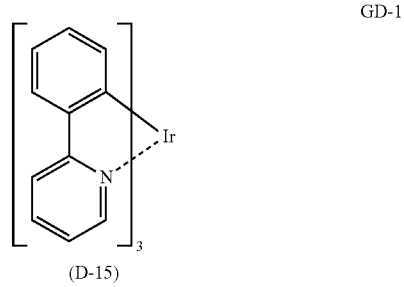

GD-1

(D-15)

-continued

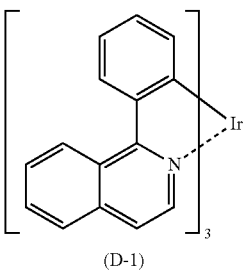
(D-1)

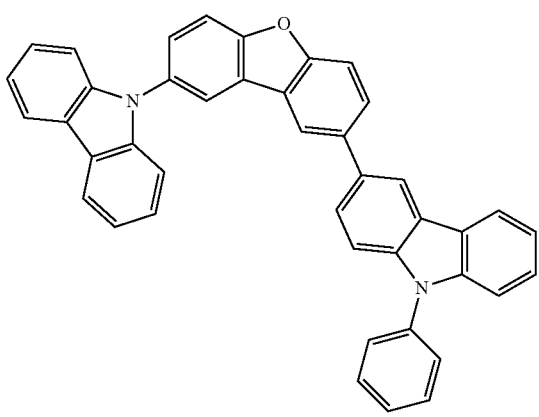
(No. 3x)

Subsequently, compound E-1 shown below was vapor-deposited at a deposition rate of 0.1 nm/sec so that a 30-nm-thick electron transport layer was formed. Compound E-1 corresponds to compound 10 shown above as a material for the nitrogen-containing layer.

[Chemical Formula 80]

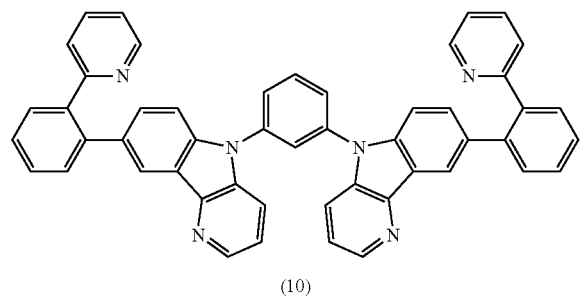
(10)

Subsequently, after a 1.5-nm-thick LiF film was formed, aluminum was vapor-deposited with a thickness of 110 nm to form a cathode.

The non-light-emitting surface of the resulting device was then covered with a glass case, so that each organic electroluminescent device was obtained.

Example 4

Transparent electrode samples 114 to 145 prepared in Example 1 according to the structure of the present invention were each used as an anode to form white light-emitting tandem organic electroluminescent devices, in which the anode was provided on the lower side of the light-emitting functional layer. Each prepared organic electroluminescent device was evaluated as in Example 2. As a result, it has been found that as in Example 2, variations in luminance are kept at small level and high storage stability at high temperature and high humidity is achieved. Thus, it has been demonstrated that the structure of the present invention is also advantageously effective in providing tandem organic electroluminescent devices.

In Example 4, each tandem organic electroluminescent device was prepared by the procedure shown below.

First, each of transparent electrode samples 114 to 145 in Example 1 according to the structure of the present invention was formed as an anode on a transparent glass substrate with a size of 30 mm×30 mm and a thickness of 0.7 mm. Each anode-bearing transparent substrate was then fixed on the substrate holder of a commercially available vapor deposition system.

On the other hand, each vapor deposition crucible in the vacuum deposition system was charged with the material, for each layer to be subsequently formed, in an amount optimal for the preparation of each device. Each crucible was fixed in the vacuum deposition system. The vapor deposition crucible used was made of a molybdenum or tungsten material for resistance heating.

Subsequently, after the pressure in the vacuum deposition system was reduced to a degree of vacuum of $1 \times 10^{-4}$ Pa, the vapor deposition crucible containing α-NPD shown above was heated by passing a current through it, and α-NPD was vapor-deposited at a deposition rate of 0.1 nm/sec to form a 40-nm-thick hole injection/transport layer on the transparent electrode.

Subsequently, compound BD-1 shown above as a blue light-emitting dopant and compound H-2 shown above as a host compound were co-vapor-deposited at a deposition rate of 0.1 nm/sec in such a way that compound BD-1 was at a concentration of 5%, so that a 30-nm-thick fluorescent light-emitting layer for blue emission was formed.

Subsequently, compound E-1 shown above was vapor-deposited at a deposition rate of 0.1 nm/sec so that a 30-nm-thick electron transport layer was formed.

Subsequently, a 1-nm-thick lithium film was vapor-deposited to form an intermediate metal layer.

Subsequently, α-NPD shown above was vapor-deposited at a deposition rate of 0.1 nm/sec to form a 50-nm-thick hole injection/transport layer.

Subsequently, compound GD-1 shown above as a green light-emitting dopant, compound RD-1 shown above as a red light-emitting dopant, and compound H-3 shown above as a host compound were co-vapor-deposited at a deposition rate of 0.1 nm/sec in such a way that compound GD-1 and compound RD-1 were at concentrations of 17% and 0.8%, respectively, so that a 30-nm-thick phosphorescent light-emitting layer for yellow color was formed.

Subsequently, compound E-1 shown above was vapor-deposited at a deposition rate of 0.1 nm/sec so that a 30-nm-thick electron transport layer was formed.

Subsequently, after a 1.5-nm-thick LiF film was formed, aluminum was vapor-deposited with a thickness of 110 nm to form a cathode.

The non-light-emitting surface of the resulting device was then covered with a glass case, so that each organic electroluminescent device was obtained.

REFERENCE SIGNS LIST 1 transparent electrode, 1a nitrogen-containing layer, 1b electrode layer, EL-1, EL-2, EL-3, EL-4 organic electroluminescent device (electronic device)

The invention claimed is:

1. A transparent electrode comprising:
a nitrogen-containing layer comprising a compound that contains a nitrogen atom or atoms (N) having an unshared electron pair or pairs and has an effective lone pair content n/M of $2.0\times10^{-3}$ or more, wherein n represents the number of unshared electron pairs that neither contribute to aromaticity nor are coordinated to metal among the unshared electron pair or pairs of the nitrogen atom or atoms, and M represents the molecular weight of the compound;
an electrode layer provided adjacent to the nitrogen-containing layer and comprising silver (Ag) as a main component and at least one additive element selected from aluminum (Al), gold (Au), indium (In), copper (Cu), palladium (Pd), and platinum (Pt); and
the nitrogen-containing layer further comprises a compound having a structure represented by Formula (1):

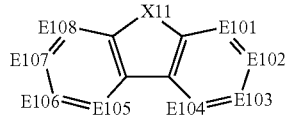

Formula (1)

wherein
X11 represents —N(R11)- or —O—,
E101 to E108 each represent —C(R12)= or —N=, at least one of E101 to E108 is —N=, and
R11 and R12 each represent a hydrogen atom (H) or a substituent.

2. The transparent electrode according to claim 1, wherein the compound having a structure represented by Formula (1) has a structure represented by Formula (1a):

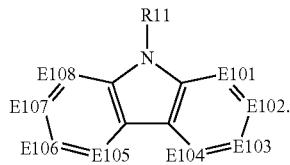

Formula (1a)

3. The transparent electrode according to claim 2, wherein the compound having a structure represented by Formula (1a) has a structure represented by Formula (1a-1):

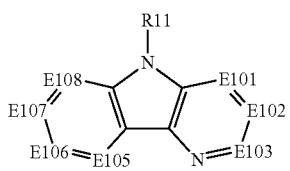

Formula (1a-1)

4. The transparent electrode according to claim 2, wherein the compound having a structure represented by Formula (1a) has a structure represented by Formula (1a-2):

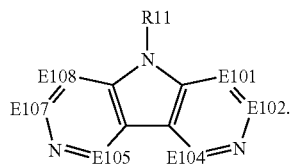

Formula (1a-2)

5. The transparent electrode according to claim 2, wherein the compound containing a nitrogen atom or atoms (N) has a structure represented by Formula (1a).

6. The transparent electrode according to claim 1, wherein the compound having a structure represented by Formula (1) has a structure represented by Formula (1b):

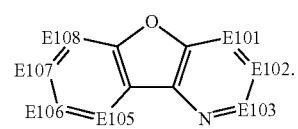

Formula (1b)

7. The transparent electrode according to claim 6, wherein the compound containing a nitrogen atom or atoms (N) has a structure represented by Formula (1b).

8. The transparent electrode according to claim 1, wherein the compound having a structure represented by Formula (1) has a structure represented by Formula (2):

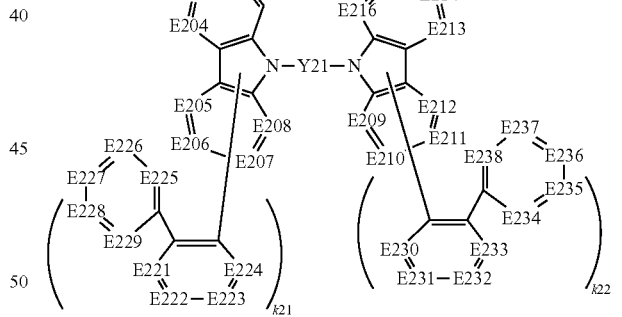

Formula (2)

wherein
Y21 represents an arylene group, a heteroarylene group, or a divalent linking group comprising a combination thereof,
E201 to E216 and E221 to E238 each represent —C(R21)= or —N=, wherein R21 represents a hydrogen atom (H) or a substituent,
at least one of E221 to E229 and at least one of E230 to E238 represent —N=, and
k21 and k22 each represent an integer of 0 to 4, provided that k21+k22 is an integer of 2 or more.

9. The transparent electrode according to claim 1, wherein the compound having a structure represented by Formula (1) has a structure represented by Formula (3):

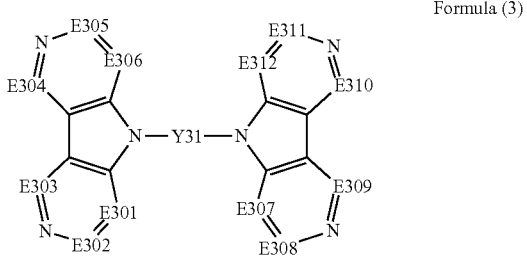

Formula (3)

wherein
E301 to E312 each represent —C(R31)=, wherein R31 represents a hydrogen atom (H) or a substituent, and
Y31 represents an arylene group, a heteroarylene group, or a divalent linking group comprising a combination thereof.

10. The transparent electrode according to claim 1, wherein the compound having a structure represented by Formula (1) has a structure represented by Formula (4):

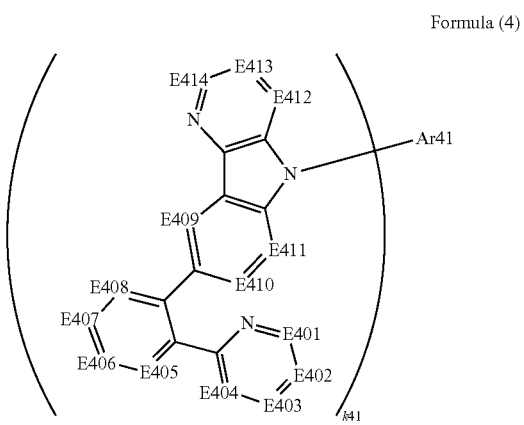

Formula (4)

wherein
E401 to E414 each represent —C(R41)=, wherein R41 represents a hydrogen atom (H) or a substituent,
Ar41 represents a substituted or unsubstituted aromatic hydrocarbon ring or a substituted or unsubstituted aromatic heterocyclic ring, and
k41 represents an integer of 3 or more.

11. The transparent electrode according to claim 1, wherein the compound containing a nitrogen atom or atoms (N) has a structure represented by Formula (1).

12. A transparent electrode comprising:
a nitrogen-containing layer comprising a compound that contains a nitrogen atom or atoms (N) having an unshared electron pair or pairs and has an effective lone pair content n/M of $2.0 \times 10^{-3}$ or more, wherein n represents the number of unshared electron pairs that neither contribute to aromaticity nor are coordinated to metal among the unshared electron pair or pairs of the nitrogen atom or atoms, and M represents the molecular weight of the compound;
an electrode layer provided adjacent to the nitrogen-containing layer and comprising silver (Ag) as a main component and at least one additive element selected from aluminum (Al), gold (Au), indium (In), copper (Cu), palladium (Pd), and platinum (Pt); and
the nitrogen-containing layer further comprises a compound having a structure represented by Formula (5):

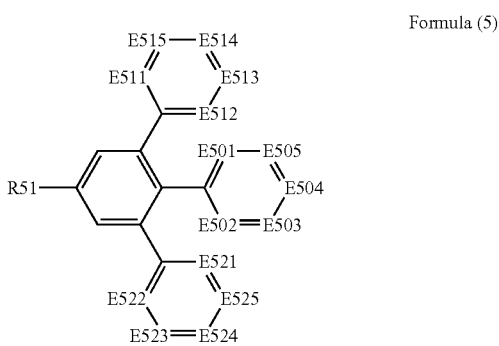

Formula (5)

wherein
R51 represents a substituent,
E501, E502, E511 to E515, and E521 to E525 each represent —C(R52)= or —N=, and
E503 to E505 each represent —C(R52)=, wherein R52 represents a hydrogen atom (H) or a substituent,
at least one of E501 and E502 is —N=,
at least one of E511 to E515 is —N=, and
at least one of E52 to E525 is —N=.

13. The transparent electrode according to claim 12, wherein the compound containing a nitrogen atom or atoms (N) has a structure represented by Formula (5).

14. A transparent electrode comprising:
a nitrogen-containing layer comprising a compound that contains a nitrogen atom or atoms (N) having an unshared electron pair or pairs and has an effective lone pair content n/M of $2.0 \times 10^{-3}$ or more, wherein n represents the number of unshared electron pairs that neither contribute to aromaticity nor are coordinated to metal among the unshared electron pair or pairs of the nitrogen atom or atoms, and M represents the molecular weight of the compound;
an electrode layer provided adjacent to the nitrogen-containing layer and comprising silver (Ag) as a main component and at least one additive element selected from aluminum (Al), gold (Au), indium (In), copper (Cu), palladium (Pd), and platinum (Pt); and
the nitrogen-containing layer further comprises a compound having a structure represented by Formula (6):

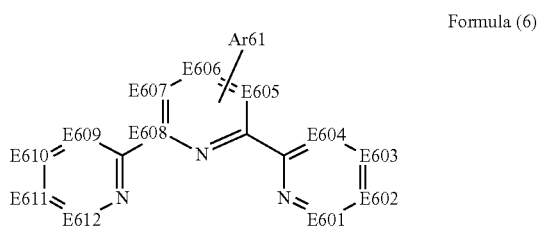

Formula (6)

wherein
E601 to E612 each represent —C(R61)= or —N=, wherein R61 represent a hydrogen atom (H) or a substituent, and
Ar61 represents a substituted or unsubstituted aromatic hydrocarbon ring or a substituted or unsubstituted aromatic heterocyclic ring.

15. The transparent electrode according to claim 14, wherein the compound containing a nitrogen atom or atoms (N) has a structure represented by Formula (6).

16. A transparent electrode comprising:
a nitrogen-containing layer comprising a compound that contains a nitrogen atom or atoms (N) having an unshared electron pair or pairs and has an effective lone pair content n/M of $2.0 \times 10^{-3}$ or more, wherein n represents the number of unshared electron pairs that neither contribute to aromaticity nor are coordinated to metal among the unshared electron pair or pairs of the nitrogen atom or atoms, and M represents the molecular weight of the compound;
an electrode layer provided adjacent to the nitrogen-containing layer and comprising silver (Ag) as a main component and at least one additive element selected from aluminum (Al), gold (Au), indium (In), copper (Cu), palladium (Pd), and platinum (Pt); and
the nitrogen-containing layer further comprises a compound having a structure represented by Formula (7):

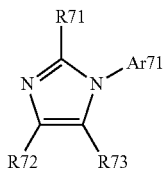

Formula (7)

wherein
R71 to R73 each represent a hydrogen atom (H) or a substituent, and
Ar71 represents an aromatic hydrocarbon ring group or an aromatic heterocyclic ring group.

17. The transparent electrode according to claim 16, wherein
the compound having a structure represented by Formula (7) has a structure represented by Formula (8):

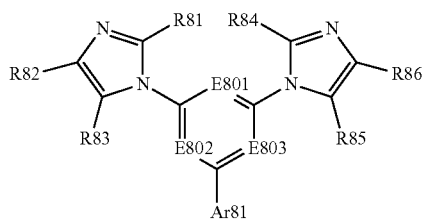

Formula (8)

wherein
R81 to R86 each represent a hydrogen atom (H) or a substituent,
E801 to E803 each represent —C(R87)= or —N=, wherein R87 represents a hydrogen atom (H) or a substituent, and
Ar81 represents an aromatic hydrocarbon ring group or an aromatic heterocyclic ring group.

18. The transparent electrode according to claim 17, wherein the compound having a structure represented by Formula (8) has a structure represented by Formula (8a):

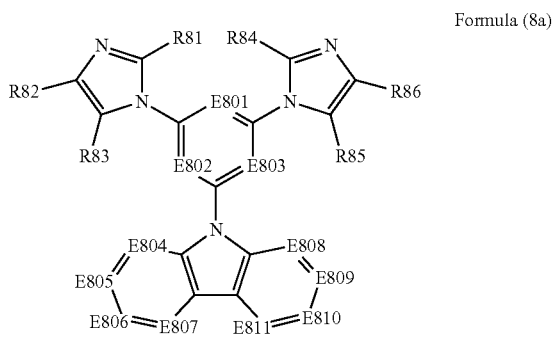

Formula (8a)

wherein
E804 to E811 each represent —C(R88)= or —N=, wherein R88 represents a hydrogen atom (H) or a substituent,
at least one of E808 to E811 is —N=, and
any of E804 to E807 and E808 to E811 may be linked together to form a new ring.

19. The transparent electrode according to claim 18, wherein the compound containing a nitrogen atom or atoms (N) has a structure represented by Formula (8a).

20. The transparent electrode according to claim 16, wherein the compound containing a nitrogen atom or atoms (N) has a structure represented by Formula (7).

* * * * *